US009624509B2

(12) United States Patent
Wolffe et al.

(10) Patent No.: US 9,624,509 B2
(45) Date of Patent: Apr. 18, 2017

(54) MODULATION OF STEM CELLS USING ZINC FINGER PROTEINS

(71) Applicants: Sangamo BioSciences, Inc., Richmond, CA (US); Elizabeth J. Wolffe, Richmond, CA (US)

(72) Inventors: Alan P. Wolffe, Richmond, CA (US); Michael Moore, London (GB); Timothy Farries, Middlesex (GB); Trevor Collingwood, Richmond, CA (US); Fyodor Urnov, Richmond, CA (US)

(73) Assignee: SANGAMO BIOSCIENCES, INC., Richmond, CA (US)

( * ) Notice: Subject to any disclaimer, the term of this patent is extended or adjusted under 35 U.S.C. 154(b) by 0 days.

(21) Appl. No.: 14/270,038

(22) Filed: May 5, 2014

(65) Prior Publication Data
US 2014/0234970 A1 Aug. 21, 2014

Related U.S. Application Data

(62) Division of application No. 10/490,787, filed as application No. PCT/US02/30413 on Sep. 24, 2002, now Pat. No. 8,735,153.

(60) Provisional application No. 60/324,619, filed on Sep. 24, 2001, provisional application No. 60/367,252, filed on Mar. 21, 2002, provisional application No. 60/374,176, filed on Apr. 17, 2002.

(51) Int. Cl.
| | | |
|---|---|---|
| *C12N 15/00* | (2006.01) | |
| *C12N 15/63* | (2006.01) | |
| *C07H 21/04* | (2006.01) | |
| *C12N 15/85* | (2006.01) | |
| *C12N 5/0735* | (2010.01) | |
| *G01N 33/50* | (2006.01) | |
| *C12N 15/62* | (2006.01) | |
| *A61K 35/12* | (2015.01) | |

(52) U.S. Cl.
CPC ........... *C12N 15/85* (2013.01); *C12N 5/0606* (2013.01); *G01N 33/5008* (2013.01); *G01N 33/5023* (2013.01); *G01N 33/5073* (2013.01); *A61K 35/12* (2013.01); *C07H 21/04* (2013.01); *C12N 15/62* (2013.01); *C12N 15/63* (2013.01); *C12N 2501/40* (2013.01); *C12N 2503/02* (2013.01)

(58) Field of Classification Search
CPC ...... C12N 5/0606; C12N 15/62; C12N 15/63; C12N 15/85; C07H 21/04
USPC .............................................. 435/320.1, 455
See application file for complete search history.

(56) References Cited

U.S. PATENT DOCUMENTS

| | | |
|---|---|---|
| 4,186,183 A | 1/1980 | Steck et al. |
| 4,217,344 A | 8/1980 | Vanlerberghe et al. |
| 4,235,871 A | 11/1980 | Papahadjopoulos et al. |
| 4,261,975 A | 4/1981 | Fullerton et al. |
| 4,485,054 A | 11/1984 | Mezei et al. |
| 4,501,728 A | 2/1985 | Geho et al. |
| 4,603,044 A | 7/1986 | Geho et al. |
| 4,774,085 A | 9/1988 | Fidler |
| 4,797,368 A | 1/1989 | Carter et al. |
| 4,837,028 A | 6/1989 | Allen |
| 4,897,355 A | 1/1990 | Eppstein et al. |
| 4,946,787 A | 8/1990 | Eppstein et al. |
| 4,957,773 A | 9/1990 | Spencer et al. |
| 5,049,386 A | 9/1991 | Eppstein et al. |
| 5,173,414 A | 12/1992 | Lebkowski et al. |
| 5,176,996 A | 1/1993 | Hogan et al. |
| 5,187,077 A | 2/1993 | Gearing et al. |
| 5,422,251 A | 6/1995 | Fresco |
| 5,585,245 A | 12/1996 | Johnsson et al. |
| 5,681,559 A | 10/1997 | DiGiusto et al. |
| 5,750,376 A | 5/1998 | Weiss et al. |
| 5,786,538 A | 7/1998 | Barone |
| 5,789,538 A | 8/1998 | Rebar et al. |
| 5,834,266 A | 11/1998 | Crabtree et al. |
| 5,851,832 A | 12/1998 | Weiss et al. |
| 5,914,108 A | 6/1999 | Tsukamoto et al. |
| 5,980,885 A | 11/1999 | Weiss et al. |
| 5,994,313 A | 11/1999 | Crabtree et al. |
| 6,007,988 A | 12/1999 | Choo et al. |
| 6,011,197 A | 1/2000 | Strelchenko et al. |
| 6,013,453 A | 1/2000 | Choo et al. |
| 6,129,911 A | 10/2000 | Faris |
| 6,146,888 A | 11/2000 | Smith et al. |

(Continued)

FOREIGN PATENT DOCUMENTS

| | | |
|---|---|---|
| WO | WO 91/16024 | 10/1991 |
| WO | WO 91/17424 | 11/1991 |

(Continued)

OTHER PUBLICATIONS

Pandey, Prativa, 2007, Abstracts, 59th Southeast regional Meeting of the American Chemical Society, Greenville, SC, United States, GEN-671, Publisher: American Chemical Society, Washington D.C.*
Bryan et al., 2013, http://www.elsevierblogs.com/currentcomments/? p=962, Implications of protein fold switching, p. 1-4.*
Giannola et al., 2000, J. Exp. Med., vol. 192, No. 10. p. 1479-1490.*
Abeyta et al., "Unique Gene Expression Signatures of Independently-Derived Human Embryonic Stem Cell Lines," *Human Molecular Genetics* 13(6):601-608 (2004).
Ahmad et al., "Antibody-Mediated Specific Binding and Cytotoxicity of Liposome-Entrapped Doxorubicin to Lung Cancer Cells In Vitro," *Cancer Res.* 52:4817-4820 (1992).
Allegrucci et al., "Differences Between Human Embryonic Stem Cell Lines," *Human Reproduction Update*, vol. Advance Access published on Aug. 26, 2006 1-18 (2006).
Altincicek et al., "Interaction of the Corepressor Alien With DAX-1 is Abrogated by Mutations of DAX-1 Involved in Adrenal Hypoplasia Congenita," *J. Biol. Chem.* 275:7662-7667 (2000).

(Continued)

*Primary Examiner* — Shin Lin Chen
(74) *Attorney, Agent, or Firm* — Pasternak Patent Law; Susan Abrahamson

(57) ABSTRACT

Methods and compositions for modifying stem cells using one or more ZFPs are disclosed. Such methods and compositions are useful for facilitating processes such as, for example, dedifferentiating cells, differentiating stem cells into the desired phenotype, propagating stem cells and/or facilitating cloning.

3 Claims, 6 Drawing Sheets

(56) References Cited

U.S. PATENT DOCUMENTS

| | | |
|---|---|---|
| 6,258,354 B1 | 7/2001 | Greenberger |
| 6,265,175 B1 | 7/2001 | Gage et al. |
| 6,268,119 B1 | 7/2001 | Sumita et al. |
| 6,270,990 B1 | 8/2001 | Anderson et al. |
| 6,453,242 B1 | 9/2002 | Eisenberg et al. |

FOREIGN PATENT DOCUMENTS

| | | |
|---|---|---|
| WO | WO 93/01275 | 1/1993 |
| WO | WO 93/24641 | 9/1993 |
| WO | WO 94/09119 | 4/1994 |
| WO | WO 94/10292 | 5/1994 |
| WO | WO 94/16718 | 8/1994 |
| WO | WO 95/09233 | 4/1995 |
| WO | WO 95/19431 | 7/1995 |
| WO | WO 96/06166 | 2/1996 |
| WO | WO 96/09543 | 3/1996 |
| WO | WO 98/44350 | 10/1998 |
| WO | WO 98/53057 | 11/1998 |
| WO | WO 98/53058 | 11/1998 |
| WO | WO 98/53059 | 11/1998 |
| WO | WO 98/53060 | 11/1998 |
| WO | WO 98/54311 | 12/1998 |
| WO | WO 99/10508 | 3/1999 |
| WO | WO 99/27092 | 6/1999 |
| WO | WO 00/41566 | 7/2000 |
| WO | WO 00/42219 | 7/2000 |
| WO | WO 01/04296 | 1/2001 |
| WO | WO 01/83793 | 11/2001 |

OTHER PUBLICATIONS

Alvarez et al., "A Phase I Study of Recombinant Adenovirus Vector-Mediated Intraperitoneal Delivery of Herpes Simplex Virus Thymidine Kinase (HSV-TK) Gene and Intravenous Ganciclovir for Previously Treated Ovarian and Extraovarian Cancer Patients," *Human Gene Therapy* 8(5):597-613 (1997).
Anderson, "Human Gene Therapy," *Science* 256:808-813 (1992).
Anderson et al., "Can Stem Cells Cross Lineage Boundaries?" *Nat. Med.* 7:393-395 (2001).
Angelin-Duclos et al., "Commitment to a Plasma Cell Fate is Associated With Blimp-1 Expression In Vivo," *J. Immunol.* 165:5462-5471 (2000).
Antonchuk et al., "HOXB4-Induced Expansion of Adult Hematopoietic Stem Cells Ex Vivo," *Cell* 109:39-45 (2002).
Anzai et al., "Self-Renewal and Differentiation of a Basis Fibroblast Growth Factor-Dependent Multipotent Hematopoietic Cell Line Derived From Embryonic Stem Cells," *Develop. Growth Differ.* 41:51-58 (1999).
Arora et al., "Residues 1-254 of Anthrax Toxin Lethal Factor are Sufficient to Cause Cellular Uptake of Fused Polypeptides," *J. Biol. Chem.* 268:3334-3341 (1993).
Aso et al., "Transcription Syndromes and the Role of RNA Polymerase II General Transcription Factors in Human Disease," *J. Clin. Invest.* 97:1561-1569 (1996).
Ayer et al., "MAD Proteins Contain a Dominant Transcription Repression Domain," *Mol. Cell. Biol.* 16:5772-5781 (1996).
Barahmand-pour et al., "A Role for Stat Family Transcription Factors in Myeloid Differentiation," *Curr. Top. Microbiol. Immunol.* 211:121-128 (1996).
Barnes and Adcock, "Transcription Factors." *Clin. Exp. Allergy* 25(2):46-49 (1995).
Bartsevich et al., "Engineered Zinc Finger Proteins for Controlling Stem Cell Fate," *Stem Cells.* 21(6):632-637 (2003).
Baum et al., "Isolation of a Candidate Human Hematopoietic Stem-Cell Population," *PNAS USA* 89:2804-2808 (1992).
Beerli et al., "Positive and Negative Regulation of Endogenous Genes by Designed Transcription Factors," *Proceedings of the National Academy of Sciences USA* 97(4):1495-1500 (2000).
Behr et al., "Gene Transfer With Synthetic Cationic Amphiphiles: Prospects for Gene Therapy," *Bioconjugate Chem.* 5:382-389 (1994).
Berg and Shi, "The Galvanization of Biology: A Growing Appreciation for the Roles of Zinc," *Science* 271:1081-1085 (1996).
Beug et al., "Avian Erythropoiesis and Erythroleukemia: Towards Understanding the Role of the Biomolecules Involved," *Biochim Biophys Acta* 1288(3):M35-47 (1996).
Bhardwaj et al., "Sonic Hedgehog Induces the Proliferation of Primitive Human Hematopoietic Cells via BMP Regulation," *Nat. Immunol.* 2:172-180 (2001).
Bird et al., "Methylation-Induced Repression—Belts, Braces, and Chromatin," *Cell* 99:451-454 (1990).
Bitko and Barik, "Persistent Activation of Rela by Respiratory Syncytial Virus Involves Protein Kinase C, Underphosphorylated IKappa BBeta , and Sequestration of Protein Phosphatase 2A by the Viral Phosphoprotein," *J. Virol.* 72:5610-5618 (1998).
Bjornson et al., "Turning Brain Into Blood: A Hematopoietic Fate Adopted by Adult Neural Stem Cells In Vivo," *Science* 283:534-537 (1999).
Blaese et al., "Vectors in Cancer Therapy: How Will They Deliver?" *Cancer Gene Ther.* 2:291-297 (1995).
Blaese et al., "T Lymphocyte-Directed Gene Therapy for ADA-SCID: Initial Trial Results After 4 Years," *Science* 270:475-480 (1995).
Boulikas, "Phosphorylation of Transcription Factors and Control of the Cell Cycle," *Crit. Rev. Eukaryot. Gene Expr.* 5:1-77 (1995).
Brandt et al., "Characterization of a Human Hematopoietic Progenitor Cell Capable of Forming Blast Cells Containing Colonies In Vitro," *J. Clinical Investigation* 82:1017-1027 (1988).
Brakenhoff et al., "Molecular Cloning and Expression of Hybridoma Growth Factor in *Escherichia coli*," *Immunol.* 139:4116-4121 (1987).
Brun et al., "The Effects of HOXB4 in Human Primitive Hematopoietic Progenitors are Concentration Dependent: High Levels of HOXB4 Lead to Increased Myeloid Differentiation and a Reduction in Proliferative Capacity," Blood 98, 66a (2001).
Buchschacher et al., "Human Immunodeficiency Virus Vectors for Inducible Expression of Foreign Genes," *J. Virol.* 66:2731-2739 (1992).
Burkert et al., "Early Fetal Hematopoietic Development From In Vitro Differentiated Embryonic Stem Cells," *The New Biologist* 3(7):698-708 (1991).
Burley, "The Tata Box Binding Protein," *Curr. Opin. Struct. Biol.* 6:69-75 (1996).
Carbonetti et al., "Use of Pertussis Toxin Vaccine Molecule PT9K/129G to Deliver Peptide Epitopes for Simulation of a Cytotoxic T Lymphocyte Response," *Abstr. Annu. Meet. Am. Soc. Microbiol.* 95:295 (1995).
Carreira et al., "Brachyury-Related Transcription Factor TBX2 and Repression of the Melanocyte-Specific TRP-1 Promoter," *Mol. Cell. Biol.* 18:5,099-5,108 (1998).
Castella et al., "HES-1 Repression of Differentiation and Proliferation in PC12 Cells: Role for the Helix 3-Helix 4 Domain in Transcription Repression," Mol Cell Biol 2000, 20:6170-6183.
Chattopadhyay et al., "Effect of Single Amino Acid Mutations in the Conserved GDNQ Motif of L Protein of Rinderpest Virus on RNA Synthesis In Vitro and In Vivo," *Virus Research* 99:139-145 (2004).
Cheng, "DNA Modification by Methyltransferases," *Curr. Opin. Struct. Biol.* 5:4-10 (1995).

Chern et al., "The Regulator of MAT2 (ROM2) Protein Binds to Early Maturation Promoters and Represses PVALF-Activated Transcription," *Plant Cell* 8:305-321(1996).

Cho et al., "Analysis of the C-Terminal Region of Arabidopsis Thaliana Apetala1 as a Transcription Activation Domain," *Plant Mol. Biol.* 40:419-429 (1999).

Choo et al., "Toward a Code for the Interactions of Zinc Fingers With DNA: Selection of Randomized Fingers Displayed on Phage," *PNAS USA* 91:11163-11167 (1994).

Choo et al., "Selection of DNA Binding Sites for Zinc Fingers Using Randomized DNAs Reveals Coded Interactions," *PNAS USA* 91:11168-11172 (1994).

Ciana et al., "Leukemic Transformation by the V-Erba Oncoprotein Entails Constitutive Binding to and Repression of an Erythroid Enhancer In Vivo," *EMBO J.* 17(24):7382-7394 (1999).

(56) References Cited

OTHER PUBLICATIONS

Civin et al., "Antigenic Analysis of Hematopoiesis. III. A Hematopoietic Progenitor Cell Surface Antigen Defined by a Monoclonal Antibody Raised Against KG-1A Cells," *J. Immunol.* 133:157-165 (1984).
Clarke-Curtiss & Curtiss, "Analysis of Recombinant DNA Using *Escherichia coli* Minicells," *Methods in Enzymol.* 101:347-362 (1983).
Clarke et al., "Generalized Potential of Adult Neural Stem Cells," *Science* 288:1660-1663 (2000).
Coffman et al., "Improved Renal Function in Mouse Kidney Allografts Lacking MHC Class I Antigens," *J. Immunol.* 151:425-435 (1993).
Colley et al., "Conversion of a Golgi Apparatus Sialyltransferase to a Secretory Protein by Replacement of the NH2-Terminal Signal Anchor With a Signal Peptide," *J. Biol. Chem.* 264:17619-17622 (1989).
Collingwood et al., "Nuclear Receptors: Coactivators, Corepressors and Chromatin Remodeling in the Control of Transcription," J. Mol. Endocrinol. 23: 255-275 (1999).
Cook et al., "Three Conserved Transcriptional Repressor Domains are a Defining Feature of the Tieg Subfamily of SP1-Like Zinc Finger Proteins," *J. Biol. Chem.* 274:29,500-29,504 (1999).
Crepieux et al., "The ETS Family of Proteins: Weak Modulators of Gene Expression in Quest for Transcriptional Partners," *Crit. Rev. Oncog.* 5:615-638 (1994).
Crystal, "Transfer of Genes to Humans: Early Lessons and Obstacles to Success," *Science* 270:404-410 (1995).
Cultraro et al., "Function of the C-MYC Antagonist MAD1 During a Molecular Switch From Proliferation to Differentiation," *Mol Cell. Biol.* 17:2353-2359 (1997).
Damm et al., "Protein Encoded by V-Erba Functions as a Thyroid-Hormone Receptor Antagonist," *Nature* 339:593-597 (1989).
Davis, "Transcriptional Regulation by MAP Kinases," *Mol. Reprod. Dev.* 42:459-467 (1995).
Davis, The Many Faces of Epidermal Growth Factor Repeats, *The New Biologist* 2(5):410-419 (1990).
Deamer & Bangham, "Large Volume Liposomes by an Ether Vaporization Method," *Biochem. Biophys. Acta.* 443:629-634 (1976).
Denisenko et al., "Point Mutations in the WD40 Domain of EED Block its Interaction With EZH2," *Mol. Cell Biol.* 18:5634-5642 (1998).
Deonarain, "Ligand-Targetd Receptor-Mediated Vectors for Gene Delivery," *Expert Opin. Ther. Patents* 8:53-69 (1998).
Derossi et al., "The Third Helix of the Antennapedia Homeodomain Translocates Through Biological Membranes," *J. Biol. Chem.* 269:10444-10450 (1994).
Desjarlais et al., "Toward Rules Relating Zinc Finger Protein Sequences and DNA Binding Site Preferences," *PNAS USA* 89:7345-7349 (1992).
Desjarlais et al., "Use of a Zinc-Finger Consensus Sequences Framework and Specificity Rules to Design Specific DNA Binding Proteins," *PNAS USA* 90:2256-2260 (1993).
Desjarlais et al., "Length-Encoded Multiplex Binding Site Determination: Application to Zinc Finger Proteins," *PNAS USA* 91:11099-11103 (1994).
Dexter, "Haemopoietic Growth Factors," *Br. Med. Bull.* 45(2):337-349 (1989).
Dillon, "Regulating Gene Expression in Gene Therapy," *Trends in Biotechnology* 11:167-175 (1993).
Donnelly et al., "Targeted Delivery of Peptide Epitopes to Class I Major Histocompatibility Molecules by a Modified Pseudomonas Exotoxin," *PNAS USA* 90:3530-3534 (1993).
Donovan et al., "The End of the Beginning for Pluripotent Stem Cells," *Nature* 414:92-97 (2001).
Doyle & Hunt, "Reduced Nuclear Factor Kappa B Expression in Rat Primary Sensory Neurons After Peripheral Nerve Injury," *NeuroReport* 8:2937-2942 (1997).
Dranoff et al., "Phase I Study of Vaccination With Autologous, Irradiated Melanoma Cells Engieered to Secrete Human Granulocyte-Macrophage Colony Stimulating Factor," *Hum. Gene. Ther.* 1:111-123 (1997).
Dunbar et al., "Retrovirally Marked CD34-Enriched Peripheral Blood and Bone Marrow Cells Contribute to Long-Term Engraftment After Autologous Transplantation," *Blood* 85:3048-3305 (1995).
Eck et al., "Chapter Five: Gene-Based Therapy," Goodman & Gilman's *The Pharmacological Basis of Therapeutics*, McGraw-Hill, New York, 77-101 (1996).
Eisenberg & Mcknight, "Promoter Domains Required for Expression of Plasmid-Borne Copies of the Herpes Simplex Virus Thymidine Kinase Gene in Virus-Infected Mouse Fibroblasts and Microinfected Frog Oocytes," *Mol. Cell. Biol.* 5:1940-1947 (1985).
Ellem et al., "A Case Report: Immune Responses and Clinical Course of the First Human Use of Granulocyte Macrophage-Colony-Stimulating-Factor-Transduced Autologous Melanoma Cells for Immunotherapy," *Cancer Immunol. Immunother.* 44(1):10-20 (1997).
Elliot & O'Hare, "Intercellular Trafficking and Protein Delivery by a Herpesvirus Structural Protein," *Cell* 88:223-233 (1997).
Epstein et al., "Tumor-Specific PAX3-FKHR Transcription Factor, but not PAX3, Activates the Platelet-Derived Growth Factor Alpha Receptor," *Mol. Cell. Biol.* 18:4118-4130 (1998).
Evans, "The V-Erba Oncogene is a Thyroid Hormone Receptor Antagonist," *Int. J. Cancer* 4:26-28 (1989).
Fahraeus et al., "Inhibition of PRB Phosphorylation and Cell-Cycle Progression by a 20-Residue Peptide Derived From P16$^{CDKN2/INK4A}$," *Current Biology* 6:84-91 (1996).
Fields et al., "A Novel Genetic System to Detect Protein-Protein Interactions," *Nature* 340:245-246 (1989).
Fisher et al., "The WRPW Motif of the Hairy-Related Basic Helix-Loop-Helix Repressor Proteins Acts as a 4-Amino-Acid Transcription Repression and Protein-Protein Interaction Domain," *Mol. Cell. Biol.* 16:2670-2677 (1996).
Flynn et al., "DNA Binding Discrimination of the Murine DNA Cytosine-C5 Methyltransferase," J. Mol. Biol. 279:101-116 (1998).
Fondell et al., "Unliganded Thyroid Hormone Receptor Inhibits Formation of a Functional Preinitiation Complex: Implications for Active Repression," *Genes Dev.* 7(7B):1400-1410 (1993).
Fondell et al., "Unliganded Thyroid Hormone Receptor Alpha Can Target Tata-Binding Protein for Transcriptional Repression," *Mol. Cell Biol.* 16:281-287 (1996).
Fraley et al., "Entrapment of a Bacterial Plasmid in Phospholipid Vesicles: Potential for Gene Transfer," *PNAS USA* 76:3348-3352 (1979).
Freed et al., "Transplantation of Embryonic Dopamine Neurons for Severe Parkinson's Disease," *N. Engl. J. Med.* 344:710-719 (2001).
Friedman et al., "KAP-1, A Novel Corepressor for the Highly Conserved Krab Repression Domain," *Genes Dev.* 10:2067-2078 (1996).
Galli et al., "Skeletal Myogenic Potential of Human and Mouse Neural Stem Cells," *Nat. Neurosci.* 3:986-991 (2000).
Gangloff et al., "Transcription, Topoisomerases and Recombination," Experientia 50:261-9 (1994).
Gao et al., "Cationic Liposome-Mediated Gene Transfer," Gene Therapy 2:710-722 (1995).
Garcia et al., "RYBP, A New Repressor Protein That Interacts With Components of the Mammalian Polycomb Complex and With the Transcription Factor YY1," *EMBO J.* 18:3404-3418 (1999).
Ginsberg et al., "Up-Regulation of MET but not Neural Cell Adhesion Molecule Expression by the PAX3-FKHR Fusion Protein in Alveolar Rhabdomyosarcoma," Cancer Res. 15: 3542-3546 (1998).
Goff et al., "Identification of Functional Domains in the Maize Transcriptional Activator C1: Comparison of Wild-Type and Dominant Inhibitor Proteins," Genes Dev 5:298-309 (1991).
Gong et al., "A Constitutively Expressed MYC-Like Gene Involved in Anthocyanin Biosynthesis From Perilla Frutescens: Molecular Characterization, Heterologous Expression in Transgenic Plants and Transactivation in Yeast Cells," Plant Mol. Biol. 41:33-44 (1999).

(56) References Cited

OTHER PUBLICATIONS

Goodrich and Tijan, "TBP-TAF Complexes: Selectivity Factors for Eukaryotic Transcription," *Curr. Opin. Cell Biol.* 6:403-409 (1994).
Goodrich et al., "Contacts in Context: Promoter Specificity and Macromolecular Interactions in Transcription," *Cell* 84:825-830 (1996).
Gorecki, "Prospects and Problems of Gene Therapy: An Update," *Expert Opin. Emerging Drugs*. 6(2):187-198 (2001).
Gossen et al.,"Tight Control of Gene Expression in Mammalian Cells by Tetracycline-Responsive Promoter," *PNAS USA* 89:5547-5551 (1992).
Greisman et al., "A General Strategy for Selecting High-Affinity Zinc Finger Proteins for Diverse DNA Target Sites," *Science* 275:657-661 (1997).
Guenther et al., "A Core SMRT Corepressor Complex Containing HDAC3 and TBL1, A WD40-Repeat Protein Linked to Deafness," *Genes Dev.* 14:1048-1057 (2000).
Gunster et al., "Identification and Characterization of Interactions Between the Vertebrate Polycomb-Group Protein BMI1 and Human Homologs of Polyhomeotic," *Mol. Cell. Biol.* 17:2326-2335 (1997).
Gupta et al., "MMIP1: A Novel Leucine Zipper Protein That Reverses the Suppressive Effects of MAD Family Members on C-MYC," *Oncogene* 16:1149-1159 (1998).
Gurdon et al., "The Future of Cloning," *Nature* 402:743-746 (1999).
Hagman et al., "PAX-5/BSAP: Regulator of Specific Gene Expression and Differentiation in B Lymphocytes," *Curr. Top Microbiol. Immunol.* 245:169-194 (2000).
Hagmann et al., "The VP16 Paradox: Herpes Simplex Virus VP16 Contains a Long-Range Activation Domain But Within the Natural Multiprotein Complex Activates Only From Promoter-Proximal Positions," *J. Virol.* 71:5952-5962 (1997).
Han et al., "Ligand-Directed Retroviral Targeting of Human Breast Cancer Cells," *PNAS USA* 92:9747-9751 (1995).
Hansis et al., "OCT-4 Expression in Inner Cell Mass and Trophectoderm of Human Blastocysts," *Mol. Hum. Reprod.* 6:999-1004 (2000).
Hassig et al., "A Role for Histone Deacetylase Activity in HDAC1-Mediated Transcriptional Repression," *PNAS USA* 95:3519-3524 (1998).
He et al., "Transcription Repression by Xenopus Et and Its Human Ortholog TBX3, A Gene Involved in Ulnar-Mammary Syndrome," *PNAS USA* 96:10212-10217 (1999).
Helgason et al., "Overexpression of HOXB4 Enhances the Hematopoietic Potential of Embryonic Stem Cells Differentiated In Vitro," *Blood* 87:2740-2749 (1996).
Hemenway et al., "The BMI-1 Oncoprotein Interacts With Ding and MPH2: The Role of Ring Finger Domains," *Oncogene* 16:2541-2547 (1998).
Hendrich et al., "Genomic Structure and Chromosomal Mapping of the Murine and Human MBD1, MBD2, MBD3, and MBD4 Genes," *Mamm. Genome* 10:906-912 (1999).
Hermonat & Musiczka, "Use of Adeno-Associated Virus as a Mammalian DNA Cloning Vector: Transduction of Neomycin Resistance Into Mammalian Tissue Culture Cells," *PNAS USA* 81:6466-6470 (1984).
Hobo et al., "A BZIP Factor, TRAB1, Interacts With VP1 and Mediates Abscisic Acid-Induced Transcription," *Proc. Natl. Acad. Sci. USA* 96:15348-15353 (1999).
Hope et al., "Production of Large Unilamellar Vesicles by a Rapid Extrusion Procedure. Characterization of Size Distribution, Trapped Volume and Ability to Maintain a Membrane Potential," *Biochem. Biophys. Acta.* 812:55-65 (1985).
Hope et al., "Generation of Multilamellar and Unilamellar Phospholipid Vesicles," *Chem. Phys. Lipids* 40:89-108 (1986).
Hurlin et al., "The Max Transcription Factor Network: Involvement of MAD in Differentiation and an Approach to Identification of Target Genes," *Cold Spring Harb. Symp. Quant. Biol.* 59:109-16 (1994).

Inaba et al., "Generation of Large Numbers of Dendritic Cells From Mouse Bone Marrow Cultures Supplemented With Granulocyte/Macrophage Colony-Stimulating Factor," *J. Exp. Med.* 176:1693-1702 (1992).
Jackson et al., "Phosphorylation of Trans-Cription Factor SP1 by the DNA-Dependent Protein Kinase," *Adv. Second Messenger Phosphoprotein Res.* 28:279-286 (1993).
Jacobs, G. H., "Determination of the Base Recognition Positions of Zinc Fingers from Sequence Analysis," *EMBO J.* 11(12):4507-4517 (1992).
Jamieson et al., "In Vitro Selection of Zinc Fingers With Altered DNA-Binding Specificity," *Biochemistry* 33:5689-5695 (1994).
Jankowski et al., "Flow Cytometric Characterization of Myogenic Cell Populations Obtained via the Preplate Technique: Potential for Rapid Isolation of Muscle-Derived Stem Cells," *Hum. Gene Therapy* 12:619-628 (2001).
Jin & Scotto, "Transcriptional Regulation of the MDR1 Gene by Histone Acetyltransferase and Deacetylase is Mediated by NF-Y," *Mol. Cell Biol.* 18:4377-4384 (1998).
Johann et al., "GLVR1, A Receptor for Gibbon Ape Leukemia Virus, is Homologous to a Phosphate Permease of Neurospora Crassa and is Expressed at High Levels in the Brain and Thymus," *J. Virol.* 66:1635-1640 (1992).
Kang et al., "Zinc Finger Proteins as Designer Transcription Factors," *J. Biol. Chem.* 275(12):8742-8748 (2000).
Kaiser et al., "The Human General Cofactors," *Trends Biochem. Sci.* 21:342-345 (1996).
Kanei-Ishii et al., "Structure and Function of the Proteins Encoded by the MYB Gene Family," *Curr. Top. Microbiol. Immunol.* 211:89-98 (1996).
Kaye et al., "A Signle Amino Acid Substitution Results in Retinoblastoma Protein Defective in Phosphorylation and Oncoprotein Binding," *PNAS USA* 87:6922-6926 (1990).
Kearns et al., "Recombinant Adeno-Associated Virus (AAV-CFTR) Vectors do not Integrate in a Site-Specific Fashion in an Immortalized Epithelial Cell Line," *Gene Ther.* 9:748-755 (1996).
Kim et al., "Transcriptional Repression by Zinc Finger Peptides. Exploring the Potential for Application in Gene Therapy" *J. Biol. Chem.* 272:29795-29800 (1997).
Kim et al., "Hybrid Restriction Enzymes: Zinc Finger Fusions FOK 1 Cleavage Domain," *PNAS* 93:1156-1160 (1996).
Klemm et al., "Dimerization as a Regulatory Mechanism in Signal Transduction," *Annu. Rev. Immunol.* 16:569-592 (1998).
Klimpel et al., "Anthrax Toxin Protective Antigen is Activated by a Cell Surface Protease With the Sequence Specificity and Catalytic Properties of Furin," *PNAS USA* 89:10277-10281 (1992).
Knoepfler et al., "Sin Meets Nurd and Other Tails of Repression," *Cell* 99:447-450 (1999).
Kohn et al., "Engraftment of Gene-Modified Umbilical Cord Blood Cells in Neonates With Adenosine Deaminase Deficiency," *Nat. Med.* 1:1017-1023 (1995).
Koller et al., "Normal Development of Mice Deficient in Beta 2M, MHC Class I Proteins, and CD8+ T Cells," *Science* 248:1227-1230 (1990).
Kotin, "Prospects for the Use of Adeno-Associated Virus as a Vector for Human Gene Therapy," *Human Gene Therapy* 5:793-801 (1994).
Kodama et al., "The Features and Shortcomings for Gene Delivery of Current Non-Viral Carriers," *Current Medicinal Chemistry* 13:2155-2161 (2006).
Krause et al., "Multi-Organ, Multi-Lineage Engraftment by a Single Bone Marrow-Derived Stem Cell," *Cell* 105:369-377 (2001).
Kremer & Perricaudet, "Adenovirus and Adeno-Associated Virus Mediated Gene Transfer," *Br. Med. Bull.* 51(1):31-44 (1995)
Kyba et al., "HOXB4 Confers Definitive Lymphoid-Myeloid Engraftment Potential on Embryonic Stem Cells and Yolk Sac Hematopoietic Progenitors," *Cell* 109:29-37 (2002).
Lagasse et al., "Purified Hematopoietic Stem Cells Can Differentiate Into Hepatocytes In Vivo," *Nat. Med.* 6:1229-1234 (2000).
Laherty et al., "Histone Deacetylases Associated With the MSIN3 Corepressor Mediate MAD Transcriptional Repression," *Cell* 89:349-356 (1997).

(56) References Cited

OTHER PUBLICATIONS

Lai et al., "RBP1 Recruits Both Histone Deacetylase-Dependent and -Independent Repression Activities to Retinoblastoma Family Proteins," *Mol. Cell. Biol.* 19:6632-6641 (1999).
Lai et al., "RBP1 Recruits the MSIN3-Histone Deacetylase Complex to the Pocket of Retinoblastoma Tumor Suppressor Family Proteins Found in Limited Discrete Regions of the Nucleus at Growth Arrest," *Mol. Cell. Biol.* 21:2918-2932 (2001).
Lai et al., "RBP1 Induces Growth Arrest by Repression of E2F-Dependent Transcription," *Oncogene* 18:2091-2100 (1999).
Lamar et al., "Identification of NKL, a Novel Gil-Kruppel Zinc-Finger Protein That Promotes Neuronal Differentiation," *Development* 126:1335-1346 (2001).
Lansdorp and Dragowska, "Long-Term Erythropoiesis From Constant Numbers of CD34+ Cells in Serum-Free Cultures Initiated With Highly Purufied Progenitor Cells From Human Bone Marrow," *J. Exp. Med.* 175:1501-1509 (1992).
LaPierre et al., "Identification of a Novel Transcriptional Repressor Encoded by Human Cytomegalovirus," *J. Virol.* 75:6062-6069 (2001).
Larsson et al., "Analysis of the DNA-Binding Activities of MYC/MAX/MAD Network Complexes During Induced Differentiation of U-937 Monoblasts and F9 Teratocarcinoma Cells," *Oncogene* 15:737-748 (1997).
Lebedeva et al., "Restoring Apoptosis as a Strategy for Cancer Gene Therapy: Focus O P53 and MDA-7," *Seminars in Cancer Biology* 12:169-178 (2003).
Lehmann, "The Molecular Biology of Nucleotide Excision Repair and Double-Strand Break Repair in Eukaryotes," *Genet. Eng.* 17:1-19 (1995).
Lemon et al., "Nuclear Receptor Cofactors as Chromatin Remodelers," *Curr. Opin. Genet. Dev.* 9(5):499-504 (1999).
Leo et al., "The SRC Family of Nuclear Receptor Coactivators," *Gene* 245:1-11 (2000).
Leonetti et al., "Antibody-Targeted Lipsomes Containing Oligodeoxyribonucleotides Complementary to Viral RNA Selectively Inhibit Viral Replication," *PNAS USA* 87:2448-2451 (1990).
Li et al., "Both Corepressors SMRT and N-COR Proteins Exist in Large Protein Complexes Containing HDAC," *EMBO J.* 19:4342-4350 (2000).
Lin et al., "Inhibition of Nuclear Translocation of Transcription Factor NF-B by a Synthetic Peptide Containing a Cell Membrane-Permeable Motif and Nuclear Localization Sequence," *J. Biol. Chem.* 270:14255-14258 (1995).
Liu et al., "Suppression of Growth and Transformation and Induction of Apoptosis by EGR-1," *Cancer Gene Ther.* 5:3-28 (1998).
Liu et al., "Design of Polydactyl Zinc-Finger Proteins for Unique Addressing Within Complex Genomes," *PNAS USA* 94:5525-5530 (1997).
Lovell-Badge, "The Future for Stem Cell Research," *Nature* 414:88-91 (2001).
Luis et al., "TEX27, a Gene Containing a Zinc-Finger Domain, is Up-Regulated During the Haploid Stages of Spermatogenesis," *Experimental Cell Research* 249:320-326 (1998).
Lyman et al., "Structural Analysis of Human and Murine FLT3 Ligand Genomic Loci," *Oncogene* 11(6):1165-1172 (1995).
Malech et al., "Prolonged Production of NADPH Oxidase-Corrected Granulocytes After Gene Therapy of Chronic Granulomatous Disease," *PNAS USA* 94:12133-12138 (1997).
Malik et al., "Transcriptional Regulation Through Mediator-Like Coactivators in Yeast and Metazoan Cells," *Trends Biochem. Sci.* 25:277-283 (2000).
Manteuffel-Cymborowska, "Nuclear Receptors, Their Coactivators and Modulation of Transcription," *Acta. Biochim. Pol.* 46:77-89 (1999).
Margolin et al., "Kruppel-Associated Boxes are Potent Transcriptional Repression Domains," *PNAS USA* 91:4509-4513 (1994).
Markmann et al., "Indefinite Survival of MHC Class I-Deficient Murine Pancreatic Islet Allografts," *Transplantation* 54(6): 1085-1089 (1992).
Martinez et al., "A Human SPT3-TAII31-GCN5-L Acetylase Complex Distinct From Transcription Factor IID," *J. Biol. Chem.* 273:23781-23785 (1998).
Matson et al., "DNA Helicases: Enzymes With Essential Roles in all Aspects of DNA Metabolism," *Bioessays* 16:13-22 (1994).
Maxon et al., "ASH1P is a Site-Specific DNA-Binding Protein That Actively Represses Transcription," *PNAS USA* 98:1495-1500 (2001).
Mayer et al., "Vesicles of Variable Sizes Produced by a Rapid Extrusion Procedure," *Biochem. Biophys. Acta.* 858:161-168 (1986).
McKenna et al., "Nuclear Receptor Coactivators: Multiple Enzymes, Multiple Complexex, Multiple Functions," *J. Steroid Biochem. Mol. Biol.* 69:3-12 (1999).
Meier, "Co-Activators and Co-Repressors: Mediators of Gene Activation by Nuclear Hormone Receptors," *Eur. J. Endocrinol.* 134(2):158-159 (1996).
Merrill et al., "TCF3 and LEF1 Regulate Lineage Differentiation of Multipotent Stem Cells in Skin," *Genes Dev.* 15:1688-1705 (2001).
Mezey et al., "Turning Blood Into Brain: Cells Bearing Neuronal Antigens Generated In Vivo From Bone Marrow," *Science* 290:1779-1782 (2000).
Miller, "Human Gene Therapy Comes of Age," *Nature* 357:455-460 (1992).
Miller et al., "Construction and Properties of Retrovirus Packaging Cells Based on Gibbon Ape Leukemia Virus," *J. Virol.* 65:2220-2224 (1991).
Mistili & Spector, "Applications of the Green Flourescent Protein in Cell Biology and Biotechnology," *Nature Biotechnology* 15:961-964 (1997).
Mitani & Caskey, "Delivering Therapeutic Genes: Matching Approach and Application," *Trends Biotechnol.* 11:162-166 (1993).
Mitchell et al., "Functional Analysis of Secreted and Transmembrane Proteins Critical to Mouse Development," *Nature Genetics* 28:241-249 (2001).
Morgan et al., "Selective In Vitro Growth of T Lymphocytes From Normal Human Bone Marrows," *Science* 193:1007-1008 (1976).
Morrison, "Transformation in *Escherichia coli*: Cryogenic Prseservation of Competent Cells," *J. Bacteriol.* 132:349-351 (1977).
Morrison, "Stem Cell Potential: Can Anything Make Anything?" *Curr. Biol.* 11:R7-9 (2001).
Muzyczka, "Adeno-Associated Virus (AAV) Vectors: Will They Work?" *J. Clin. Invest.* 94:1351 (1994).
Nabel & Felgner, "Direct Gene Transfer for Immunotherapy and Immunization," *Trends Biotechnol.* 11:211-215 (1993).
Nakayama et al., "The Transition to Endoreduplication in Trophoblast Giant Cells is Regulated by the MSNA Zinc Finger Transcription Factor," *Developmental Biology* 199:50-163 (1998).
Nawijn et al., "Enforced Expression of Gata-3 During T Cell Development Inhibits Maturation of CD8 Single-Positive Cells and Induces Thymic Lymphoma in Transgenic Mice," *J. Immunol.* 167:724-732 (2001).
Neering et al., "Transduction of Primitive Human Hematopoietic Cells With Recombinant Adenovirus Vectors," *Blood* 88:1147-1155 (1996).
Nichols et al., "Formation of Pluripotent Stem Cells in the Mammalian Embryo Depends on the POU Transcription Factor OCT4," *Cell* 95:379-391 (1998).
Niwa et al., "Quantitative Expression of OCT-3/4 Defines Differentiation, Dedifferentiation or Self-Renewal of ES Cells," *Nat. Genet.* 24:372-376 (2000).
Nordhoff et al., "Comparative Analysis of Human, Bovine, and Murine OCT-4 Upstream Promoter Sequences," *Mamm. Genome* 12:309-317 (2001).
Novak et al., "Functional Characterization of Protease-Treated Bacillus Anthracis Protective Antigen," *J. Biol. Chem.* 267:17186-17193 (1992).
O'Shea, "X-Ray Structure of the GCN4 Leucine Zipper, a Two-Stranded, Parallel Coiled Coil," *Science* 254:539-544 (1991).
Ogawa et al., "Rice Gibberellin-Insensitive Gene Homolog, Osgai, Encodes a Nuclear-Localized Protein Capable of Gene Activation at Transcriptional Level," *Gene* 245:21-29 (2000).

(56) References Cited

OTHER PUBLICATIONS

Okanami et al., HALF-1 a BZIP-Type Protein, Interacting With the Wheat Transcription Factor HBP-1A Contains a Novel Transcriptional Activation Domain, *Genes Cells* 1:87-99 (1996).
Okano et al., "DNMT2 is not Required for De Novo and Maintenance Methylation of Viral DNA in Embryonic Stem Cells," *Nucleic Acids Res.* 26:2536-2540 (1998).
Okazawa et al., "The OCT3 Gene a Gene for an Embryonictrancription Factor is Controlled by a Retinoic Acid Repressible Enhancer," *The EMBO Journal* 10:2997-3005 (1991).
Oligino et al., "Drug Inducible Transgene Expression in Brain Using a Herpes Simplex Virus Vector," *Gene Ther.* 5:491-496 (1998).
Pain et al., "The Carbonic Anhydrase II Gene, a Gene Regulated by Thyroid Hormone and Erythropoietin, is Repressed by V-ERBA Oncogene in Erythrocytic Cells," *New Biol.* 2:284-294 (1990).
Palva et al., "Secretion of Interferon by Bacillus Subtilis," *Gene* 22:229-235 (1983).
Pedersen, "Studies of In Vitro Differentiation With Embryonic Stem Cells," *Reprod. Fertil. Dev.* 6:543-552 (1994).
Pengue et al., "Repression of Transcriptional Activity at a Distance by the Evolutionarily Conserved Krab Domain Present in a Subfamily of Zinc Finger Proteins," *Nuc. Acids Res.* 22(15): 2908-2914 (1994).
Perelle et al., "Characterization of Clostridium Perfringens IOTA-Toxin Genes and Expression in *Escherichia coli,*" *Infect. Immun.* 61:5147-5156 (1993).
Perotti et al., "Overexpression of the Zinc Finger Protein MZF1 Inhibits Hematopoietic Development From Embryonic Stem Cells: Correlation With Negative Regulation of CD34 and C-MYB Promoter Activity," *Mol. Cell. Biol.* 15(11):6045-6087 (1995).
Pomerantz et al., "Analysis of Homeodomain Function by Structure-Based Design of a Transcription Factor," *PNAS USA* 92:9752-9756 (1995).
Pomerantz et al., "Structure-Based Design of Transcription Factors," *Science* 267:93-96 (1995).
Pomerantz et al., "Structure-Based Design of a Dimeric Zinc Finger Protein," *Biochemistry* 37(4):965-970 (1998).
Prochiantz, "Getting Hydrophilic Compounds Into Cells: Lessons From Homeopeptides," *Current Opinion in Neurobiology* 6:629-634 (1996).
Queva et al., "Sequential Expression of the MAD Family of Transcriptional Repressors During Differentiation and Development," *Oncogene* 16:967-977 (1998).
Rao, "Conserved and Divergent Paths that Regulate Self-Renewal in Mouse and Human Mbryonic Stem Cells," *Developmental Biology* 275:269-286 (2004).
Rebar et al., "Zinc Finger Phage: Affinity Selection of Fingers With New DNA-Binding Specifities," *Science* 263:671-673 (1994).
Reimold et al., "Plasma Cell Differentiation Requires the Transcription Factor XBP-1," *Nature* 412:300-307 (2001).
Remy et al., "Gene Transfer With a Series of Lipophilic DNA-Binding Molecules," *Bioconjugate Chem.* 5:647-654 (1994).
Rendahl et al., "Regulation of Gene Expression In Vivo Following Transduction by Two Separate RAAV Vectors," *Nat. Biotechnol.* 16:757-761 (1998).
Renneisen et al., "Inhibition of Expression of Human Immunodeficiency Virus-1 In Vitro by Antibody-Targeted Liposomes Containing Antisense RNA to the ENV Region," *J. Biol. Chem.* 265:16337-16342 (1990).
Reya et al., "Stem Cells, Cancer, and Cancer Stem Cells," *Nature* 414:105-111 (2001).
Reynolds and Weiss, "Generation of Neurons and Astrocytes From Isolated Cells of the Adult Mammalian Central Nervous System," *Science* 255:1707-1710 (1992).
Robertson et al., "DNMT1 Forms a Cokplex With RB, E2F1 and HDAC1 and Represses Transcription From E2F-Responsive Promoters," *Nature Genet.* 25:338-342 (2000).
Robertson, "Derivation and Maintenance of Embryonic Stem Cell Cultures," *Methods Mol. Biol.* 75:173-184 (1997).

Robyr et al., "Nuclear Hormone Receptor Coregulators in Action: Diversity for Shared Tasks," *Mol. Endocrinol.* 14:329-347 (2000).
Roeder, "Nuclear RNA Polymerases: Role of General Initiation Factors and Cofactors in Eukaryotic Transcription," *Methods Enzymol.* 273:165-171 (1996).
Rolink et al., "IL-2 Receptor Alpha Chain (CD25, TAC) Expression Defines a Crucial Stage in Pre-B Cell Development," *Int. Immunology* 6:1257-1264 (1994).
Rosen et al., "Intracellular Receptors and Signal Transducers and Activators of Transcription Superfamilies: Novel Targets for Small-Molecule Drug Discovery," *J. Med. Chem.* 38:4855-4874 (1995).
Rosenecker et al., "Adenovirus Infection in Cystic Fibrosis Patients: Implications for the Use of Adenoviral Vectors for Gene Transfer," *Infection* 24(1):5-8 (1996).
Rudinger, "Characteristics of the Amino Acids as Components of a Peptide Hormone Sequence," *Peptide Hormones*, Edited by Parsons, University Park Press, Baltimore 1-7 (1976).
Ryan et al., "MYC Oncogenes:The Enigmatic Family," *Biochem. J.* 314:713-721 (1996).
Sabbattini et al., "Binding of Ikaros to the Lambda5 Promoter Silences Transcription Through a Mechanism That Does Not Require Heterochromatin Formation," *EMBO J.* 202812-2822 (2001).
Sadowski, "Site-Specific Genetic Recombination: Hops, Flips, and Flops," *FASEB J.* 7:760-767 (1993).
Saijoh et al., "Identification of Putative Downstream Genes of OCT-3, a Pluripotentcell-specific Transcription Factor," *Genes to Cells* 1:239-252(1996).
Sakaguchi et al., "DNA Damage Activates P53 Through a Phosphorylation-Acetylation Cascade," *Genes Dev.* 12:2831-2841 (1998).
Samulski et al., "Helper-Free Stocks of Recombinant Adeno-Associated Viruses: Normal Integration Does Not Require Viral Gene Expression," *J. Virol.* 63:3822-3828 (1989).
Samar, "DNA Repair in Humans," *Ann. Rev. Genet.* 29:69-105 (1995).
Sap et al., "Repression of Transcription Mediated at a Thyroid Hormone Response Element by the V-ERB-A Oncogene Product," *Nature* 340:242-244 (1989).
Satijn et al., "Ring1 is Assopciated With the Polycomb Group Protein Complex and Acts as a Transcriptional Repressor," *Mol. Cell. Biol.* 17:4105-4113 (1997).
Sato et al., "Molecular Signature of Human Embryonic Stem Cells and Its Comparison With the Mouse," *Developmental Biology* 260:404-413 (2003).
Sauvageau et al., "Overexpression of HOXB4 in Hematopoietic Cells Causes the Selective Expansion of More Primitive Populations In Vitro and In Vivo," *Genes Dev.* 9:1753-1765 (1995).
Schonthal et al., "Regulation of Gene Expression by Serine/Threonine Protein Phosphates," *Cancer Biol.* 6:239-248 (1995).
Sebo et al., "Cell-Invasive Activity of Epitope-Tagged Adenylate Cyclase of Bordetella Pertussis Allows In Vitro Presentation of a Foreign Epitope to CD8+ Cytotoxic T Cells," *Infect. Immun.* 63:3851-3857 (1995).
Seipal et al., "Different Activation Domains Stimulates Transcription From Remote ('Enhancer') and Proximal ('Promoter') Positions," *EMBO J.* 11:4961-4968 (1992).
Sewalt et al., "C-Terminal Binding Protein is a Transcriptional Repressor That Interacts With a Specific Class of Vertebrate Polycomb Proteins," *Mol. Cell. Biol.* 19:777-787 (1999).
Sgouras et al., "ERF: An ETS Domain Protein With Strong Transcriptional Repressor Activity, Can Suppress ETS-Associated Tumorigenesis and is Regulated by Phosphorylation During Cell Cycle and Mitogenic Stimulation," *EMBO J.* 14:4781-4793 (1995).
Simon, "Gotta Have GATA," *Nat. Genet.* 11:9-11 (1995).
Shaknovitch et al., "The Promyelocytic Leukemia Zinc Finger Protein Affects Myeloid Cell Growth, Differentiation, and Apoptosis," *Mol. Cell Biol.* 18(9):5533-5545 (1998).
Shie et al., "Role of Gut-Enriched Kruppel-Like Factor in Colonic Cell Growth and Differntiation," *Am. J. of Gastrointest Liver. Physiol.* 279:G806-G814 (2000).
Schöler et al., "New Type of POU Domain in Germ Line-Specific Protein OCT-4," *Nature* 344:435-439 (1990).

(56) References Cited

OTHER PUBLICATIONS

Skarnes, "Gene Trapping Methods for the Identification and Functional Analysis of Cell Surface Proteins in Mice," *Meth. Enzymology* 328:592-615 (2000).
Skolnick et al., "From Genes to Protein Structure and Function: Novel Applications of Computational Approaches in the Genomic Era," *Trends in Biotech.* 18:34-39 (2000).
Smallwood et al., "Different Substitutions at Conserved Amino Acids in Domains II and III in the Sendai L RNA Polymerase Protein Inactive Viral RNA Synthesis," *Virology* 304:135-145 (2002).
Solecki et al., "Activated NOTCH2 Signaling Inhibits Differentiation of Cerebellar Granule Neuron Precursors by Maintaining Proliferation," *Neuron* 31:557-568 (2001).
Sommer et al., "Identification and Characterization of Specific DNA-Binding Complexes Containing Members of the MYC/MAX/MAD Network of Transcriptional Regulators," *J. Biol. Chem.* 273:6632-6642 (1998).
Sommerfelt et al., "Receptor Interference Groups of 20 Retroviruses Plating on Human Cells," *Virol.* 176:58-69 (1990).
Sprenger-Haussels et al., "Transactivation Properties of Parsley Proline-Rich BZIP Transcription Factors," *Plant J.* 22:1-8 (2000).
Spriggs, "Genomic Structure, Induction, and Production of TNF-Alpha," *Immunol Ser.* 56:3-34 (1992).
Spriggs et al., "Recombinant Human CD40 Ligand Stimulates B Cell Proliferation and Immunoglobulin E Secretion," *J. Exp. Med.* 176:1543-1550 (1992).
Stenmark et al., "Peptides Fused to the Amino-Terminal End of Diphtheria Toxin Are Translocated to the Cytosol," *J. Cell. Biol.* 113:1025-1032 (1991).
Sterman et al., "Adenovirus-Mediated Herpes Simplex Virus Thymidine Kinase/Ganciclovir Gene Therapy in Patients With Localized Malignancy: Results of a Phase I Clinical Trial in Malignant Mesothelioma," *Hum. Gene Ther.* 7:1083-1092 (1998).
Stunnenberg et al., "Leukemia: The Sophisticated Subversion of Hematopoiesis by Nuclear Receptor Oncoprotein," *Biochem. Biophys. Acta.* 1423(1):F15-33 (1999).
Sucov et al., "Retinoic Acid and Retinoic Acid Receptors in Development," *Mol. Neurobiol.* 10(23):169-184 (1995).
Syntichaki & Thireos, "The GCN5-ADA Complex Potentiates the Histone Acetyltransferase Activity of GCN5," *J. Biol. Chem.* 273:24414-24419 (1998).
Szoka et al., "Comparative Properties and Methods of Preparation of Lipid Vesicles (Liposomes)," *Ann. Rev. Biophys. Bioeng.* 9:467-508 (1980).
Tang et al., "Lack of Replicative Senescence in Cultured Rat Oligodendrocyte Precursor Cells," *Science* 291:868-871 (2001).
Tate et al., "Capturing Novel Mouse Genes Encoding Chromosomal and Other Nuclear Proteins," *J. Cell. Sci.* 111:2575-2585 (1998).
Taunton et al., "A Mammalian Histone Deacetylase Related to Yeast Transcriptional Regulator RPD3P," *Science* 272:408-411 (1996).
Telfer et al., "Expression and Function of a Stem Cell Promoter for the Murine CBFALPHA2 Gene: Distinct Roles and Regulation in Natural Killer and T Cell Development," *Dev. Biol.* 229:363-382 (2001).
Theise et al., "Liver From Bone Marrow in Humans," *Hepatology* 32:11-16 (2000).
Thiesen et al., "Multiple Genes Encoding Zinc Finger Domains Are Expressed in Human T Cells," *New Biologist* 2(4)363-374 (1990).
Thomas et al., "Progress and Problems With the Use of Viral Vectors for Gene Therapy," *Nature Reviews/Genetics* 4:346-358 (2003).
Thompson et al., "Cloning and Characterization of Two Yeast Genes Encoding Members of the CCCH Class of Zinc Finger Proteins: Zinc Finger-Mediated Impairment of Cell Growth," *Gene* 174:225-233 (1996).
Toma et al., "Isolation of Multipotent Adult Stem Cells From the Dermis of Mammalian Skin," *Nat. Cell. Biol.* 3:778-784 (2001).
Tomasinsig et al., "The Cathelicidins-Structure, Function and Evolution," *Current Protein and Peptide Science* 6:23-34 (2005).
Topf et al., "Regional 'Pro-Drug' Gene Therapy: Intravenous Administration of an Adenoviral Vector Expressing the *E. coli* Cytosine Deaminase Gene and Systemic Administration of 5-Fluorocytosine Suppresses Growth of Hepatic Metastasis of Colon Carcinoma," *Gene Ther.* 5:507-513 (1998).
Torchia et al., "Co-Activators and Co-Repressors in the Integration of Transcriptional Responses," *Curr. Opin. Cell. Biol.* 10:373-383 (1998).
Tratschin et al., "Adeno-Associated Virus Vector for High-Frequency Integration, Expression, and Rescue of Genes in Mammalian Cells," *Mol. Cell. Biol.* 5:3251-3260 (1985).
Tratschin et al., "A Human Parvovirus, Adeno-Associated Virus, as a Eucaryotic Vector: Transient Expression and Encapsidation of the Procaryotic Gene for Chloramphenicol Acetyltransferase," *Mol. Cell. Biol.* 4:2072-2081 (1984).
Trimarchi et al., "The E2F6 Transcription Factor is a Component of the Mammalian BMI1-Containing Polycomb Complex," *PNAS USA* 98:1519-1524 (2001).
Tyler et al., "The 'Dark Side' of Chromatin Remodeling: Repressive Effects on Transcription," *Cell* 99:443-446 (1999).
Ulmasov et al., "Activation and Repression of Transcription by Auxin-Response Factors," *Proc. Natl. Acad. Sci. USA* 96:5844-5849 (1999).
Underhill et al., "A Novel Nuclear Receptor Corepressor Complex, N-COR, Contains Components of the Mammalian SWI/SNF Complex and the Corepressor KAP-1,"*J. Biol. Chem.* 275:40463-40470 (2000).
Urnov et al., "Targeting of N-COR and Histone Deacetylase 3 by the Oncoprotein V-ERBA Yields a Chromatin Infrastructure-Dependent Transcriptional Repression Pathway," *EMBO J.* 19:4074-4090 (2000).
Urrutia et al., "Exploring the Role of Homeobox and Zinc Finger Proteins in Pancreatic Cell Proliferation, Differentiation, and Apoptosis," *Int. J. Pancreatology* 22(1):1-14 (1997).
Utley et al., "Transcriptional Activators Direct Histone Acetyltransferase Complexes to Nucleosomes," *Nature* 394:498-502 (1998).
Van Brunt, "Molecular Farming: Transgenetic Animals as Bioreactors," *Biotechnology* 6(10):1149-1154 (1988).
Van den Wyngaert et al., "Cloning and Analysis of a Novel Human Putative DNA Methyltransferase," *FEBS Lett.* 426:283-289 (1998).
Van der Vlag et al., "Transcriptional Repression Mediated by the Human Polycomb-Group Protein EED Involves Histone Deacetylation," *Nature Genet.* 23:474-478 (1999).
Verma et al., "Gene Therapy-Promises, Problems and Prospects," *Nature* 389:239-242 (1997).
Vigne, "Third-Generation Adeno Vectors for Gene Therapy," *Restorative Neurology and Neuroscience* 8:35-36 (1995).
Vi Avicencio et al., "The Sonic Hedgehog-Patched-GLI Pathway in Human Development and Disease," *Am. J. Hun. Genet.* 67:1047-1054 (2000).
Vos, "CIS and Trans Mechanisms of DNA Repair," *Curr. Opin. Cell Biol.* 4:385-395 (1992).
Wagner et al., "Efficient and Persistent Gene Transfer of AAV-CFTR in Maxillary Sinus," *Lancet* 351:9117 1702-1703 (1998).
Wang et al., "Ph—Sensitive Immunoliposome Mediates a Target Cell—Specific Delivery and Controlled Expression of a Foreign Gene in Mouse," *PNAS USA* 84:7851-7855 (1987).
Wang et al., "Postive and Negative Regulation of Gene Expression in Eukaryotic Cells With an Inducible Transcritional Regulator," *Gene Ther.* 4:432-441 (1997).
Wang, "Nuclear Protein Tyrosine Kinases," *Trends Biochem. Sci.* 19:373-376 (1994).
Wasylyk et al., "The ETS Family of Transcription Factors," *Eur. J. Biochem.* 211:7-18 (1993).
Wedel et al., "The C/EBP Family of Transcription Factors," *Immunobiology* 193:171-185 (1995).
Weiss et al., "GATA Transcription Factors: Key Regulators of Hematopoiesis," *Exp. Hematol.* 23:99-107 (1995).
Weissman et al., "Stem and Progenitor Cells: Origins, Phenotypes, Lineage Commitments, and Transdifferentiations," *Ann. Rev. Cell Dev. Biol.* 17:387-403 (2001).

(56) References Cited

OTHER PUBLICATIONS

Welsh et al., "Adenovirus-Mediated Gene Transfer for Cystic Fibrosis: Part A. Safety of Dose and Repeat Administration in the Nasal Epithelium. Part B. Clinical Efficacy in the Maxillary Sinus," *Hum. Gene Ther.* 2:205-218 (1995).

West et al., "Gene Expression in Adeno-Associated Virus Vectors: The Effects of Chimeric MRNA Structure, Helper Virus, and Adenovirus VA1 RNA," *Virology* 160:38-47 (1987).

Williams et al., "Low Density Lipoprotein Receptor-Independent Hepatic Uptake of a Synthetic, Cholesterol-Scavenging Lipoprotein: Implications for the Treatment of Receptor-Deficient Atherosclerosis," *PNAS USA* 85:242-246 (1988).

Wilson et al., "Formation of Infectious Hybrid Virions With Gibbon Ape Leukemia Virus and Human T-Cell Leukemia Virus Retroviral Envelope Glycoproteins and the GAG and POL Proteins of Moloney Murine Leukemia Virus," *J. Virol.* 63:2374-2378 (1989).

Witzgall et al., "The Kruppel-Associated Box-A (KRAB-A) Domain of Zinc Finger Proteins Mediates Transcriptional Repression," *PNAS USA* 91:4514-4518 (1994).

Wolffe, "Histone Deacetylase: A Regulator of Transcription," *Science* 272:371-372 (1996).

Wong et al., "Trance is a Novel Ligand of the Tumor Necrosis Factor Receptor Family That Activates C-JUN N-Terminal Kinase in T Cells," *J. Biol. Chem.* 272(40):25190-25194 (1997).

Wood, "DNA Repair in Eukaryotes," *Ann. Rev. Biochem.* 65:135-67 (1996).

Wu et al., "Functional Analysis of HD2 Histone Deacetylase Homologues in Arabidopsis Thaliana," *Plant J.* 22:19-27 (2000).

Wu et al., "Building Zinc Fingers by Selection: Toward a Therapeutic Application," *PNAS USA* 92:344-348 (1995).

Yan et al., "Tissue Factor Transcription Driven by EGR-1 is a Critical Mechanism of Murine Pulmonary Fibrin Deposition in Hypoxia," *PNAS USA* 95:8298-8303 (1998).

Yew et al., "MOS and the Cell Cycle: The Molecular Basis of the Transformed Phenotype," *Curr. Opin. Genet. Dev.* 3:19-25 (1993).

Yu et al., "Progress Towards Gene Therapy for HIV Infection," *Gene Therapy* 1:13-26 (1994).

Zardo & Caiafa, "The Unmethylated State of CPG Islands in Mouse Fibroblasts Depends on the Poly(ADP-Ribosyl)ation Process," *J. Biol. Chem.* 273:16517-16520 (1998).

Zazopoulos et al., "DNA Binding and Transcriptional Repression by DAX-1 Blocks Steroidogenesis," *Nature* 390:311-315 (1997).

Zenke et al., "V-ERBA Specifically Suppresses Transcription of the Avian Erythrocute Anion Transporter (Band 3) Gene," *Cell* 52:107-119 (1988).

Zenke et al., "V-ERBA Oncogene Activation Entails the Loss of Hormone-Dependant Regulator Activity of C-ERBA," *Cell* 61:1035-1049 (1990)).

Zhang et al., "A Conserved {Alpha}-Helical Motif Mediates the Interaction of SP1-Like Transcriptional Repressors With the Corepressor MSIN3A," *Mol. Cell. Biol.* 21:5041-5049 (2001).

Zhang et al., "Synthetic Zinc Finger Transcription Factor Action at an Endogenous Chromosomal Site. Activation of the Human Erythropoietin Gene," *Journal of Biological Chemistry* 275(43):33850-33860 (2000).

Zhang et al., "The Mechanism of Action of Thyroid Hormones," *Ann. Rev. Physiol.* 62:439-466 (2000).

\* cited by examiner

MODULATION OF STEM CELLS USING ZINC FINGER PROTEINS

CROSS-REFERENCE TO RELATED APPLICATIONS

This application is a divisional of U.S. patent application Ser. No. 10/490,787, filed May 31, 2006, which is a 371 application of PCT/US02/30413, filed Sep. 24, 2002 which claims the benefit of the following U.S. provisional patent application Nos. 60/324,619, filed Sep. 24, 2001; 60/367,252, filed Mar. 21, 2002, and 60/374,176, filed Apr. 17, 2002. The disclosures of all of the aforementioned applications are hereby incorporated by reference in their entireties for all purposes.

BACKGROUND

Stem cells are undifferentiated cells that exist in many tissues of embryos and adult mammals. Both adult and embryonic stem cells are able to differentiate into a variety of cell types and, accordingly, may be a source of replacement cells and tissues that are damaged in the course of disease, infection, or because of congenital abnormalities. (See, e.g., Lovell-Badge *Nature* 2001, 414:88-91; Donovan et al. *Nature* 2001, 414:92-97). Various types of putative stem cells exist which; when they differentiate into mature cells, carry out the unique functions of particular tissues, such as the heart, the liver, or the brain. Pluripotent stem cells are thought to have the potential to differentiate into almost any cell type, while multipotent stem cells are believed to have the potential to differentiate into many cell types (Robertson, Meth. Cell Biol. 75:173, 1997; and Pedersen, Reprod. Fertil. Dev. 6:543, 1994).

However, certain cell types (such as nerve cells and cardiac cells) differentiate during development and adult organisms do not replace these cells. It would be of particularly great value in treating a wide variety of diseases to have renewable sources of stem cells that can reliably differentiate into the desired phenotype. By way of example, Parkinson's Disease (PD) is a progressive degenerative disorder that appears to be associated with the death of dopamergic neurons extending from the substantia nigra of the brain into the neighboring striatum. Attempts to treat PD by transplanting stem cells collected from the developing brains of aborted fetuses have had mixed results. (See, e.g., Freed et al. (2001) N. Engl. J. Med. 344:710-719). Further, ethical considerations have mitigated against the use of these embryonic or fetal stem cells. Additionally, it has proven difficult to discover conditions under which embryonic or adult stem cells differentiate into the desired phenotype.

Furthermore, even in those cell types, such as epithelial cells and hematopoietic cells that are replaced in adult organisms it has been a significant challenge to readily and inexpensively obtain stem cells in significant quantities. For example, mammalian hematopoietic cells (e.g., lymphoid, myeloid and erythroid cells) are all believed to be generated by a single cell type called the hematopoietic "stem cell." (Civin et al. (1984) J. Immunol. 133:157-165). However, these hematopoietic stem cells are very rare in adults, accounting for approximately 0.01% of bone marrow cells and isolation based on cell surface proteins such as CD34 results in very small yields. Schemes to fractionate human hematopoietic cells into lineage committed and non-committed progenitors are technically complicated and often do not permit the recovery of sufficient cells to address multi-lineage differentiation. (see, e.g., Berenson et al., 1991; Terstappen et al., 1991; Brandt et al. (1988) J. Clinical Investigation 82:1017-1027; Landsdorp and Dragowska (1992) J. Exp. Med. 175:1501-1509; Baum et al. (1992) Proc. Natl. Acad. Sci. 89:2804-2808).

Similarly, existing protocols that induce differentiation ex vivo exert little control over cell fate, thereby yielding diverse and impure cell populations that are inadequate for projects involving ex vivo reconstitution of the immune system. (See, e.g., Clarke et al. *Science* 2000, 288:1660-1663; Bjornson et al. *Science* 1999, 283:534-533; Galli et al. *Nat Neurosci* 2000, 3:986-991; Mezey et al. *Science* 2000, 290:1779-1782; Toma et al. *Nat Cell Biol* 2001, 3:778-784; Weissman et al. *Annu Rev Cell Dev Biol* 2001, 17:387-403; Anderson et al. *Nat Med* 2001, 7:393-395; Morrison *Curr Biol* 2001, 11:R7-9; Lagasse et al. *Nat Med* 2000, 6:1229-1234; Krause et al. *Cell* 2001, 105:369-377). In addition, certain existing protocols for stem cell growth and differentiation are dependent on the use of feeder cells which necessitates the efficient scale-up of cell culture and creates associated risks including, infection, cell fusion and/or contamination.

Therefore, although embryonic stem cells (ES cells) can be maintained in culture in an undifferentiated state, ex vivo conversion to a desired cell type is difficult. See, e.g., Clarke et al. *Science* (2000) 288:1660-1663. Similarly, adult stem cells are very difficult to expand in culture. See, e.g., Reya et al. *Nature* 2001, 414:105-111; Tang et al. *Science* 2001, 291:868-871.

Thus, there is a clear need to develop methods for identifying, propagating and altering the state (e.g., by differentiation or dedifferentiation) of stem cells to provide a source of cells that are transplantable to the CNS, PNS, or other tissues in vivo in order to replace damaged or diseased tissue.

SUMMARY

Described herein are compositions and methods that utilize the specific gene regulatory ability of designed and/or selected zinc finger proteins with regard to stem cells. In particular, engineered zinc finger proteins (ZFPs) can be used to dedifferentiate cells to allow continued proliferation; to direct the fate of stem cells towards a particular differentiated state; and/or to dedifferentiate nuclei into an oocyte or egg type phenotype.

Thus, in one aspect, described herein are methods of altering the state of differentiation in a cell or population of cells, comprising the step of administering one or more engineered ZFPs to said cell or population of cells, wherein the ZFPs alter the state of cellular differentiation. In certain embodiments, the alteration comprises dedifferentiating the cell (or population) into a less specialized state while in other embodiments, the alteration comprises differentiating the cell (or population) into a more specialized state. In still further embodiments, the cell population comprises one or more pluripotent or multipotent stem cells and the altering comprises enhancing proliferation of said pluripotent or multipotent stem cells. In certain embodiments, the cell is a stem cell and the altering comprises differentiating said stem cell into a particular selected lineage.

In certain embodiments, a method to dedifferentiate a specialized cell into a pluripotent or multipotent stem cell phenotype comprising administering to the cell an effective amount of one or more ZFPs is provided. In certain embodiments, a polynucleotide encoding a ZFP is administered.

The ZFP is preferably engineered to specifically modulate expression of one or more genes involved in dedifferentiation or reprogramming of a somatic cell.

In another aspect, described herein is a method for propagating or expanding stem cell populations comprising administering to the stem cell population an effective amount of one or more ZFPs that specifically target and modulate expression of genes involved in growth in culture. For example, the ZFPs can modulate expression of growth factors such as epidermal growth factors (EGFs), fibroblast growth factors (e.g., betaFGF), and the like.

In yet another aspect, described herein is a method for directing a stem cell to a particular differentiated phenotype.

In any of the methods described herein, one or more of the ZFPs modulate expression of genes involved in growth or differentiation, for example, one or more factors selected from the group consisting of FGF-1, FGF-2, EGF, EGF-like ligands, TGFalpha, IGF-1, TGFbeta, betaFGF, ciliary neurotrophic factor, retinoic acid receptor, activin, interleukins, the Bcl-2 gene product, platelet-derived growth factor (PDGF), nerve growth factor (NGF), a macrophage inflammatory protein, tumor necrosis factor alpha, OCT 3/4, GATA-4 and HOXB4. In other embodiments, one or more of the ZFPs modulate expression of one or more HLA proteins. The modulation of gene expression may comprise repression or activation. Further, in any of the methods described herein the altering can be performed in vitro, in vivo or ex vivo.

In any of the methods described herein, one or more of the ZFPs are administered as polynucleotides encoding the ZFP or as polypeptides.

In another aspect, compositions comprising multipotent/pluripotent stem cells or populations of cells of a selected lineage are provided, for example compositions produced by any of the methods described herein. In preferred embodiments, the compositions are 80%-100% (or any integer therebetween) purified (e.g., 80%-100% of the cells in the composition are stem cells or cells of a particular lineage), preferably 95%-100% pure.

In yet another aspect, a method for screening an agent which affects proliferation, differentiation or survival of stem cells is provided, the method comprising administering the agent to any of the compositions described herein; and determining if said agent has an effect on proliferation, differentiation or survival of said cell population. In certain embodiments, the determining comprises determining the effects of said agent on differentiation of said cell population. In any of these methods, the agent is selected from the group consisting of small molecules, biological agents, peptides or combinations thereof.

In any of the methods or compositions described herein, the cell can be a prokaryotic cell or a eukaryotic cell, for example a plant cell or an animal cell (e.g., a human cell or a cell from a domestic animal such as a sheep, cow or pig).

These and other embodiments will be readily apparent to one of skill in the art in view of the teachings herein.

DETAILED DESCRIPTION

Figure 1:
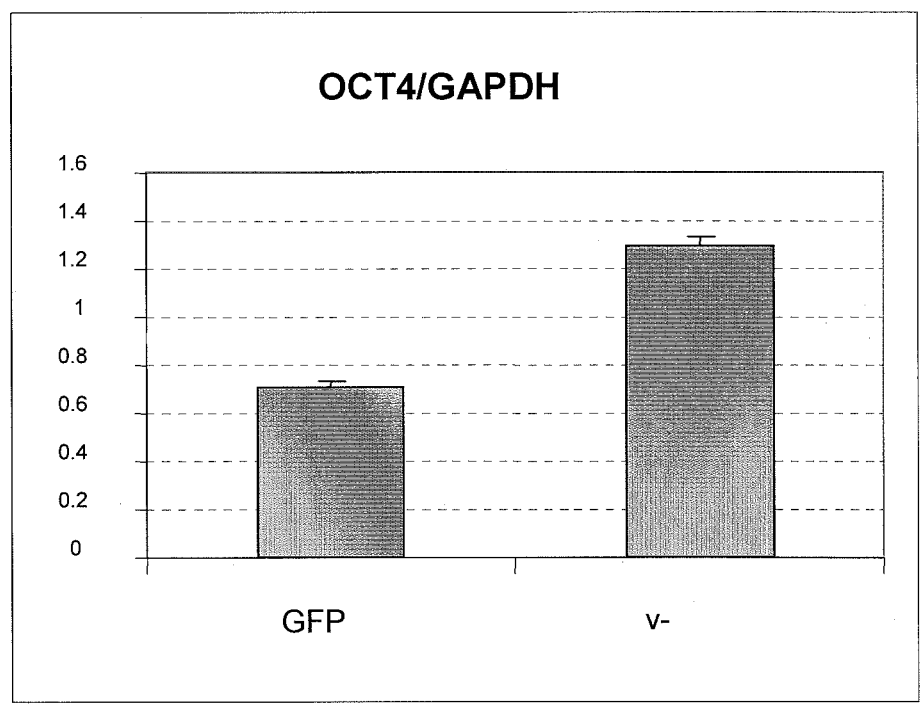
FIG. 1 shows levels of OCT4 mRNA in cells transfected with a vector encoding a fusion between an OCT4-targetd ZFP and the VP16 transcriptional activation domain (v-1547), compared to cells transfected with a vector encoding green fluorescent protein (GFP).

Disclosed herein are compositions and methods, particularly zinc finger protein-containing compositions, useful for (1) dedifferentiating specialized cells into a stem cell fate; (2) propagating stem cells for long periods of time in culture; (3) differentiating stem cells into a desired specialized phenotype; (4) increasing cloning efficiency, for example by reprogramming somatic nuclei; (5) reducing rejection of allogenic stem cell grafts; and/or (6) parsing the transcription regulatory program that unravels during stem cell ontogeny.

Thus, in one aspect, compositions and methods useful for differentiating stem cells into a desired differentiated state are provided. To date, stem cells have typically been obtained by isolation from heterogeneous cell populations. For example, neural stem cells have been purified from the mammalian forebrain (Reynolds and Weiss, Science 255: 1707-1710, 1992) and these cells may be capable of differentiating into neurons, astrocytes, and oligodendrocytes. See, PCT publications WO 93/01275, WO 94/16718, WO 94/10292 and WO 94/09119. Hematopoietic stem cells have also been purified. See, U.S. Pat. Nos. 5,681,559 and 5,914, 108).

Once isolated, attempts have also been made to maintain stem cells in vitro, typically by altering the culture conditions. U.S. Pat. Nos. 6,265,175 and 5,980,885 describe how neural stem cells can be maintained in culture by varying culture conditions such as media components (e.g., serum, bFGF, EGF, amphiregulin, etc.) and vessel characteristics (e.g., adherency). In other methods, stem cells are selected for in culture by introducing a nucleic acid construct encoding an antibiotic resistance gene operably linked to a stem-cell specific promoter and then preferentially selecting stem cells in the presence of antibiotic. U.S. Pat. No. 6,146,888.

Similarly, differentiation of stem cells into a desired fate is generally accomplished by varying the culture environment and/or by varying the media components. In both cases, the yields are low and the procedures laborious and expensive. Therefore, using the compositions and methods described herein, one can readily and inexpensively obtain cells having the desired differentiation capabilities.

Thus, the methods and compositions disclosed herein allow both differentiation and dedifferentiation of cells, by employing a composition comprising one or more zinc finger proteins and/or associated proteins. Engineered zinc finger proteins that are capable of directing stem cells into a desired fate, either by affecting the stem cell via intrinsic signals, extrinsic signals or a combination of intrinsic and extrinsic signals are employed. The ZFPs can be engineered for their ability to regulate gene expression, for example by activating and/or inhibiting genes involved in differentiation. The disclosure also contemplates the use of combinations of ZFPs that modulate expression of one or more genes involved in propagation, development and differentiation.

The methods and compositions described herein also allow for increased ease and efficiency in obtaining cell populations having the desired characteristics. For example, the methods and compositions described herein can be used to cultivate any particular cell line; in cell therapy techniques (e.g., generation of islet-like cells for diabetes patients and neuronal cells for neurodegenerative diseases); in tissue engineering techniques (e.g., tissue repair, transplantation, etc.); detect changes in differentiation states of cells (e.g., DNA mutations, rearrangements, changes in chromatin structure, etc.); and gene therapy.

Thus, it will be apparent to one of skill in the art that ZFP(s) can be used facilitate the regulation of many processes involved in development and differentiation, including growth and self-renewal of stem cells; dedifferentiation; differentiation to a desired specialized cell type; and cloning.

Advantages of the presently-disclosed methods and compositions include, but are not limited to, (i) the ability to directly and specifically control core processes that direct stem cell differentiation (e.g., modulate expression of one or more genes, either by activating or repressing genes); (ii) the ability to reprogram stem cells ex vivo; (iii) the ability to generate all functional splice variants of the target protein; (iv) the ability to limit or eliminate uncontrolled massive overexpression of a target protein to toxic levels; (v) the ability to direct stem cell differentiation or dedifferentiation through epigenetic mechanisms; (vi) the ability to screen ZFP-TF libraries for ZFP-TFs that control differentiation, to identify additional genes that are important for stem cell differentiation; and (vii) the ability to generate animal models of ZFP-TF expression and in vivo regulation of stem cell differentiation.

General

Practice of the disclosed methods and use of the disclosed compositions employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

All patents, patent applications, and publications mentioned herein, whether supra or infra, are hereby incorporated by reference in their entirety.

DEFINITIONS

The terms "nucleic acid," "polynucleotide," and "oligonucleotide" are used interchangeably and refer to a deoxyribonucleotide or ribonucleotide polymer in either single- or double-stranded form. When not used to refer to a nucleic acid obtained from an organism, the term can encompass known analogues of natural nucleotides, as well as nucleotides that are modified in the base, sugar, and/or phosphate moieties.

The terms "totipotent" or "multipotent" refer to a cell in a developing cell mass such as, for example, an embryo or a fetus, that can potentially give rise to all of the cells in an adult organism. The term "multipotent" refers to a cell that can differentiate into many, but not all of the cell types of an adult organism. Certain stem cell populations can be derived from adult organisms while embryonic stem cells are derived from embryonic or fetal tissue. Embryonic stem cells are derived from a group of cells called the inner cell mass, which part of the blastocyst (4-5 days post fertilization in humans). A review of the state of stem cell research was published by NIH in June, 2001 and is available on the world-wide web at
http://www.nih.gov/news/stemcell/scireport.html.

The term "differentiation" refers to process(es) by which previously unspecialized cells become specialized for particular functions. In certain cases, cells may be undergo a stage of commitment or determination that precedes the onset of overt differentiation. Typically, cells of a committed or differentiated state express unique sets of the genes. Similarly, the term "dedifferentiation" refers to a reversal of differentiation, in which cells that have been committed and modified to fulfill a particular specialized function lose their specialized character and return to a relatively unspecialized structure and function. The terms are used to refer to any change or alteration in cellular differentiation state. Thus, dedifferentiation can refer to any reversal in differentiated state and does not imply that the cell must be reversed to a pluripotent state.

The teen "differentiated cell" refers to a cell that has developed from a relatively unspecialized phenotype to a more specialized phenotype. For example, a progenitor cell type such as a hematopoietic stem cell can give rise to a more differentiated cell such as a monocyte or an erythrocyte. The term "dedifferentiated cell" refers to a cell that had formerly attained a particular degree of differentiation, but has subsequently been immortalized or regained the ability to differentiate into one or more specialized cells (e.g., has become pluripotent or totipotent). It is highly unlikely that differentiated cells will revert into their precursor cells (e.g., dedifferentiate) in vivo or in vitro. However, using the method and compositions described herein, differentiated cells can be reprogrammed into immortalized, pluripotent or totipotent cells. Differentiated cells can be isolated from embryonic or somatic cells using techniques known in the art.

The terms "convert," "reprogram" and "dedifferentiate" are used interchangeably to refer to the phenomenon in which a differentiated cell becomes immortalized, pluripotent and/or totipotent. Cells can be dedifferentiated or converted to varying degrees. For example, it is possible that only a small portion of cells are converted or that an individual cell is reprogrammed to be pluripotent but not necessarily totipotent. Thus, the terms "converting," "reprogramming" or "dedifferentiating" compositions refer to compositions such as, for example, ZFPs that are able to dedifferentiate a target cell by actively remodeling chromatin and reversing binding of transcription factors.

A "binding protein" "or binding domain" is a protein or polypeptide that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger binding protein" is a protein or polypeptide that binds DNA, RNA and/or protein, preferably in a sequence-specific manner, as a result of stabilization of protein structure through coordination of a zinc ion. The term zinc finger binding protein is often abbreviated as zinc finger protein or ZFP. The individual DNA binding domains are typically referred to as "fingers." A ZFP has least one finger, typically two fingers, three fingers, or six fingers. Each finger binds from two to four base pairs of DNA, typically three or four base pairs of DNA. A ZFP binds to a nucleic acid sequence called a target site or target segment. Each finger typically comprises an approximately 30 amino acid, zinc-chelating, DNA-binding subdomain. An exemplary motif characterizing one class of these proteins ($C_2H_2$ class) is -Cys-$(X)_{2-4}$-Cys-$(X)_{12}$-His-$(X)_{3-5}$-His (where X is any amino acid). Studies have demonstrated that a single zinc finger of this class consists of an alpha helix containing the two invariant histidine residues co-ordinated with zinc along with the two cysteine residues of a single beta turn (see, e.g., Berg & Shi, *Science* 271:1081-1085 (1996)).

A "designed" zinc finger protein is a protein not occurring in nature whose structure and composition result principally from rational criteria. Rational criteria for design include application of substitution rules and computerized algorithms for processing information in a database storing information of existing ZFP designs and binding data, for example as described in co-owned PCT WO 00/42219. A "selected" zinc finger protein is a protein not found in nature whose production results primarily from an empirical process such as phage display. See e.g., U.S. Pat. No. 5,789,538; U.S. Pat. No. 6,007,988; U.S. Pat. No. 6,013,453; WO 95/19431; WO 96/06166 and WO 98/54311. An "engineered" zinc finger protein is a non-naturally occurring ZFP, for example a ZFP that has been either designed and/or selected.

A "gene," for the purposes of the present disclosure, includes a DNA region encoding a gene product (see infra), as well as all DNA regions that regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

A "target site" or "target sequence" is a sequence that is bound by a binding protein such as, for example, a ZFP. Target sequences can be nucleotide sequences (either DNA or RNA) or amino acid sequences. A single target site typically has about four to about ten base pairs. Typically, a two-fingered ZFP recognizes a four to seven base pair target site, a three-fingered ZFP recognizes a six to ten base pair target site, and a six fingered ZFP recognizes two adjacent nine to ten base pair target sites. By way of example, a DNA target sequence for a three-finger ZFP is generally either 9 or 10 nucleotides in length, depending upon the presence and/or nature of cross-strand interactions between the ZFP and the target sequence. Target sequences can be found in any DNA or RNA sequence, including regulatory sequences, exons, introns, or any non-coding sequence.

A "target subsite" or "subsite" is the portion of a DNA target site that is bound by a single zinc finger, excluding cross-strand interactions. Thus, in the absence of cross-strand interactions, a subsite is generally three nucleotides in length. In cases in which a cross-strand interaction occurs (e.g., a "D-able subsite," as described for example in co-owned PCT WO 00/42219, incorporated by reference in its entirety herein) a subsite is four nucleotides in length and overlaps with another 3- or 4-nucleotide subsite.

The term "naturally-occurring" is used to describe an object that can be found in nature, as distinct from being artificially produced by a human.

An "exogenous molecule" is a molecule that is not normally present in a cell, but can be introduced into a cell by one or more genetic, biochemical or other methods. Normal presence in the cell is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule. Thus, the term "exogenous regulatory molecule" refers to a molecule that can modulate gene expression in a target cell but which is not encoded by the cellular genome of the target cell.

An exogenous molecule can be, among other things, a small molecule, such as is generated by a combinatorial chemistry process, or a macromolecule such as a protein, nucleic acid, carbohydrate, lipid, glycoprotein, lipoprotien, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., protein or nucleic acid (e.g., an exogenous gene), providing it has a sequence that is different from an endogenous molecule. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (e.g., liposomes, including neutral and cationic lipids), electroporation, direct injection, cell fusion, particle bombardment, calcium phosphate co-precipitation, DEAE-dextran-mediated transfer and viral vector-mediated transfer.

By contrast, an "endogenous molecule" is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and components of chromatin remodeling complexes.

Thus, an "endogenous cellular gene" refers to a gene that is native to a cell, which is in its normal genomic and chromatin context, and which is not heterologous to the cell. Such cellular genes include, e.g., animal genes, plant genes, bacterial genes, protozoal genes, fungal genes, mitrochondrial genes, and chloroplastic genes.

An "endogenous gene" refers to a microbial or viral gene that is part of a naturally occurring microbial or viral genome in a microbially or virally infected cell. The microbial or viral genome can be extrachromosomal or integrated into the host chromosome. This term also encompasses endogenous cellular genes, as described above.

"Administering" an expression vector, nucleic acid, ZFP, or a delivery vehicle to a cell comprises transducing, transfecting, electroporating, translocating, fusing, phagocytosing, shooting or ballistic methods, etc., e.g., any means by which a protein or nucleic acid can be transported across a cell membrane and preferably into the nucleus of a cell.

The term "effective amount" includes that amount which results in the desired result, for example, deactivation of a previously activated gene, activation of a previously repressed gene, or inhibition of transcription of a structural gene or translation of RNA.

A "delivery vehicle" refers to a compound, e.g., a liposome, toxin, or a membrane translocation polypeptide, which is used to administer a ZFP. Delivery vehicles can also be used to administer nucleic acids encoding ZFPs, e.g., a lipid:nucleic acid complex, an expression vector, a virus, and the like.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of a mRNA. Gene products also include RNAs that are modified, by processes such as capping, polyadenylation, methylation, and editing, and proteins modified by, for example, methylation, acetylation, phosphorylation, ubiquitination, ADP-ribosylation, myristilation, and glycosylation.

"Gene activation" and "augmentation of gene expression" refer to any process that results in an increase in production of a gene product. A gene product can be either RNA (including, but not limited to, mRNA, rRNA, tRNA, and structural RNA) or protein. Accordingly, gene activation includes those processes that increase transcription of a gene and/or translation of a mRNA. Examples of gene activation processes which increase transcription include, but are not limited to, those which facilitate formation of a transcription initiation complex, those which increase transcription initiation rate, those which increase transcription elongation rate, those which increase processivity of transcription and those which relieve transcriptional repression (by, for example, blocking the binding of a transcriptional repressor). Gene activation can constitute, for example, inhibition of repression as well as stimulation of expression above an existing level. Examples of gene activation processes that increase translation include those that increase translational initiation, those that increase translational elongation and those that increase mRNA stability. In general, gene activation comprises any detectable increase in the production of a gene product, preferably an increase in production of a gene product by about 2-fold, more preferably from about 2- to about 5-fold or any integer therebetween, more preferably between about 5- and about 10-fold or any integer therebetween, more preferably between about 10- and about 20-fold or any integer therebetween, still more preferably between about 20- and about 50-fold or any integer therebetween, more preferably between about 50- and about 100-fold or any integer therebetween, more preferably 100-fold or more.

"Gene repression" and "inhibition of gene expression" refer to any process that results in a decrease in production of a gene product. A gene product can be either RNA (including, but not limited to, mRNA, rRNA, tRNA, and structural RNA) or protein. Accordingly, gene repression includes those processes that decrease transcription of a gene and/or translation of a mRNA. Examples of gene repression processes which decrease transcription include, but are not limited to, those which inhibit formation of a transcription initiation complex, those which decrease transcription initiation rate, those which decrease transcription elongation rate, those which decrease processivity of transcription and those which antagonize transcriptional activation (by, for example, blocking the binding of a transcriptional activator). Gene repression can constitute, for example, prevention of activation as well as inhibition of expression below an existing level. Examples of gene repression processes that decrease translation include those that decrease translational initiation, those that decrease translational elongation and those that decrease mRNA stability. Transcriptional repression includes both reversible and irreversible inactivation of gene transcription. In general, gene repression comprises any detectable decrease in the production of a gene product, preferably a decrease in production of a gene product by about 2-fold, more preferably from about 2- to about 5-fold or any integer therebetween, more preferably between about 5- and about 10-fold or any integer therebetween, more preferably between about 10- and about 20-fold or any integer therebetween, still more preferably between about 20- and about 50-fold or any integer therebetween, more preferably between about 50- and about 100-fold or any integer therebetween, more preferably 100-fold or more. Most preferably, gene repression results in complete inhibition of gene expression, such that no gene product is detectable.

"Eucaryotic cells" include, but are not limited to, fungal cells (such as yeast), plant cells, animal cells, mammalian cells and human cells.

The term "modulate" refers to a change in the quantity, degree or extent of a function. For example, the modified zinc finger-nucleotide binding polypeptides disclosed herein may modulate the activity of a promoter sequence by binding to a motif within the promoter, thereby inducing, enhancing or suppressing transcription of a gene operatively linked to the promoter sequence. Alternatively, modulation may include inhibition of transcription of a gene wherein the modified zinc finger-nucleotide binding polypeptide binds to the structural gene and blocks DNA dependent RNA polymerase from reading through the gene, thus inhibiting transcription of the gene. The structural gene may be a normal cellular gene or an oncogene, for example. Alternatively, modulation may include inhibition of translation of a transcript. Thus, "modulation" of gene expression includes both gene activation and gene repression.

Modulation of gene expression can be assayed by determining any parameter that is indirectly or directly affected by the expression of the target gene. Such parameters include, e.g., changes in RNA or protein levels; changes in protein activity; changes in product levels; changes in downstream gene expression; changes in transcription or activity of reporter genes such as, for example, luciferase, CAT, beta-galactosidase, or GFP (see, e.g., Mistili & Spector, (1997) Nature Biotechnology 15:961-964); changes in signal transduction; changes in phosphorylation and dephosphorylation; changes in receptor-ligand interactions; changes in concentrations of second messengers such as, for example, cGMP, cAMP, $IP_3$, and $Ca^{2+}$; changes in cell growth, changes in neovascularization, and/or changes in any functional effect of gene expression. Measurements can be made in vitro, in vivo, and/or ex vivo. Such functional effects can be measured by conventional methods, e.g., measurement of RNA or protein levels, measurement of RNA stability, and/or identification of downstream or reporter gene expression. Readout can be by way of, for example, chemiluminescence, fluorescence, colorimetric reactions, antibody binding, inducible markers, ligand binding assays; changes in intracellular second messengers such as cGMP and inositol triphosphate ($IP_3$); changes in intracellular calcium levels; cytokine release, and the like.

Accordingly, the terms "modulating expression" "inhibiting expression" and "activating expression" of a gene can refer to the ability of a molecule to activate or inhibit transcription of a gene. Activation includes prevention of transcriptional inhibition (e.g., prevention of repression of gene expression) and inhibition includes prevention of transcriptional activation (e.g., prevention of gene activation).

To determine the level of gene expression modulation by a ZFP, cells contacted with ZFPs are compared to control cells, e.g., without the zinc finger protein or with a non-specific ZFP, to examine the extent of inhibition or activation. Control samples are assigned a relative gene expression activity value of 100%. Modulation/inhibition of gene expression is achieved when the gene expression activity value relative to the control is about 80%, preferably 50% (e.g., 0.5× the activity of the control), more preferably 25%, more preferably 5-0%. Modulation/activation of gene expression is achieved when the gene expression activity value relative to the control is 110%, more preferably 150% (e.g., 1.5× the activity of the control), more preferably 200-500%, more preferably 1000-2000% or more.

A "promoter" is defined as an array of nucleic acid control sequences that direct transcription. As used herein, a promoter typically includes necessary nucleic acid sequences near the start site of transcription, such as, in the case of certain RNA polymerase II type promoters, a TATA element, enhancer, CCAAT box, SP-1 site, etc. As used herein, a promoter also optionally includes distal enhancer or repressor elements, which can be located as much as several thousand base pairs from the start site of transcription. The promoters often have an element that is responsive to transactivation by a DNA-binding moiety such as a polypeptide, e.g., a nuclear receptor, Gal4, the lac repressor and the like.

A "constitutive" promoter is a promoter that is active under most environmental and developmental conditions. An "inducible" promoter is a promoter that is active under certain environmental or developmental conditions.

A "weak promoter" refers to a promoter having about the same activity as a wild type herpes simplex virus ("HSV") thymidine kinase ("tk") promoter or a mutated HSV tk promoter, as described in Eisenberg & McKnight, Mol. Cell. Biol. 5:1940-1947 (1985).

A "transcriptional activator" and a "transcriptional repressor" refer to proteins or functional fragments of proteins that have the ability to modulate transcription, as described above. Such proteins include, e.g., transcription factors and co-factors (e.g., KRAB, MAD, ERD, SID, nuclear factor kappa B subunit p65, early growth response factor 1, and nuclear hormone receptors, VP16, VP64), endonucleases, integrases, recombinases, methyltransferases, histone acetyltransferases, histone deacetylases etc. Activators and repressors include co-activators and co-repressors (see, e.g., Utley et al., Nature 394:498-502 (1998)).

A "regulatory domain" or "functional domain" refers to a protein or a polypeptide sequence that has transcriptional modulation activity, or that is capable of interacting with proteins and/or protein domains that have transcriptional modulation activity. Typically, a functional domain is covalently or non-covalently linked to a DNA-binding domain (e.g., a ZFP) to modulate transcription of a gene of interest. Alternatively, a ZFP can act, in the absence of a functional domain, to modulate transcription. Furthermore, transcription of a gene of interest can be modulated by a ZFP linked to multiple functional domains.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one ore more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. See Ausubel et al., supra. The ability of a protein to interact with another protein can be determined, for example, by co-immunoprecipitation, two-hybrid assays or complementation, both genetic and biochemical. See, for example, Fields et al. (1989) Nature 340:245-246; U.S. Pat. No. 5,585,245 and PCT WO 98/44350.

A "fusion molecule" is a molecule in which two or more subunit molecules are linked, preferably covalently. The subunit molecules can be the same chemical type of molecule, or can be different chemical types of molecules. Examples of the first type of fusion molecule include, but are not limited to, fusion polypeptides (for example, a fusion between a ZFP DNA-binding domain and a transcriptional activation domain) and fusion nucleic acids (for example, a nucleic acid encoding the fusion polypeptide described herein). Examples of the second type of fusion molecule include, but are not limited to, a fusion between a triplex-forming nucleic acid and a polypeptide, and a fusion between a minor groove binder and a nucleic acid.

The term "heterologous" is a relative term, which when used with reference to portions of a nucleic acid indicates that the nucleic acid comprises two or more subsequences that are not found in the same relationship to each other in nature. For instance, a nucleic acid that is recombinantly produced typically has two or more sequences from unrelated genes synthetically arranged to make a new functional nucleic acid, e.g., a promoter from one source and a coding region from another source. The two nucleic acids are thus heterologous to each other in this context. When added to a cell, the recombinant nucleic acids would also be heterologous to the endogenous genes of the cell. Thus, in a chromosome, a heterologous nucleic acid would include an non-native (non-naturally occurring) nucleic acid that has integrated into the chromosome, or a non-native (non-naturally occurring) extrachromosomal nucleic acid. In contrast, a naturally translocated piece of chromosome would not be considered heterologous in the context of this patent application, as it comprises an endogenous nucleic acid sequence that is native to the mutated cell.

Similarly, a heterologous protein indicates that the protein comprises two or more subsequences that are not found in the same relationship to each other in nature (e.g., a "fusion protein," where the two subsequences are encoded by a single nucleic acid sequence). See, e.g., Ausubel, supra, for an introduction to recombinant techniques.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (naturally occurring) form of the cell or express a second copy of a native gene that is otherwise normally or abnormally expressed, under expressed or not expressed at all.

The terms "operative linkage" and "operatively linked" are used with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. An operatively linked transcriptional regulatory sequence is generally joined in cis with a coding sequence, but need not be directly adjacent to it. For example, an enhancer can constitute a transcriptional regulatory sequence that is operatively-linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a ZFP DNA-binding domain is fused to a transcriptional activation domain (or functional fragment thereof), the ZFP DNA-binding domain and the transcriptional activation domain (or functional fragment thereof) are in operative linkage if, in the fusion polypeptide, the ZFP DNA-binding domain portion is able to bind its target site and/or its binding site, while the transcriptional activation domain (or functional fragment thereof) is able to activate transcription.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one ore more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. See Ausubel et al., supra. The ability of a protein to interact with another protein can be determined, for example, by co-immunoprecipitation, two-hybrid assays or complementation, both genetic and biochemical. See, for example, Fields et al. (1989) *Nature* 340:245-246; U.S. Pat. No. 5,585,245 and PCT WO 98/44350.

The term "recombinant," when used with reference to a cell, indicates that the cell replicates an exogenous nucleic acid, or expresses a peptide or protein encoded by an exogenous nucleic acid. Recombinant cells can contain genes that are not found within the native (non-recombinant) form of the cell. Recombinant cells can also contain genes found in the native form of the cell wherein the genes are modified and re-introduced into the cell by artificial means. The term also encompasses cells that contain a nucleic acid endogenous to the cell that has been modified without removing the nucleic acid from the cell; such modifications include those obtained by gene replacement, site-specific mutation, and related techniques.

A "recombinant expression cassette" or simply an "expression cassette" is a nucleic acid construct, generated recombinantly or synthetically, that has control elements that are capable of effecting expression of a structural gene that is operatively linked to the control elements in hosts compatible with such sequences. Expression cassettes include at least promoters and optionally, transcription termination signals. Typically, the recombinant expression cassette includes at least a nucleic acid to be transcribed (e.g., a nucleic acid encoding a desired polypeptide) and a promoter. Additional factors necessary or helpful in effecting expression can also be used as described herein. For example, an expression cassette can also include nucleotide sequences that encode a signal sequence that directs secretion of an expressed protein from the host cell. Transcription termination signals, enhancers, and other nucleic acid sequences that influence gene expression can also be included in an expression cassette.

The term "naturally occurring," as applied to an object, means that the object can be found in nature.

The terms "polypeptide," "peptide" and "protein" are used interchangeably to refer to a polymer of amino acid residues. The term also applies to amino acid polymers in which one or more amino acids are chemical analogues of a corresponding naturally-occurring amino acids.

A "subsequence" or "segment" when used in reference to a nucleic acid or polypeptide refers to a sequence of nucleotides or amino acids that comprise a part of a longer sequence of nucleotides or amino acids (e.g., a polypeptide), respectively.

As used herein, the term "small molecule" is a non-protein based moiety including, but not limited to the following: (i) molecules typically less than 10 K molecular weight; (ii) molecules that are permeable to cells; (iii) molecules that are less susceptible to degradation by many cellular mechanisms than peptides or oligonucleotides; and/or (iv) molecules that generally do not elicit an immune response. Many pharmaceutical companies have extensive libraries of chemical and/or biological mixtures, often fungal, bacterial, or algal extracts, that would be desirable to screen with the assays disclosed herein. Small molecules may be either biological or synthetic organic compounds, or even inorganic compounds (e.g., cisplatin).

DNA Binding Proteins

Disclosed herein are methods and compositions for modulating and controlling stem cell differentiation using DNA binding proteins. In certain embodiments, the DNA binding protein comprises a zinc finger protein (ZFP). The engineering of novel DNA binding proteins that selectively regulate the expression of a gene at its endogenous locus (i.e., genes as they occur in the context of their natural chromosomal structure) has been described. See, for example, WO 00/41566 and WO 00/42219, the disclosures of which are incorporated by reference herein in their entireties. This approach provides a unique capacity to selectively turn on or turn off endogenous gene expression in the cell and thus affect fundamental mechanisms determining stem cell fate.

Thus, the ZFPs disclosed herein are engineered to recognize a selected target site in the endogenous gene of choice. Typically, a backbone from any suitable $C_2H_2$ ZFP, such as SP-1, SP-1C, or ZIF268, is used as the scaffold for the engineered ZFP (see, e.g., Jacobs, *EMBO J.* 11:4507 (1992); Desjarlais & Berg, *PNAS* 90:2256-2260 (1993)). A number of methods can then be used to design and/or select a ZFP with high affinity for its target (e.g., preferably with a $K_d$ of less than about 25 nM). As described above, a ZFP can be designed or selected to bind to any suitable target site in the target endogenous gene, with high affinity. Co-owned PCT WO 00/42219, herein incorporated by reference in its entirety, comprehensively describes methods for design, construction, and expression of ZFPs for selected target sites.

Any suitable method known in the art can be used to design and construct nucleic acids encoding ZFPs, e.g., phage display, random mutagenesis, combinatorial libraries, computer/rational design, affinity selection, PCR, cloning from cDNA or genomic libraries, synthetic construction and the like. (see, e.g., U.S. Pat. No. 5,786,538; Wu et al., *PNAS* 92:344-348 (1995); Jamieson et al., *Biochemistry* 33:5689-5695 (1994); Rebar & Pabo, *Science* 263:671-673 (1994); Choo & Klug, *PNAS* 91:11163-11167 (1994); Choo & Klug, *PNAS* 91: 11168-11172 (1994); Desjarlais & Berg, *PNAS* 90:2256-2260 (1993); Desjarlais & Berg, *PNAS* 89:7345-7349 (1992); Pomerantz et al., *Science* 267:93-96 (1995); Pomerantz et al., *PNAS* 92:9752-9756 (1995); Liu et al., *PNAS* 94:5525-5530 (1997); Griesman & Pabo, *Science* 275:657-661 (1997); Desjarlais & Berg, *PNAS* 91:11-99-11103 (1994)). A preferred method is described in co-owned PCT WO 00/42219.

Thus, these methods work by selecting a target gene, and systematically searching within the possible subsequences of the gene for target sites, as described, e.g., in co-owned U.S. Pat. No. 6,453,242. In some such methods, every possible subsequence of 9 or 10 contiguous bases on either strand of a potential target gene is evaluated to determine whether it contains putative target sites, e.g., D-able sites, see U.S. Pat. No. 6,453,242. Typically, such a comparison is performed by computer, and a list of target sites is output. Optionally, such target sites can be output in different subsets according to how many D-able sites are present. It will be apparent that these principles can be extended to select target sites to be bound by ZFPs with any number of component fingers. For example, a suitable target site for a nine finger protein would have three component segments.

The target sites identified by the above methods can be subject to further evaluation by other criteria or can be used directly for design or selection (if needed) and production of a ZFP specific for such a site. A further criterion for evaluating potential target sites is their proximity to particular regions within a gene. If a ZFP is to be used to repress a cellular gene on its own (e.g., without linking the ZFP to a repressing moiety), then the optimal location appears to be at, or within 50 bp upstream or downstream of the site of transcription initiation, to interfere with the formation of the transcription complex (Kim & Pabo, *J. Biol. Chem.* 272: 29795-296800 (1997)) or compete for an essential enhancer binding protein. If, however, a ZFP is fused to a functional domain such as the KRAB repressor domain or the VP16 activator domain, the location of the binding site is considerably more flexible and can be outside known regulatory regions. For example, a KRAB domain can repress transcription at a promoter up to at least 3 kbp from where KRAB is bound (Margolin et al., *PNAS* 91:4509-4513 (1994)). Thus, target sites can be selected that do not necessarily include or overlap segments of demonstrable biological significance with target genes, such as regulatory sequences. Other criteria for further evaluating target segments include the prior availability of ZFPs binding to such segments or related segments, and/or ease of designing new ZFPs to bind a given target segment.

After a target segment has been selected, a ZFP that binds to the segment can be provided by a variety of approaches. The simplest of approaches is to provide a precharacterized ZFP from an existing collection that is already known to bind to the target site. However, in many instances, such ZFPs do not exist. An alternative approach can also be used to design new ZFPs, which uses the information in a database of existing ZFPs and their respective binding affinities. A further approach is to design a ZFP based on substitution rules. See, e.g., WO 96/06166; WO 98/53058; WO 98/53059 and WO 98/53060. A still further alternative is to select a ZFP with specificity for a given target by an empirical process such as phage display. See, e.g., WO 98/53057. In some such methods, each component finger of a ZFP is designed or selected independently of other component fingers. For example, each finger can be obtained from a different preexisting ZFP or each finger can be subject to separate randomization and selection.

Once a ZFP has been selected, designed, or otherwise provided to a given target segment, the ZFP (or the DNA encoding it) is synthesized. Exemplary methods for synthesizing and expressing DNA encoding zinc finger proteins are described below. The ZFP or a polynucleotide encoding it can then be used for modulation of expression, or analysis of the target gene containing the target site to which the ZFP binds.

Expression and Purification of ZFPs

ZFP polypeptides and nucleic acids can be made using routine techniques in the field of recombinant genetics. Basic texts disclosing the general methods of use in the field include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)). In addition, essentially any nucleic acid can be custom ordered from any of a variety of commercial sources. Similarly, peptides and antibodies can be custom ordered from any of a variety of commercial sources.

Two alternative methods are typically used to create the coding sequences required to express newly designed DNA-binding peptides. One protocol is a PCR-based assembly procedure that utilizes six overlapping oligonucleotides (FIG. 1). Three oligonucleotides (oligos 1, 3, and 5 in FIG. 1) correspond to "universal" sequences that encode portions of the DNA-binding domain between the recognition helices. These oligonucleotides remain constant for all zinc finger constructs. The other three "specific" oligonucleotides (oligos 2, 4, and 6 in FIG. 1) are designed to encode the recognition helices. These oligonucleotides contain substitutions primarily at positions −1, 2, 3 and 6 on the recognition helices making them specific for each of the different DNA-binding domains.

The PCR synthesis is carried out in two steps. First, a double stranded DNA template is created by combining the six oligonucleotides (three universal, three specific) in a four cycle PCR reaction with a low temperature annealing step, thereby annealing the oligonucleotides to form a DNA "scaffold." The gaps in the scaffold are filled in by high-fidelity thermostable polymerase, the combination of Taq and Pfu polymerases also suffices. In the second phase of construction, the zinc finger template is amplified by external primers designed to incorporate restriction sites at either end for cloning into a shuttle vector or directly into an expression vector.

An alternative method of cloning the newly designed DNA-binding proteins relies on annealing complementary oligonucleotides encoding the specific regions of the desired ZFP. This particular application requires that the oligonucleotides be phosphorylated prior to the final ligation step. This is usually performed before setting up the annealing reactions, but kinasing can also occur post-annealing. In brief, the "universal" oligonucleotides encoding the constant regions of the proteins (oligos 1, 2 and 3 of above) are annealed with their complementary oligonucleotides. Additionally, the "specific" oligonucleotides encoding the finger recognition helices are annealed with their respective complementary oligonucleotides. These complementary oligos are designed to fill in the region that was previously filled in by polymerase in the protocol described above. The complementary oligos to the common oligos 1 and finger 3 are engineered to leave overhanging sequences specific for the restriction sites used in cloning into the vector of choice. The second assembly protocol differs from the initial protocol in the following aspects: the "scaffold" encoding the newly designed ZFP is composed entirely of synthetic DNA thereby eliminating the polymerase fill-in step, additionally the fragment to be cloned into the vector does not require amplification. Lastly, the design of leaving sequence-specific overhangs eliminates the need for restriction enzyme digests of the inserting fragment.

The resulting fragment encoding the newly designed ZFP is ligated into an expression vector. Expression vectors that are commonly utilized include, but are not limited to, a modified pMAL-c2 bacterial expression vector (New England BioLabs, "NEB") or a eukaryotic expression vector, pcDNA (Promega).

Any suitable method of protein purification known to those of skill in the art can be used to purify ZFPs (see Ausubel, supra, Sambrook, supra). In addition, any suitable host can be used, e.g., bacterial cells, insect cells, yeast cells, mammalian cells, and the like.

In one embodiment, expression of the ZFP fused to a maltose binding protein (MBP-ZFP) in bacterial strain JM109 allows for straightforward purification through an amylose column (NEB). High expression levels of the zinc finger chimeric protein can be obtained by induction with IPTG since the MBP-ZFP fusion in the pMal-c2 expression plasmid is under the control of the IPTG inducible tac promoter (NEB). Bacteria containing the MBP-ZFP fusion plasmids are inoculated in to 2×YT medium containing 10 µM $ZnCl_2$, 0.02% glucose, plus 50 µg/ml ampicillin and shaken at 37° C. At mid-exponential growth IPTG is added to 0.3 mM and the cultures are allowed to shake. After 3 hours the bacteria are harvested by centrifugation, disrupted by sonication, and then insoluble material is removed by centrifugation. The MBP-ZFP proteins are captured on an amylose-bound resin, washed extensively with buffer containing 20 mM Tris-HCl (pH 7.5), 200 mM NaCl, 5 mM DTT and 50 µM $ZnCl_2$, then eluted with maltose in essentially the same buffer (purification is based on a standard protocol from NEB). Purified proteins are quantitated and stored for biochemical analysis.

The biochemical properties of the purified proteins, e.g., $K_d$, can be characterized by any suitable assay. In one embodiment, $K_d$ is characterized via electrophoretic mobility shift assays ("EMSA") (Buratowski & Chodosh, in Current Protocols in Molecular Biology pp. 12.2.1-12.2.7 (Ausubel ed., 1996); see also U.S. Pat. No. 5,789,538, co-owned PCT WO 00/42219 herein incorporated by reference in its entirety, and Example 1). Affinity is measured by titrating purified protein against a low fixed amount of labeled double-stranded oligonucleotide target. The target comprises the natural binding site sequence (9 or 18 bp) flanked by the 3 bp found in the natural sequence. External to the binding site plus flanking sequence is a constant sequence. The annealed oligonucleotide targets possess a 1 bp 5' overhang that allows for efficient labeling of the target with T4 phage polynucleotide kinase. For the assay the target is added at a concentration of 40 nM or lower (the actual concentration is kept at least 10-fold lower than the lowest protein dilution) and the reaction is allowed to equilibrate for at least 45 min. In addition the reaction mixture also contains 10 mM Tris (pH 7.5), 100 mM KCl, 1 mM $MgCl_2$, 0.1 mM $ZnCl_2$, 5 mM DTT, 10% glycerol, 0.02% BSA (poly (dIdC) or (dAdT) (Pharmacia) can also added at 10-100 µg/µl).

The equilibrated reactions are loaded onto a 10% polyacrylamide gel, which has been pre-run for 45 min in Tris/glycine buffer, then bound and unbound labeled target is resolved be electrophoresis at 150V (alternatively, 10-20% gradient Tris-HCl gels, containing a 4% polyacrylamide stacker, can be used). The dried gels are visualized by autoradiography or phosphoroimaging and the apparent $K_d$ is determined by calculating the protein concentration that gives half-maximal binding.

Similar assays can also include determining active fractions in the protein preparations. Active fractions are determined by stoichiometric gel shifts where proteins are titrated against a high concentration of target DNA. Titrations are done at 100, 50, and 25% of target (usually at micromolar levels).

In another embodiment, phage display libraries can be used to select ZFPs with high affinity to the selected target site. This method differs fundamentally from direct design in that it involves the generation of diverse libraries of mutagenized ZFPs, followed by the isolation of proteins with desired DNA-binding properties using affinity selection methods. To use this method, the experimenter typically proceeds as follows.

First, a gene for a ZFP is mutagenized to introduce diversity into regions important for binding specificity and/or affinity. In a typical application, this is accomplished via randomization of a single finger at positions −1, +2, +3, and +6, and perhaps accessory positions such as +1, +5, +8, or +10.

Next, the mutagenized gene is cloned into a phage or phagemid vector as a fusion with, e.g., gene III of filamentous phage, which encodes the coat protein pIII. The zinc finger gene is inserted between segments of gene III encoding the membrane export signal peptide and the remainder of pIII, so that the ZFP is expressed as an amino-terminal fusion with pIII in the mature, processed protein. When using phagemid vectors, the mutagenized zinc finger gene may also be fused to a truncated version of gene III encoding, minimally, the C-terminal region required for assembly of pIII into the phage particle.

The resultant vector library is transformed into *E. coli* and used to produce filamentous phage that express variant ZFPs on their surface as fusions with the coat protein pIII (if a phagemid vector is used, then the this step requires superinfection with helper phage). The phage library is then incubated with target DNA site, and affinity selection methods are used to isolate phage that bind target with high affinity from bulk phage. Typically, the DNA target is immobilized on a solid support, which is then washed under conditions sufficient to remove all but the tightest binding phage. After washing, any phage remaining on the support are recovered via elution under conditions that totally disrupt zinc finger-DNA binding.

Recovered phage are used to infect fresh *E. coli*, which is then amplified and used to produce a new batch of phage particles. The binding and recovery steps are then repeated as many times as is necessary to sufficiently enrich the phage pool for tight binders such that these may be identified using sequencing and/or screening methods.

Regulatory Domains

Binding domains (e.g., ZFPs) can optionally be associated with regulatory domains (e.g., functional domains) for modulation of gene expression. The ZFP can be covalently or non-covalently associated with one or more regulatory domains, alternatively two or more regulatory domains, with the two or more domains being two copies of the same domain, or two different domains. The regulatory domains can be covalently linked to the ZFP, e.g., via an amino acid linker, as part of a fusion protein. The ZFPs can also be associated with a regulatory domain via a non-covalent dimerization domain, e.g., a leucine zipper, a STAT protein N terminal domain, or an FK506 binding protein (see, e.g., O'Shea, *Science* 254: 539 (1991), Barahmand-Pour et al., *Curr. Top. Microbiol. Immunol.* 211:121-128 (1996); Klemm et al., *Annu. Rev. Immunol.* 16:569-592 (1998); Klemm et al., *Annu. Rev. Immunol.* 16:569-592 (1998); Ho et al., *Nature* 382:822-826 (1996); and Pomeranz et al., *Biochem.* 37:965 (1998)). The regulatory domain can be associated with the ZFP at any suitable position, including the C- or N-terminus of the ZFP.

Common regulatory domains for addition to the ZFP include, e.g., effector domains from transcription factors (activators, repressors, co-activators, co-repressors), silencers, nuclear hormone receptors, oncogene transcription factors (e.g., myc, jun, fos, myb, max, mad, rel, ets, bcl, myb, mos family members etc.); DNA repair enzymes and their associated factors and modifiers; DNA rearrangement enzymes and their associated factors and modifiers; chromatin associated proteins and their modifiers (e.g., kinases, acetylases and deacetylases); and DNA modifying enzymes (e.g., methyltransferases, topoisomerases, helicases, ligases, kinases, phosphatases, polymerases, endonucleases) and their associated factors and modifiers.

Transcription factor polypeptides from which one can obtain a regulatory domain include those that are involved in regulated and basal transcription. Such polypeptides include transcription factors, their effector domains, coactivators, silencers, nuclear hormone receptors (see, e.g., Goodrich et al., *Cell* 84:825-30 (1996) for a review of proteins and nucleic acid elements involved in transcription; transcription factors in general are reviewed in Barnes & Adcock, *Clin. Exp. Allergy* 25 Suppl. 2:46-9 (1995) and Roeder, *Methods Enzymol.* 273:165-71 (1996)). Databases dedicated to transcription factors are known (see, e.g., *Science* 269:630 (1995)). Nuclear hormone receptor transcription factors are described in, for example, Rosen et al., *J. Med. Chem.* 38:4855-74 (1995). The C/EBP family of transcription factors are reviewed in Wedel et al., *Immunobiology* 193:171-85 (1995). Coactivators and co-repressors that mediate transcription regulation by nuclear hormone receptors are reviewed in, for example, Meier, *Eur. J. Endocrinol.* 134 (2):158-9 (1996); Kaiser et al., *Trends Biochem. Sci.* 21:342-5 (1996); and Utley et al., *Nature* 394:498-502 (1998)). GATA transcription factors, which are involved in regulation of hematopoiesis, are described in, for example, Simon, *Nat. Genet.* 11:9-11 (1995); Weiss et al., *Exp. Hematol.* 23:99-107. TATA box binding protein (TBP) and its associated TAF polypeptides (which include TAF30, TAF55, TAF80, TAF110, TAF150, and TAF250) are described in Goodrich & Tijan, *Curr. Opin. Cell Biol.* 6:403-9 (1994) and Hurley, *Curr. Opin. Struct. Biol.* 6:69-75 (1996). The STAT family of transcription factors are reviewed in, for example, Barahmand-Pour et al., *Curr. Top. Microbiol. Immunol.* 211:121-8 (1996). Transcription factors involved in disease are reviewed in Aso et al., *J. Clin. Invest.* 97:1561-9 (1996).

In one embodiment, the KRAB repression domain from the human KOX-1 protein is used as a transcriptional repressor (Thiesen et al., *New Biologist* 2:363-374 (1990); Margolin et al., *PNAS* 91:4509-4513 (1994); Pengue et al., *Nucl. Acids Res.* 22:2908-2914 (1994); Witzgall et al., *PNAS* 91:4514-4518 (1994)). In another embodiment, KAP-1, a KRAB co-repressor, is used with KRAB (Friedman et al., *Genes Dev.* 10:2067-2078 (1996)). Alternatively, KAP-1 can be used alone with a ZFP. Other preferred transcription factors and transcription factor domains that act as transcriptional repressors include MAD (see, e.g., Sommer et al., *J. Biol. Chem.* 273:6632-6642 (1998); Gupta et al., *Oncogene* 16:1149-1159 (1998); Queva et al., *Oncogene* 16:967-977 (1998); Larsson et al., *Oncogene* 15:737-748 (1997); Laherty et al., *Cell* 89:349-356 (1997); and Cultraro et al., *Mol Cell. Biol.* 17:2353-2359 (19977)); FKHR (forkhead in rhapdosarcoma gene; Ginsberg et al., *Cancer Res.* 15:3542-3546 (1998); Epstein et al., *Mol. Cell. Biol.* 18:4118-4130 (1998)); EGR-1 (early growth response gene product-1; Yan et al., *PNAS* 95:8298-8303 (1998); and Liu et al., *Cancer Gene Ther.* 5:3-28 (1998)); the ets2 repressor factor repressor domain (ERD; Sgouras et al., *EMBO J.* 14:4781-4793 ((19095)); and the MAD smSIN3 interaction domain (SID; Ayer et al., *Mol. Cell. Biol.* 16:5772-5781 (1996)).

In one embodiment, the HSV VP16 activation domain is used as a transcriptional activator (see, e.g., Hagmann et al., *J. Virol.* 71:5952-5962 (1997)). Other preferred transcription factors that could supply activation domains include the VP64 activation domain (Seipel et al., *EMBO J.* 11:4961-4968 (1996)); nuclear hormone receptors (see, e.g., Torchia et al., *Curr. Opin. Cell. Biol.* 10:373-383 (1998)); the p65 subunit of nuclear factor kappa B (Bitko & Batik, *J. Virol.* 72:5610-5618 (1998) and Doyle & Hunt, *Neuroreport* 8:2937-2942 (1997)); and EGR-1 (early growth response gene product-1; Yan et al., *PNAS* 95:8298-8303 (1998); and Liu et al., *Cancer Gene Ther.* 5:3-28 (1998)).

Kinases, phosphatases, and other proteins that modify polypeptides involved in gene regulation are also useful as regulatory domains for ZFPs. Such modifiers are often involved in switching on or off transcription mediated by, for example, hormones. Kinases involved in transcription regulation are reviewed in Davis, *Mol. Reprod. Dev.* 42:459-67 (1995), Jackson et al., *Adv. Second Messenger Phosphoprotein Res.* 28:279-86 (1993), and Boulikas, *Crit. Rev. Eukaryot. Gene Expr.* 5:1-77 (1995), while phosphatases are reviewed in, for example, Schonthal & Semin, *Cancer Biol.* 6:239-48 (1995). Nuclear tyrosine kinases are described in Wang, *Trends Biochem. Sci.* 19:373-6 (1994).

As described, useful domains can also be obtained from the gene products of oncogenes (e.g., myc, jun, fos, myb, max, mad, rel, ets, bcl, myb, mos family members) and their associated factors and modifiers. Oncogenes are described in, for example, Cooper, *Oncogenes,* 2nd ed., The Jones and Bartlett Series in Biology, Boston, Mass., Jones and Bartlett Publishers, 1995. The ets transcription factors are reviewed in Waslylk et al., *Eur. J. Biochem.* 211:7-18 (1993) and Crepieux et al., *Crit. Rev. Oncog.* 5:615-38 (1994). Myc oncogenes are reviewed in, for example, Ryan et al., *Biochem. J.* 314:713-21 (1996). The jun and fos transcription factors are described in, for example, *The Fos and Jun Families of Transcription Factors*, Angel & Herrlich, eds. (1994). The max oncogene is reviewed in Hurlin et al., Cold Spring Harb. Symp. Quant. Biol. 59:109-16. The myb gene family is reviewed in Kanei-Ishii et al., *Curr. Top. Microbiol. Immunol.* 211:89-98 (1996). The mos family is reviewed in Yew et al., *Curr. Opin. Genet. Dev.* 3:19-25 (1993).

ZFPs can include regulatory domains obtained from DNA repair enzymes and their associated factors and modifiers. DNA repair systems are reviewed in, for example, Vos, *Curr. Opin. Cell Biol.* 4:385-95 (1992); Sancar, *Ann. Rev. Genet.* 29:69-105, (1995); Lehmann, *Genet. Eng.* 17:1-19 (1995); and Wood, *Ann. Rev. Biochem.* 65:135-67 (1996). DNA rearrangement enzymes and their associated factors and modifiers can also be used as regulatory domains (see, e.g., Gangloff et al., *Experientia* 50:261-9 (1994); Sadowski, *FASEB J.* 7:760-7 (1993)).

Similarly, regulatory domains can be derived from DNA modifying enzymes (e.g., DNA methyltransferases, topoisomerases, helicases, ligases, kinases, phosphatases, polymerases) and their associated factors and modifiers. Helicases are reviewed in Matson et al., *Bioessays,* 16:13-22 (1994), and methyltransferases are described in Cheng, *Curr. Opin. Struct. Biol.* 5:4-10 (1995). Chromatin associated proteins and their modifiers (e.g., kinases, acetylases and deacetylases), such as histone deacetylase (Wolffe, *Science* 272:371-2 (1996)) are also useful as domains for addition to the ZFP of choice. In one preferred embodiment, the regulatory domain is a DNA methyl transferase that acts as a transcriptional repressor (see, e.g., Van den Wyngaert et al., *FEBS Lett.* 426:283-289 (1998); Flynn et al., *J. Mol. Biol.* 279:101-116 (1998); Okano et al., *Nucleic Acids Res.* 26:2536-2540 (1998); and Zardo & Caiafa, *J. Biol. Chem.* 273:16517-16520 (1998)). In another preferred embodiment, endonucleases such as Fok1 are used as transcriptional repressors, which act via gene cleavage (see, e.g., WO95/09233; and PCT/US94/01201).

Factors that control chromatin and DNA structure, movement and localization and their associated factors and modifiers; factors derived from microbes (e.g., prokaryotes, eukaryotes and virus) and factors that associate with or modify them can also be used to obtain chimeric proteins. In one embodiment, recombinases and integrases are used as regulatory domains. In one embodiment, histone acetyltransferase is used as a transcriptional activator (see, e.g., Jin & Scotto, *Mol. Cell. Biol.* 18:4377-4384 (1998); Wolffe, *Science* 272:371-372 (1996); Taunton et al., *Science* 272: 408-411 (1996); and Hassig et al., *PNAS* 95:3519-3524 (1998)). In another embodiment, histone deacetylase is used as a transcriptional repressor (see, e.g., Jin & Scotto, *Mol. Cell. Biol.* 18:4377-4384 (1998); Syntichaki & Thireos, *J. Biol. Chem.* 273:24414-24419 (1998); Sakaguchi et al., *Genes Dev.* 12:2831-2841 (1998); and Martinez et al., *J. Biol. Chem.* 273:23781-23785 (1998)).

Another suitable repression domain is methyl binding domain protein 2B (MBD-2B) (see, also Hendrich et al. (1999) *Mamm Genome* 10:906-912 for description of MBD proteins). Another useful repression domain is that associated with the v-ErbA protein (see infra). See, for example, Damm, et al. (1989) *Nature* 339:593-597; Evans (1989) *Int. J. Cancer Suppl.* 4:26-28; Pain et al. (1990) *New Biol.* 2:284-294; Sap et al. (1989) *Nature* 340:242-244; Zenke et al. (1988) *Cell* 52:107-119; and Zenke et al. (1990) *Cell* 61:1035-1049. Additional exemplary repression domains include, but are not limited to, thyroid hormone receptor (TR, see infra), SID, MBD1, MBD2, MBD3, MBD4, MBD-like proteins, members of the DNMT family (e.g., DNMT1, DNMT3A, DNMT3B), Rb, MeCP1 and MeCP2. See, for example, Bird et al. (1999) *Cell* 99:451-454; Tyler et al. (1999) *Cell* 99:443-446; Knoepfler et al. (1999) *Cell* 99:447-450; and Robertson et al. (2000) *Nature Genet.* 25:338-342. Additional exemplary repression domains include, but are not limited to, ROM2 and AtHD2A. See, for example, Chern et al. (1996) *Plant Cell* 8:305-321; and Wu et al. (2000) *Plant J.* 22:19-27.

Certain members of the nuclear hormone receptor (MAR) superfamily, including, for example, thyroid hormone receptors (TRs) and retinoic acid receptors (RARs) are among the most potent transcriptional regulators currently known. Zhang et al., *Annu. Rev. Physiol.* 62:439-466 (2000) and Sucov et al., *Mol Neurobiol* 10(2-3):169-184 (1995). In the absence of their cognate ligand, these proteins bind with high specificity and affinity to short stretches of DNA (e.g., 12-17 base pairs) within regulatory loci (e.g., enhancers and promoters) and effect robust transcriptional repression of adjacent genes. The potency of their regulatory action stems from the concurrent use of two distinct functional pathways to drive gene silencing: (i) the creation of a localized domain of repressive chromatin via the targeting of a complex between the corepressor N-CoR and a histone deacetylase, HDAC3 (Guenther et al., *Genes Dev* 14:1048-1057 (2000); Urnov et al., *EMBO J* 19:4074-4090 (2000); Li et al., *EMBO J* 19, 4342-4350 (2000) and Underhill et al., *J. Biol. Chem.* 275:40463-40470 (2000)) and (ii) a chromatin-independent pathway (Urnov et al., supra) that may involve direct interference with the function of the basal transcription machinery (Fondell et al., *Genes Dev* 7(7B):1400-1410 (1993) and Fondell et al., *Mol Cell Biol* 16:281-287 (1996).

In the presence of very low (e.g., nanomolar) concentrations of their ligand, these receptors undergo a conformational change that leads to the release of corepressors, recruitment of a different class of auxiliary molecules (e.g., coactivators) and potent transcriptional activation. Collingwood et al., *J. Mol. Endocrinol.* 23(3):255-275 (1999).

The portion of the receptor protein responsible for transcriptional control (e.g., repression and activation) can be physically separated from the portion responsible for DNA binding, and retains full functionality when tethered to other polypeptides, for example, other DNA-binding domains. Accordingly, a nuclear hormone receptor transcription control domain can be fused to a ZFP DNA-binding domain such that the transcriptional regulatory activity of the receptor can be targeted to a chromosomal region of interest (e.g., a gene) by virtue of the ZFP binding domain.

Moreover, the structure of TR and other nuclear hormone receptors can be altered, either naturally or through recombinant techniques, such that it loses all capacity to respond to hormone (thus losing its ability to drive transcriptional activation), but retains the ability to effect transcriptional repression. This approach is exemplified by the transcriptional regulatory properties of the oncoprotein v-ErbA. The v-ErbA protein is one of the two proteins required for leukemic transformation of immature red blood cell precursors in young chicks by the avian erythroblastosis virus. TR is a major regulator of erythropoiesis (Beug et al., *Biochim Biophys Acta* 1288(3):M35-47 (1996); in particular, in its unliganded state, it represses genes required for cell cycle arrest and the differentiated state. Thus, the administration of thyroid hormone to immature erythroblasts leads to their rapid differentiation. The v-ErbA oncoprotein is an extensively mutated version of TR; these mutations include: (i) deletion of 12 amino-terminal amino acids; (ii) fusion to the gag oncoprotein; (iii) several point mutations in the DNA binding domain that alter the DNA binding specificity of the protein relative to its parent, TR, and impair its ability to heterodimerize with the retinoid X receptor; (iv) multiple point mutations in the ligand-binding domain of the protein that effectively eliminate the capacity to bind thyroid hormone; and (v) a deletion of a carboxy-terminal stretch of amino acids that is essential for transcriptional activation. Stunnenberg et al., *Biochim Biophys Acta* 1423(1):F15-33 (1999). As a consequence of these mutations, v-ErbA retains the capacity to bind to naturally occurring TR target genes and is an effective transcriptional repressor when bound (Urnov et al., supra; Sap et al., *Nature* 340:242-244 (1989); and Ciana et al., *EMBO J.* 17(24):7382-7394 (1999). In contrast to TR, however, v-ErbA is completely insensitive to thyroid hormone, and thus maintains transcriptional repression in the face of a challenge from any concentration of thyroids or retinoids, whether endogenous to the medium, or added by the investigator (4).

We have previously demonstrated that this functional property of v-ErbA is retained when its repression domain is fused to a heterologous, synthetic DNA binding domain. Accordingly, in one aspect, v-ErbA or its functional fragments are used as a repression domain. In additional embodiments, TR or its functional domains are used as a repression domain in the absence of ligand and/or as an activation domain in the presence of ligand (e.g., 3,5,3'-triiodo-L-thyronine or T3). Thus, TR can be used as a switchable functional domain (e.g., a bifunctional domain); its activity (activation or repression) being dependent upon the presence or absence (respectively) of ligand.

Additional exemplary repression domains are obtained from the DAX protein and its functional fragments. Zazopoulos et al., *Nature* 390:311-315 (1997). In particular, the C-terminal portion of DAX-1, including amino acids 245-470, has been shown to possess repression activity. Altincicek et al., *J. Biol. Chem.* 275:7662-7667 (2000). A further exemplary repression domain is the RBP1 protein and its functional fragments. Lai et al., *Oncogene* 18:2091-2100 (1999); Lai et al., *Mol. Cell. Biol.* 19:6632-6641 (1999); Lai et al., *Mol. Cell. Biol.* 21:2918-2932 (2001) and WO 01/04296. The full-length RBP1 polypeptide contains 1257 amino acids. Exemplary functional fragments of RBP1 are a polypeptide comprising amino acids 1114-1257, and a polypeptide comprising amino acids 243-452.

Members of the TIEG family of transcription factors contain three repression domains known as R1, R2 and R3. Repression by TIEG family proteins is achieved at least in part through recruitment of mSIN3A histone deacetylases complexes. Cook et al. (1999) *J. Biol. Chem.* 274:29,500-29,504; Zhang et al. (2001) *Mol. Cell. Biol.* 21:5041-5049. Any or all of these repression domains (or their functional fragments) can be fused alone, or in combination with additional repression domains (or their functional fragments), to a DNA-binding domain to generate a targeted exogenous repressor molecule.

Furthermore, the product of the human cytomegalovirus (HCMV) UL34 open reading frame acts as a transcriptional repressor of certain HCMV genes, for example, the US3 gene. LaPierre et al. (2001) *J. Virol.* 75:6062-6069. Accordingly, the UL34 gene product, or functional fragments thereof, can be used as a component of a fusion polypeptide also comprising a zinc finger binding domain. Nucleic acids encoding such fusions are also useful in the methods and compositions disclosed herein.

Yet another exemplary repression domain is the CDF-1 transcription factor and/or its functional fragments. See, for example, WO 99/27092.

The Ikaros family of proteins are involved in the regulation of lymphocyte development, at least in part by transcriptional repression. Accordingly, an Ikaros family member (e.g., Ikaros, Aiolos) or a functional fragment thereof, can be used as a repression domain See, for example, Sabbattini et al. (2001) *EMBO J.* 20:2812-2822.

The yeast Ashlp protein comprises a transcriptional repression domain. Maxon et al. (2001) *Proc. Natl. Acad. Sci. USA* 98:1495-1500. Accordingly, the Ashlp protein, its functional fragments, and homologues of Ashlp, such as those found, for example, in, vertebrate, mammalian, and plant cells, can serve as a repression domain for use in the methods and compositions disclosed herein.

Additional exemplary repression domains include those derived from histone deacetylases (HDACs, e.g., Class I HDACs, Class II HDACs, SIR-2 homologues), HDAC-interacting proteins (e.g., SIN3, SAP30, SAP15, NCoR, SMRT, RB, p107, p130, RBAP46/48, MTA, Mi-2, Brg1, Brm), DNA-cytosine methyltransferases (e.g., Dnmt1, Dnmt3a, Dnmt3b), proteins that bind methylated DNA (e.g., MBD1, MBD2, MBD3, MBD4, MeCP2, DMAP1), protein methyltransferases (e.g., lysine and arginine methylases, SuVar homologues such as Suv39H1), polycomb-type repressors (e.g., Bmi-1, eed1, RING1, RYBP, E2F6, Mel18, YY1 and CtBP), viral repressors (e.g., adenovirus E1b 55K protein, cytomegalovirus UL34 protein, viral oncogenes such as v-erbA), hormone receptors (e.g., Dax-1, estrogen receptor, thyroid hormone receptor), and repression domains associated with naturally-occurring zinc finger proteins (e.g., WT1, KAP1). Further exemplary repression domains include members of the polycomb complex and their homologues, HPH1, HPH2, HPC2, NC2, groucho, Eve, tramtrak, mHP1, SIP1, ZEB1, ZEB2, and Enx1/Ezh2. In all of these cases, either the full-length protein or a functional fragment can be used as a repression domain for fusion to a zinc finger binding domain. Furthermore, any homologues of the aforementioned proteins can also be used as repression domains, as can proteins (or their functional fragments) that interact with any of the aforementioned proteins.

Additional repression domains, and exemplary functional fragments, are as follows. Hes1 is a human homologue of the *Drosophila hairy* gene product and comprises a functional fragment encompassing amino acids 910-1014. In particular, a WRPW (trp-arg-pro-trp) motif can act as a repression domain. Fisher et al. (1996) *Mol. Cell. Biol.* 16:2670-2677.

The TLE1, TLE2 and TLE3 proteins are human homologues of the *Drosophila groucho* gene product. Functional fragments of these proteins possessing repression activity reside between amino acids 1-400. Fisher et al., supra.

The Tbx3 protein possesses a functional repression domain between amino acids 524-721. He et al. (1999) *Proc. Natl. Acad. Sci. USA* 96:10,212-10,217. The Tbx2 gene product is involved in repression of the p14/p16 genes and contains a region between amino acids 504-702 that is homologous to the repression domain of Tbx3; accordingly Tbx2 and/or this functional fragment can be used as a repression domain. Carreira et al. (1998) *Mol. Cell. Biol.* 18:5,099-5,108.

The human Ezh2 protein is a homologue of *Drosophila* enhancer of zeste and recruits the eed1 polycomb-type repressor. A region of the Ezh2 protein comprising amino acids 1-193 can interact with eed1 and repress transcription; accordingly Ezh2 and/or this functional fragment can be used as a repression domain. Denisenko et al. (1998) *Mol. Cell. Biol.* 18:5634-5642.

The RYBP protein is a corepressor that interacts with polycomb complex members and with the YY1 transcription factor. A region of RYBP comprising amino acids 42-208 has been identified as functional repression domain. Garcia et al. (1999) *EMBO J.* 18:3404-3418.

The RING finger protein RING1A is a member of two different vertebrate polycomb-type complexes, contains multiple binding sites for various components of the polycomb complex, and possesses transcriptional repression activity. Accordingly, RING1A or its functional fragments can serve as a repression domain. Satjin et al. (1997) *Mol. Cell. Biol.* 17:4105-4113.

The Bmi-1 protein is a member of a vertebrate polycomb complex and is involved in transcriptional silencing. It contains multiple binding sites for various polycomb complex components. Accordingly, Bmi-1 and its functional fragments are useful as repression domains. Gunster et al. (1997) *Mol. Cell. Biol.* 17:2326-2335; Hemenway et al. (1998) *Oncogene* 16:2541-2547.

The E2F6 protein is a member of the mammalian Bmi-1-containing polycomb complex and is a transcriptional repressor that is capable or recruiting RYBP, Bmi-1 and RING1A. A functional fragment of E2F6 comprising amino acids 129-281 acts as a transcriptional repression domain. Accordingly, E2F6 and its functional fragments can be used as repression domains Trimarchi et al. (2001) *Proc Natl. Acad. Sci. USA* 98:1519-1524.

The eed1 protein represses transcription at least in part through recruitment of histone deacetylases (e.g., HDAC2). Repression activity resides in both the N- and C-terminal regions of the protein. Accordingly, eed1 and its functional fragments can be used as repression domains. van der Vlag et al. (1999) *Nature Genet.* 23:474-478.

The CTBP2 protein represses transcription at least in part through recruitment of an HPC2-polycomb complex. Accordingly, CTBP2 and its functional fragments are useful as repression domains Richard et al. (1999) *Mol. Cell. Biol.* 19:777-787.

Neuron-restrictive silencer factors are proteins that repress expression of neuron-specific genes. Accordingly, a NRSF or functional fragment thereof can serve as a repression domain See, for example, U.S. Pat. No. 6,270,990.

It will be clear to those of skill in the art that, in the formation of a fusion protein (or a nucleic acid encoding same) between a zinc finger binding domain and a functional domain, either a repressor or a molecule that interacts with a repressor is suitable as a functional domain. Essentially any molecule capable of recruiting a repressive complex and/or repressive activity (such as, for example, histone deacetylation) to the target gene is useful as a repression domain of a fusion protein.

Additional exemplary activation domains include, but are not limited to, p300, CBP, PCAF, SRC1 PvALF, AtHD2A and ERF-2. See, for example, Robyr et al. (2000) Mol. Endocrinol. 14:329-347; Collingwood et al. (1999) J. Mol. Endocrinol. 23:255-275; Leo et al. (2000) Gene 245:1-11; Manteuffel-Cymborowska (1999) Acta Biochim. Pol. 46:77-89; McKenna et al. (1999) J. Steroid Biochem. Mol. Biol. 69:3-12; Malik et al. (2000) Trends Biochem. Sci. 25:277-283; and Lemon et al. (1999) Curr. Opin. Genet. Dev. 9:499-504. Additional exemplary activation domains include, but are not limited to, OsGAI, HALF-1, C1, AP1, ARF-5, -6, -7, and -8, CPRF1, CPRF4, MYC-RP/GP, and TRAB1. See, for example, Ogawa et al. (2000) Gene 245:21-29; Okanami et al. (1996) Genes Cells 1:87-99; Goff et al. (1991) Genes Dev. 5:298-309; Cho et al. (1999) Plant Mol. Biol. 40:419-429; Ulmason et al. (1999) Proc. Natl. Acad. Sci. USA 96:5844-5849; Sprenger-Haussels et al. (2000) Plant J. 22:1-8; Gong et al. (1999) Plant Mol. Biol. 41:33-44; and Hobo et al. (1999) Proc. Natl. Acad. Sci. USA 96:15, 348-15, 353.

It will be clear to those of skill in the art that, in the formation of a fusion protein (or a nucleic acid encoding same) between a zinc finger binding domain and a functional domain, either an activator or a molecule that interacts with an activator is suitable as a functional domain Essentially any molecule capable of recruiting an activating complex and/or activating activity (such as, for example, histone acetylation) to the target gene is useful as an activating domain of a fusion protein.

Insulator domains, chromatin remodeling proteins such as ISWI-containing domains and/or methyl binding domain proteins suitable for use as functional domains in fusion molecules are described, for example, in co-owned PCT application US01/40616 and co-owned U.S. Patent applications 60/236,409; 60/236,884; and 60/253,678.

In a further embodiment, a DNA-binding domain (e.g., a zinc finger domain) is fused to a bifunctional domain (BFD). A bifunctional domain is a transcriptional regulatory domain whose activity depends upon interaction of the BFD with a second molecule. The second molecule can be any type of molecule capable of influencing the functional properties of the BFD including, but not limited to, a compound, a small molecule, a peptide, a protein, a polysaccharide or a nucleic acid. An exemplary BFD is the ligand binding domain of the estrogen receptor (ER). In the presence of estradiol, the ER ligand binding domain acts as a transcriptional activator; while, in the absence of estradiol and the presence of tamoxifen or 4-hydroxy-tamoxifen, it acts as a transcriptional repressor. Another example of a BFD is the thyroid hormone receptor (TR) ligand binding domain which, in the absence of ligand, acts as a transcriptional repressor and in the presence of thyroid hormone (T3), acts as a transcriptional activator. An additional BFD is the glucocorticoid receptor (GR) ligand binding domain. In the presence of dexamethasone, this domain acts as a transcriptional activator; while, in the presence of RU486, it acts as a transcriptional repressor. An additional exemplary BFD is the ligand binding domain of the retinoic acid receptor. In the presence of its ligand all-trans-retinoic acid, the retinoic acid receptor recruits a number of co-activator complexes and activates transcription. In the absence of ligand, the retinoic acid receptor is not capable of recruiting transcriptional co-activators. Additional BFDs are known to those of skill in the art. See, for example, U.S. Pat. Nos. 5,834,266 and 5,994,313 and PCT WO 99/10508.

Linker domains between polypeptide domains, e.g., between two ZFPs or between a ZFP and a regulatory domain, can be included. Such linkers are typically polypeptide sequences, such as poly gly sequences of between about 5 and 200 amino acids. Preferred linkers are typically flexible amino acid subsequences which are synthesized as part of a recombinant fusion protein. For example, in one embodiment, the linker DGGGS is used to link two ZFPs. In another embodiment, the flexible linker linking two ZFPs is an amino acid subsequence comprising the sequence TGEKP (see, e.g., Liu et al., PNAS 5525-5530 (1997)). In another embodiment, the linker LRQKDGERP is used to link two ZFPs. In another embodiment, the following linkers are used to link two ZFPs: GGRR (Pomerantz et al. 1995, supra), $(G4S)_n$ (Kim et al., PNAS 93, 1156-1160 (1996.); and GGRRGGGS; LRQRDGERP; LRQKDGGGSERP; LRQKd$(G3S)_2$ ERP. Alternatively, flexible linkers can be rationally designed using computer program capable of modeling both DNA-binding sites and the peptides themselves (Desjarlais & Berg, PNAS 90:2256-2260 (1993), PNAS 91:11099-11103 (1994) or by phage display methods.

In other embodiments, a chemical linker is used to connect synthetically or recombinantly produced domain sequences. Such flexible linkers are known to persons of skill in the art. For example, poly(ethylene glycol) linkers are available from Shearwater Polymers, Inc. Huntsville, Ala. These linkers optionally have amide linkages, sulfhydryl linkages, or heterofunctional linkages. In addition to covalent linkage of ZFPs to regulatory domains, non-covalent methods can be used to produce molecules with ZFPs associated with regulatory domains.

In addition to regulatory domains, often the ZFP is expressed as a fusion protein such as maltose binding protein ("MBP"), glutathione S transferase (GST), hexahistidine, c-myc, and the FLAG epitope, for ease of purification, monitoring expression, or monitoring cellular and subcellular localization.

Identification

One or more the following techniques can be used to identify and/or characterize ZFPs suitable for use in the presently disclosed methods and compositions:

(i) DNA Sequencing: relevant genomic DNA sequence (human and mouse) for a target gene (whose expression is to be regulated) are identified. (See, also, exemplary target genes discussed below). Typically, approximately 1-2 kilobases of sequence on either side of the transcription initiation site is obtained. Sequences may be available from public databases, or can be cloned from genomic DNA and sequenced according to techniques that are well known in the art. The transcription initiation site of each gene may also be identified, for example, using 5'-RACE;

(ii) DNaseI hypersensitivity mapping may be optionally employed, for example to characterize the chromatin structure in the promoter regions of the target genes (e.g., in mouse ES cells and/or human embryonic and adult stem cells). Parallel DNaseI mapping may be performed in immortalized mouse and human cell lines (e.g., MES13 and HEK293, respectively), which serve as useful models in which to validate and optimize DNaseI mapping probes, and to screen ZFP-TFs for their capacity to regulate target gene expression (prior to performing these analyses in stem cells);

(iii) Design of ZFPs: ZFP-TFs that selectively bind to sites in the target gene(s) (e.g., DNaseI accessible regions) are designed following the teachings herein. The effectiveness of the ZFP-TFs in regulating gene expression is determined, for example by introducing them, or by transfecting polynucleotides encoding them, into the immortalized cell lines and measuring mRNA expression from the target gene by real-time PCR (e.g., TaqMan®). Different transcription regulatory domains may be tested on each ZFP to optimize activity. ZFPs may be designed as mimics of "decision-making" transcription factors, e.g., Gli, which is acted upon by sonic hedgehog (Shh), known positive regulators of SC proliferation ex vivo. See, e.g., Bhardwaj et al. Nat Immunol 2001, 2:172-180; Villavicencio et al. Am J Hum Genet 2000, 67:1047-1054. For instance, a ZFP may be designed as a "Gli-3 mimic" to prevent or reduce the activation of the Gli-1 promoter by Shh/Gli-3;

(iv) ZFP-TFs that have been validated in the immortalized cell lines are preferably then tested in stem cells. Plasmids that express the ZFP-TFs are delivered to the cells, e.g., by electroporation. Other delivery options that offer certain advantages (e.g., placing the ZFP-TF under an inducible promoter for controlled expression) can also be used. As with the immortalized cell lines, the ability of ZFP-TFs to regulate gene expression in stem cells is measured, for example, using RT-PCR analysis (Taqman); and (v) the effects on cellular differentiation can also be examined, for example, by analyzing the pattern of expressed markers of cell type (such as those exemplified in Table 1) using established in vitro differentiation protocols as described in the art and herein. One or more cytokines (and/or other factors) that induce differentiation may also be included.

Alternatively, an exemplary method for identifying genes important for lineage specification is to introduce a ZFP-TF library in mouse ES cells, to screen for ZFPs that promote differentiation towards specific cell lineages. A set of mouse ES cell lines, in which the β-galactosidase marker gene has been inserted into individual mouse genes that are specifically expressed in certain cell types and tissues, including those of lymphoid lineage, have been described. See, for example, Mitchell et al. (2001) Nature Genetics 28:241-249; Tate et al. (1998) J. Cell. Sci. 111:2575-2585; and Meth. Enzymology 328:592-615 (2000). Such cell lines can be used to screen large numbers of ZFP-TFs, to identify those ZFPs that regulate, for example, lymphoid and myeloid differentiation. ZFP-TF function can be scored by either the staining of cells for β-galactosidase expression, or by assessment of morphological and phenotypic changes associated with differentiation. This type of screen allows the generation of 500 cell lines per month, with each cell line expressing a single engineered ZFP-TF. This, in turn, allows for the identification of ZFP-TFs—and their respective target genes—that are responsible for controlling differentiation of mouse ES cells into specific lineages, e.g., immune cell lineages. The results of such screens are likely to be readily transferable to human adult stem cells because promoter sequences are highly conserved across species.

Target Genes

The ZFPs described herein can be developed to target one or more genes that may be involved in stem cell differentiation, dedifferentiation, proliferation and/or self-renewal. Suitable targets for regulation by ZFPs in order to dedifferentiate and/or maintain self-renewing stem cell cultures include, but are not limited to, one or more of the genes shown in Tables 1 and 2.

Additionally, other genes involved in differentiation can also be targeted. For example, in hematopoietic stem cells, ZFPs can be targeted to repress the genes encoding E1A, EBF, Pax-5 (which is anticipated to result in a robust proliferation of B-lymphocyte precursor cells); SCL/Tal-1, AML-1 or c-Myb (which is anticipated to result in a robust proliferation of myeloid and/or erythroid lineages); and TCF-1 (which is anticipated to result in a robust proliferation of T-cells). As shown in Table 1, liver stem cells are known express certain proteins, for example OV6 and/or a cytokeratin such as cytokeratin 19. (See, U.S. Pat. No. 6,129,911). Expression of the GATA4 gene in embryonic stem cells promotes differentiation into extraembryonic endoderm.

Other suitable targets may include HoxB4, which drives differentiation of embryonic stem cells into the early stage hematopoietic lineage and is a strong positive regulator of hematopoietic stem cell expansion, and confers lymphoid-myeloid engraftment potential (see, e.g., Helgason et al. *Blood* 87, 2740-9. (1996); Sauvageau, G. et al. *Genes Dev* 9, 1753-65. (1995); Antonchuk et al. *Cell* 109, 39-45 (2002); Kyba et al. *Cell* 109, 29-37 (2002); Oct-3/4, which seems to play a role in controlling embryonic and adult stem cell phenotype (see, e.g., Niwa et al. *Nat Genet* 24, 372-6. (2000); Nichols, J. et al. *Cell* 95, 379-91. (1998); GCNF; Bcrp1; Sox-2; genes that promote B cell differentiation such as XBP-1, PAX5/BSAP, and Blimp-1, and those that promote NK or T cell development include CBF-α2 and GATA-3. (See, e.g., Reimold et al. *Nature* 412, 300-7. (2001); Hagman et al. *Curr Top Microbiol Immunol* 245, 169-94 (2000); Angelin-Duclos et al. *J Immunol* 165, 5462-71. (2000); Telfer et al. *Dev Biol* 229, 363-82. (2001); Nawijn et al. *J Immunol* 167, 724-32. (2001).

Oct-4, for example, is known to be required for totipotency in mice and is likely required for it in humans. See, e.g., Nichols et al. *Cell* 1998, 95:379-391; Hansis et al. *Mol Hum Reprod* 2000, 6:999-1004. The Oct-4 promoter has been characterized. See, e.g., Nordhoff et al. *Mamm Genome* 2001, 12:309-317. Conditional upregulation and downregulation from a transgene yields a well-characterized array of phenotypes. See, Niwa et al. *Nat Genet* 2000, 24:372-376. Similarly, another target for the ZFPs described herein may be HES-1, a bHLH transcriptional repressor that is activated by the Notch pathway and is required for maintenance of proliferation of neuronal precursors, presumably by repressing the p21 gene. Castella et al. *Mol Cell Biol* 2000, 20:6170-6183; Solecki et al. *Neuron* 2001, 31:557-568.

Other gene targets for modulation by ZFPs include cytokines or other growth factors. For example, self-renewal of many stem cells, particularly non-human ES cells, is promoted by cytokines such as leukemia inhibitory factor (LIF). (See, U.S. Pat. No. 5,187,077). Other non-limiting examples of genes encoding cytokines which may be targeted (alone or in combination) using the methods and compositions described interleukin-2 (IL-2) (Morgan et al. (1976) *Science* 193:1007-1008); stem cell factor (SCF); interleukin 3 (IL-3); interleukin 6 (IL-6) (Brankenhoff et al. (1987) *Immunol.* 139:4116-4121); interleukin 12 (IL-12); G-CSF; granulocyte macrophage-colony stimulating factor (GM-CSF); interleukin-1 alpha (IL-1α); interleukin-11 (IL-11); MIP-1α; c-kit ligand, thrombopoietin (TPO); CD40 ligand (CD40L) (Spriggs et al., (1992) *J. Exp. Med.* 176:1543-1550 and Armitage et al. (1992) *Nature* 357:80-82); tumor necrosis factor-related activation-induced cytokine (TRANCE) (Wong et al. (1997) *J Biol Chem* 272(40):25190-4); tumor necrosis factors (e.g., TNF-alpha, Spriggs (1992) *Immunol Ser.* 56:3-34); and flt3 ligand (flt-3L) (Lyman et al. (1995) *Oncogene* 11(6):1165-72). Growth factors involved in differentiation and self-renewal capabilities include, but are not limited to, EGF, amphiregulin, fibroblast growth factor and transforming growth factor alpha. (See, e.g., Reynolds and Weiss (1992) *Science*, 255:1707; U.S. Pat. No. 6,265,175 and U.S. Pat. No. 5,851,832).

Still other gene targets for modulation by ZFPs include secreted factors that instruct cells to differentiate or to remain dedifferentiated. Non-limiting examples of secreted factors include, the highly conserved family of proteins that includes TGFbeta and Wnt regulate transcription of proteins such as beta-cadherin. In *Drosophila*, DPP (a homologue of Bmp2/4) is required to maintain female germ line stem cells and, to promote cell division. Notch and related proteins also act in various organisms in the development of sensory organ systems.

Genes whose protein products are involved in cell-cell interactions can also be targeted for modulation by the ZFPs described herein in order to control the differentiation and culture of cells. For example, integrins are a large family of proteins that mediate, among other things, adhesion of cells to the extracellular matrix. Molecules that form potential targets also include laminin, demosomal glycoproteins such as demoplakin I, cell adhesion molecules such as liver cell adhesion molecule LCAM, carcinoembryoni antigen (CEA), dipeptidyl peptidase-4. (See, U.S. Pat. No. 6,129,911). It will be readily apparent in view of the teachings herein that other genes can also be targeted, alone or in various combinations and that such targets can be readily determined using standard techniques.

Many of the products of these and other suitable target, genes are intracellular proteins and therefore their levels could not be significantly increased simply by addition of exogenous sources of the proteins to the culture medium. The compositions and methods described herein allow for the independent control of expression of any target gene(s) from within the cells to direct stem cell differentiation towards specific immune lineages.

Table 1 summarizes markers commonly used to identify stem cells and to characterize differentiated cell types arising from these cells.

TABLE 1

Markers Commonly Used to Identify Stem Cells and to Characterize Differentiated Cell Types

| Marker Name | Cell Type | Significance |
|---|---|---|
| Blood Vessel | | |
| Fetal liver kinase-1 (Flk1) | Endothelial | Cell-surface receptor protein that identifies endothelial cell progenitor; marker of cell-cell contacts |
| Smooth muscle cell-specific myosin heavy chain | Smooth muscle | Identifies smooth muscle cells in the wall of blood vessels |
| Vascular endothelial cell cadherin | Smooth muscle | Identifies smooth muscle cells in the wall of blood vessels |
| Bone | | |
| Bone-specific alkaline phosphatase (BAP) | Osteoblast | Enzyme expressed in osteoblast; activity indicates bone formation |
| Hydroxyapatite | Osteoblast | Mineralized bone matrix that provides structural integrity; marker of bone formation |

TABLE 1-continued

Markers Commonly Used to Identify Stem Cells and to Characterize Differentiated Cell Types

| Marker Name | Cell Type | Significance |
|---|---|---|
| Osteocalcin (OC) | Osteoblast | Mineral-binding protein uniquely synthesized by osteoblast; marker of bone formation |
| Bone Marrow and Blood | | |
| Bone morphogenetic protein receptor (BMPR) | Mesenchymal stem and progenitor cells | Important for the differentiation of committed mesenchymal cell types from mesenchymal stem and progenitor cells; BMPR identifies early mesenchymal lineages (stem and progenitor cells) |
| CD4 and CD8 | White blood cell (WBC) | Cell-surface protein markers specific for mature T lymphocyte (WBC subtype) |
| CD34 | Hematopoietic stem cell (HSC), satellite, endothelial progenitor | Cell-surface protein on bone marrow cell, indicative of a HSC and endothelial progenitor; CD34 also identifies muscle satellite, a muscle stem cell |
| CD34 + Sca1 + Lin- profile | Mesenchymal stem cell (MSC) | Identifies MSCs, which can differentiate into adipocyte, osteocyte, chondrocyte, and myocyte |
| CD38 | Absent on HSC Present on WBC lineages | Cell-surface molecule that identifies WBC lineages. Selection of CD34+/CD38− cells allows for purification of HSC populations |
| CD44 | Mesenchymal | A type of cell-adhesion molecule used to identify specific types of mesenchymal cells |
| c-Kit | HSC, MSC | Cell-surface receptor on BM cell types that identifies HSC and MSC; binding by fetal calf serum (FCS) enhances proliferation of ES cells, HSCs, MSCs, and hematopoietic progenitor cells |
| Colony-forming unit (CFU) | HSC, MSC progenitor | CFU assay detects the ability of a single stem cell or progenitor cell to give rise to one or more cell lineages, such as red blood cell (RBC) and/or white blood cell (WBC) lineages |
| Fibroblast colony-forming unit (CFU-F) | Bone marrow fibroblast | An individual bone marrow cell that has given rise to a colony of multipotent fibroblast cells; such identified cells are precursors of differentiated mesenchymal lineages |
| Hoechst dye | Absent on HSC | Fluorescent dye that binds DNA; HSC extrudes the dye and stains lightly compared with other cell types |
| Leukocyte common antigen (CD45) | WBC | Cell-surface protein on WBC progenitor |
| Lineage surface antigen (Lin) | HSC, MSC Differentiated RBC and WBC lineages | Thirteen to 14 different cell-surface proteins that are markers of mature blood cell lineages; detection of Lin-negative cells assists in the purification of HSC and hematopoietic progenitor populations |
| Mac-1 | WBC | Cell-surface protein specific for mature granulocyte and macrophage (WBC subtypes) |
| Muc-18 (CD146) | Bone marrow fibroblasts, endothelial | Cell-surface protein (immunoglobulin superfamily) found on bone marrow fibroblasts, which may be important in hematopoiesis; a subpopulation of Muc-18+ cells are mesenchymal precursors |
| Stem cell antigen (Sca-1) | HSC, MSC | Cell-surface protein on bone marrow (BM) cell, indicative of HSC and MSC |
| Stro-1 antigen | Stromal (mesenchymal) precursor cells, hematopoietic cells | Cell-surface glycoprotein on subsets of bone marrow stromal (mesenchymal) cells; selection of Stro-1+ cells assists in isolating mesenchymal precursor cells, which are multipotent cells that give rise to adipocytes, osteocytes, smooth myocytes, fibroblasts, chondrocytes, and blood cells |
| Thy-1 | HSC, MSC | Cell-surface protein; negative or low detection is suggestive of HSC |
| Cartilage | | |
| Collagen types II and IV | Chondrocyte | Structural proteins produces specifically by chondrocyte |
| Keratin | Keratinocyte | Principal protein of skin; identifies differentiated keratinocyte |
| Sulfated proteoglycan | Chondrocyte | Molecule found in connective tissues; synthesized by chondrocyte |
| Fat | | |
| Adipocyte lipid-binding protein (ALBP) | Adipocyte | Lipid-binding protein located specifically in adipocyte |
| Fatty acid transporter (FAT) | Adipocyte | Transport molecule located specifically in adipocyte |
| Adipocyte lipid-binding protein (ALBP) | Adipocyte | Lipid-binding protein located specifically in adipocyte |
| General | | |
| Y chromosome | Male cells | Male-specific chromosome used in labeling and detecting donor cells in female transplant recipients |
| Karyotype | Most cell types | Analysis of chromosome structure and number in a cell |
| Liver | | |
| Albumin | Hepatocyte | Principal protein produced by the liver; indicates functioning of maturing and fully differentiated hepatocytes |
| B-1 integrin | Hepatocyte | Cell-adhesion molecule important in cell-cell interactions; marker expressed during development of liver |
| Nervous System | | |
| CD133 | Neural stem cell, HSC | Cell-surface protein that identifies neural stem cells, which give rise to neurons and glial cells |
| Glial fibrillary acidic protein (GFAP) | Astrocyte | Protein specifically produced by astrocyte |
| Microtubule-associated protein-2 (MAP-2) | Neuron | Dendrite-specific MAP; protein found specifically in dendritic branching of neuron |
| Myelin basic protein (MPB) | Oligo-dendrocyte | Protein produced by mature oligodendrocytes; located in the myelin sheath surrounding neuronal structures |

TABLE 1-continued

Markers Commonly Used to Identify Stem Cells and to Characterize Differentiated Cell Types

| Marker Name | Cell Type | Significance |
|---|---|---|
| Nestin | Neural progenitor | Intermediate filament structural protein expressed in primitive neural tissue |
| Neural tubulin | Neuron | Important structural protein for neuron; identifies differentiated neuron |
| Neurofilament (NF) | Neuron | Important structural protein for neuron; identifies differentiated neuron |
| Neurosphere | Embryoid body (EB), ES | Cluster of primitive neural cells in culture of differentiating ES cells; indicates presence of early neurons and glia |
| Noggin | Neuron | A neuron-specific gene expressed during the development of neurons |
| O4 | Oligo-dendrocyte | Cell-surface marker on immature, developing oligodendrocyte |
| O1 | Oligo-dendrocyte | Cell-surface marker that characterizes mature oligodendrocyte |
| Synaptophysin | Neuron | Neuronal protein located in synapses; indicates connections between neurons |
| Tau | Neuron | Type of MAP; helps maintain structure of the axon |
| Pancreas | | |
| Cytokeratin 19 (CK19) | Pancreatic epithelium | CK19 identifies specific pancreatic epithelial cells that are progenitors for islet cells and ductal cells |
| Glucagon | Pancreatic islet | Expressed by alpha-islet cell of pancreas |
| Insulin | Pancreatic islet | Expressed by beta-islet cell of pancreas |
| Insulin-promoting factor-1 (PDX-1) | Pancreatic islet | Transcription factor expressed by beta-islet cell of pancreas |
| Nestin | Pancreatic progenitor | Structural filament protein indicative of progenitor cell lines including pancreatic |
| Pancreatic polypeptide | Pancreatic islet | Expressed by gamma-islet cell of pancreas |
| Somatostatin | Pancreatic islet | Expressed by delta-islet cell of pancreas |
| Pluripotent Stem Cells | | |
| Alkaline phosphatase | Embryonic stem (ES), embryonal carcinoma (EC) | Elevated expression of this enzyme is associated with undifferentiated pluripotent stem cell (PSC) |
| Alpha-fetoprotein (AFP) | Endoderm | Protein expressed during development of primitive endoderm; reflects endodermal differentiation |
| Bone morphogenetic protein-4 | Mesoderm | Growth and differentiation factor expressed during early mesoderm formation and differentiation |
| Brachyury | Mesoderm | Transcription factor important in the earliest phases of mesoderm formation and differentiation; used as the earliest indicator of mesoderm formation |
| Cluster designation 30 (CD30) | ES, EC | Surface receptor molecule found specifically on PSC |
| Cripto (TDGF-1) | ES, cardio-myocyte | Gene for growth factor expressed by ES cells, primitive ectoderm, and developing cardiomyocyte |
| GATA-4 gene | Endoderm | Expression increases as ES differentiates into endoderm |
| GCTM-2 | ES, EC | Antibody to a specific extracellular-matrix molecule that is synthesized by undifferentiated PSCs |
| Genesis | ES, EC | Transcription factor uniquely expressed by ES cells either in or during the undifferentiated state of PSCs |
| Germ cell nuclear factor | ES, EC | Transcription factor expressed by PSCs |
| Hepatocyte Nuclear factor-4 (HNF-4) | Endoderm | Transcription factor expressed early in endoderm formation |
| Nestin | Ectoderm, neural and pancreatic progenitor | Intermediate filaments within cells; characteristic of primitive neuroectoderm formation |
| Neuronal cell-adhesion molecule (N-CAM) | Ectoderm | Cell-surface molecule that promotes cell-cell interaction; indicates primitive neuroectoderm formation |
| Oct-4 | ES, EC | Transcription factor unique to PSCs; essential for establishment and maintenance of undifferentiated PSCs |
| Pax6 | Ectoderm | Transcription factor expressed as ES cell differentiates into neuroepithelium |
| Stage-specific embryonic antigen-3 (SSEA-3) | ES, EC | Glycoprotein specifically expressed in early embryonic development and by undifferentiated PSCs |
| Stage-specific embryonic antigen-4 (SSEA-4) | ES, EC | Glycoprotein specifically expressed in early embryonic development and by undifferentiated PSCs |
| Stem cell factor (SCF or c-Kit ligand) | ES, EC, HSC, MSC | Membrane protein that enhances proliferation of ES and EC cells, hematopoietic stem cell (HSCs), and mesenchymal stem cells (MSCs); binds the receptor c-Kit |
| Telomerase | ES, EC | An enzyme uniquely associated with immortal cell lines; useful for identifying undifferentiated PSCs |
| TRA-1-60 | ES, EC | Antibody to a specific extracellular matrix molecule is synthesized by undifferentiated PSCs |
| TRA-1-81 | ES, EC | Antibody to a specific extracellular matrix molecule normally synthesized by undifferentiated PSCs |
| Vimentin | Ectoderm, neural and pancreatic progenitor | Intermediate filaments within cells; characteristic of primitive neuroectoderm formation |
| Skeletal Muscle/Cardiac/Smooth Muscle | | |
| MyoD and Pax7 | Myoblast, myocyte | Transcription factors that direct differentiation of myoblasts into mature myocytes |
| Myogenin and MR4 | Skeletal myocyte | Secondary transcription factors required for differentiation of myoblasts from muscle stem cells |
| Myosin heavy chain | Cardio-myocyte | A component of structural and contractile protein found in cardiomyocyte |

TABLE 1-continued

Markers Commonly Used to Identify Stem Cells and to Characterize Differentiated Cell Types

| Marker Name | Cell Type | Significance |
| --- | --- | --- |
| Myosin light chain | Skeletal myocyte | A component of structural and contractile protein found in skeletal myocyte |

Skin provides yet another potential system for the compositions and methods described herein. Skin stem cell fate is controlled primarily through the well-defined transcription factor cascade of β-catenin-Lef1/Tcf cascade. Merrill et al. *Genes Dev* 2001, 15:1688-1705. As described herein, ZFPs can be used to modulate the expression of Lef1/Tcf; alternatively or in addition, expression of specific Lef1/Tcf target genes can be modulated.

Regulation of genes involved in hematopoietic stem cells is another exemplary area in which ZFPs can be used. Recently, a full-scale genome-wide expression profile of the transcriptional program of hematopoiesis has been conducted, yielding a large amount of data (http://stemcell.princeton.edu) describing changes in gene expression that occur as the stem cell proceeds down the various hematopoietic lineages. ZFPs can be used to control key regulatory genes identified in this analysis, to evoke particular transcriptional and/or phenotypic responses. Table 2 shows exemplary markers that have been identified in hematopoietic lineages.

TABLE 2

Markers of cell type

| Marker | Synonyms | Specificity |
| --- | --- | --- |
| CD 1 | | Thymocytes, Langerhans histocytes |
| CD 2 | | T and NK cells |
| CD 3 | | All thymocytes, T and NK cells |
| CD 4 | | Helper T cells |
| CD 5 | | All T cells, some B cells |
| CD 7 | | All T cells, some myeloid cells |
| CD 8 | | Cytotoxic T cells |
| CD 10 | CALLA: common acute lymphocytic leukemia antigen | Early precursor and pre-B cells |
| CD 13 | | Granulocytes, monocytes |
| CD 14 | | Monocytes |
| CD 15 | Leu M2 | All granulocytes, Reed Sternberg cells |
| CD 16 | | NK cells and granulocytes |
| CD 19 | | preB, B cells, but not plasma cells |
| CD 20 | L26 | preB, but not plasma cells |
| CD21 | EBV-R | Mature B and follicular dendritic cells |
| CD 22 | | Mature B |
| CD 23 | | Activated marrow B |
| CD 30 | Ki-I | Activation marker for B, T, and monocytes |
| CD 33 | | Myeloid progenitor and monocytes |
| CD 34 | | Early pluripotent progenitor cell |
| CD 45 | LCA, leukocyte common antigen | All leukocytes |
| CD 61 | platelet glycophorin | Associated with M7 AML |
| S100 | | Interdigitating dendritic cells of the lymph node paracortex. |
| EMA | epithelial marker antigen | Epithelial cells |
| TdT | | T and B lymphocytes, lost before maturity |

Modulation of Cellular Differentiation Using Zinc Finger Proteins

The present disclosure relates to the use of one or more engineered ZFPs to modify stem cells, for example, by creating stem cell populations from specialized cells using ZFPs to modulate expression of genes that affect dedifferentiation; by propagating stem cell populations in vivo or in vitro using ZFPs to modulate expression of genes that affect self-renewal of stem cells; or by directing a stem cell into a desired phenotype using ZFPs to modulate expression of genes involved in differentiation into a specialized phenotype.

Targeted control of stem cell differentiation using ZFP-TFs allows a number of further goals to be achieved, including, but not limited to, the generation of pure "bone-marrow type" precursors of B and T cells that can be amplified as desired; the generation of immunoglobulin and T cell receptor gene rearrangements to create diversity; the capacity for affinity maturation and class-switching; the creation a suitable source of antigen presenting cells; the production and amplification of cytotoxic T cells; and/or the creation of rapid and reliable individual donor systems of different MHC haplotypes.

Dedifferentiation and Propagation of Stem Cells

Adult stem cells have been identified in brain, bone marrow, peripheral blood, blood vessels, skeletal muscle, epithelial skin and GI tract cells, cornea, dental pulp of the tooth, retina, liver, and pancreas. However, these cells are rare and often difficult to identify, isolate and purify. Further, although these cells propagate in vivo for long periods of time, they do not survive well in culture.

Thus, researchers face many technical challenges in isolating and propagating stem cells. These challenges include: the rarity of adult stem cells among other, differentiated cells, difficulties in isolating and identifying the cells (e.g. by the markers they express), ethical considerations regarding the use of embryonic stem cells, and difficulties in growing stem cells in culture. Accordingly, the use of adult stem cells in cell-replacement strategies is currently limited by the lack of sufficient numbers of cells.

The ability of specialized cells to dedifferentiate and the ability of stem cells to self-renew in culture are undoubtedly mediated by a complex interaction of extrinsic (e.g., cell-cell interactions, media and culture conditions, extracellular matrix, etc.) and intrinsic (e.g., gene regulation and expression) signals acting on the cell. The present disclosure encompasses modulation of one or more components of one or both of intrinsic or extrinsic signals. Thus, various genes can be targeted for modulation by the ZFPs in order to maintain cells in a differentiated state and to increase the capability of these stem cell populations for expansion.

In particular, the present disclosure describes the use of engineered ZFPs (or polynucleotides encoding the same) for targeted modulation of gene expression and, accordingly, for the development of in vitro and in vivo systems of obtaining and propagating stem cell populations. Thus, in certain embodiments, compositions comprising ZFPs or functional equivalents (also referred to as "dedifferentiating compositions") are provided to a target cell or nucleus in an amount effective to reprogram the target cell or nucleus from a differentiated to a dedifferentiated state and/or to enhance the ability of cultured stem cells to survive in vivo. The amount or concentration of dedifferentiating composition necessary to achieve the desired effect can be readily determined by one of skill in the art in view of the teachings herein.

Thus, one or more ZFPs engineered to modulate expression of one or more genes involved in differentiation and/or self-renewal of stem cells are introduced into a target cell to achieve the desired result. For instance, one or more ZFPs that activate the expression of genes associated with maintaining a dedifferentiated state (e.g., stem cell phenotype) can be introduced into a target cell alone or in combination with ZFPs that inhibit the expression of genes associated with differentiation. Additionally, ZFPs that modulate expression of genes involved in propagation of stem cell cultures can also be introduced.

In certain aspects, the modulation (e.g., activation or repression) of expression by the ZFP reversible. As described in detail below, in instances in which the repression is transient, release of the inhibitory effects would then allow controllable differentiation of these cells into particular lineages. Accordingly, using the teachings described herein, for example regarding the selection of suitable regulatory domains, the control of differentiation can be either stable or transient. In this way, stem cell populations can be maintained and expanded indefinitely.

Target cells include, but are not limited to, any prokaryotic, eukaryotic and Archaeal cells. Eukaryotic cells include, plant, fungal, protozoal and animal cells, including mammalian cells, primary cells and human cells. If the cells are differentiated, it is first necessary to revert them to an at least partially dedifferentiated phenotype. Subsequently, the cells can be maintained and propagated in the desired dedifferentiated state using the ZFP-containing compositions and methods desired herein. Isolated populations of stem cells (adult or embryonic) can also be obtained and the compositions and methods described herein used to enhance propagation and survival in the dedifferentiated state.

Target cell populations include, but are not limited to, hematopoietic stem cells such as lymphoid precursor cells, Pro-B, Pre B-1 cells, myeloid precursor cells and erythroid precursor cells as well as neuronal stem cells, pancreatic stem cells, liver stem cells and epithelial stem cells. Providing compositions and methods that facilitate expansion of these stem cell populations provides an important source of stem cells for diseased and/or immunocompromised subjects.

Differentiation

In addition to the difficulties faced by researchers in obtaining self-renewing stem cell populations and in dedifferentiating cells, it has also proven difficult to direct stem cells to the desired specialized phenotype. To this end, efforts have focused primarily on directing differentiation by modulating culture conditions.

Some adult stem cells appear to have the capability to differentiate into tissue other than the one from which they originated. This capability is referred to as plasticity. Reports of human or mouse adult stem cells that demonstrate plasticity include: hematopoietic stem cells that can differentiate into skeletal muscle cells, cardiac muscles cells, liver cells and the 3 major types of brain cells (neurons, oligodendrocytes and astrocytes); stromal cells (bone marrow) that differentiate into cardiac muscle cells, skeletal muscle cells, fat, bone, and cartilage; and neuronal stem cells that differentiate into blood cells and skeletal muscle cells. (See, e.g., Anderson et al. (2001) *Nature Med* 7:393-395; Bjornson et al. (1999) *Science* 283:534-537; Mezey et al. (2000) *Science* 290:1779-1782; Theise et al. (2000) *Heptalogy* 32:11-16; U.S. Pat. No. 6,258,354).

Thus, in certain embodiments, regulation of genes involved in differentiation by zinc finger proteins is used to obtain populations of differentiated cells. The populations of cells so obtained can be fully differentiated (i.e., terminally differentiated) or partially differentiated (i.e, multipotent but lineage-restricted). For example, up-regulation of a gene that drives differentiation, or down-regulation of a gene which drives stem cell proliferation and/or self-renewal, can be used to move a cell toward a more differentiated state. The methods and compositions disclosed herein can thus be used to obtain one or more selected cell lineages, and, in certain embodiments, a single selected cell lineage, from a population of cells. For example, pluripotent cells can be converted to multipotent cells (e.g., hematopoietic stem cells can be converted into myeloid precursor cells or erythroid cells), or populations of either pluripotent or multipotent cells can be converted to populations of terminally differentiated cells (e.g., hematopoietic stem cells or lymphoid precursor cells can be converted to populations of T- or B-lymphocytes).

The isolation and identification of stem cells and, additionally, the characterization of various states of cellular differentiation, is typically accomplished by evaluating the presence of certain marker molecules, for example, cell surface markers.

Cloning

Facilitating dedifferentiation of target cells using ZFPs can also be used to increase cloning efficiency. For example, cloning of domestic and laboratory animals is typically accomplished by transplanting a cell or nucleus (usually embryonic), into an enucleated oocyte, with the expectation that an environment which allows for the development of a normal animal has been generated. General cloning strategies and techniques for nuclear transplantation are described for example in U.S. Pat. No. 6,011,197 and references cited therein. However, the efficiency of this type of nuclear transplantation is low, particularly when the nucleus to be transplanted is isolated from a somatic rather than an embryonic cell. Use of the compositions and methods described herein allows for increased efficiency of nuclear transplantation, particularly for somatic cell nuclei. Exposure of nuclei to compositions comprising one or more ZFPs targeted to genes involved in the dedifferentiation process allows nuclei to be reprogrammed and/or dedifferentiated to varying degrees prior to, or coincident with, their transplantation, thereby increasing cloning efficiency.

Grafting

The compositions and methods described herein also allow for novel approaches and systems to address immune reactions of a host to allogeneic grafts. In particular, a major problem faced when allogeneic stem cells (or any type of allogeneic cell) are grafted into a host recipient is the high risk of rejection by the host's immune system, primarily mediated through recognition of the Major Histocompatibility Complex (MHC) on the surface of the engrafted cells. The MHC comprises the HLA class I protein(s) that function as heterodimers that are comprised of a common β subunit and variable α subunits. It has been demonstrated that tissue grafts derived from stem cells that are devoid of HLA escape the host's immune response. See, e.g., Coffman et al. *J Immunol* 151, 425-35. (1993); Markmann et al. *Transplantation* 54, 1085-9. (1992); Koller et al. *Science* 248, 1227-30. (1990). Using the compositions and methods described herein, proteins in the HLA involved in graft rejection can be modulated to reduce the adverse reactions. For example, by repressing expression of the common β subunit gene (β2 microglobulin) using ZFPs as described herein, HLA class I can be removed from the cells to rapidly and reliably generate HLA class I null stem cells from any donor, thereby reducing the need for closely matched donor/recipient MHC haplotypes during stem cell grafting.

Temporal Control

In certain embodiments, the ZFP is used to modulate gene expression conditionally, for example, at a certain time after it is introduced and/or for a set period of time. For example, HoxB4 enables long-term hematopoietic stem cells (HSC) and ES cells to give rise to both branches of hematopoiesis (the myeloid and lymphoid lineages) but only transient expression of this transcription factor to a specific level is required to regulate stem cell fate most effectively—with continued expression being counterproductive. (See, e.g., Brun et al. *Blood* 98, 66a (2001)).

One or more of the following approaches to temporal control can be used: (i) a differentiation response following delivery of a ZFP-TF protein itself; (ii) use of a constitutive promoter operably linked to a polynucleotide encoding a ZFP-TF; (iii) use of a inducible promoter (e.g., for example, a doxycycline-regulated promoter); (iv) use of an inducible functional domain (e.g., a hormone receptor ligand-binding domain). In any of these embodiments, the ZFP-encoding constructs may be stably or transiently integrated into the cell's genome. (See, e.g., Zhang et al. *J Biol Chem* 275, 33850-60. (2000)).

In addition, studies show that a wide variety of genes in all eukaryotic species are subject to "epigenetic" regulation of gene expression—i.e., a mode of regulation that persists, and is stable, in the absence of the initial causative stimulus, such as action by a transcription factor. See, e.g., Chadwick, D. J. & Cardew, G. (eds.) *Epigenetics* (John Wiley, Chichester, England, 1998); Russo, V. E. A., Martienssen, R. A. & Riggs, A. D. (eds.) *Epigenetic mechanisms of gene regulation* (Cold Spring Harbor Laboratory Press, Plainview, N.Y., 1996). Epigenetic regulation is particularly central to the process of cell differentiation, as distinguished from gene expression in general. Because the activated or repressed state of a gene is passed on epigenetically to daughter cells, the differentiated phenotype is fixed. Such a mechanism might be exploited by permanently switching on or off an endogenous gene that regulates differentiation, for example by use of a factor (e.g., ZFP) that will bind to and specifically modify the specified genes.

Assaying Cell State

Cells can be assayed in order to determine their particular state of differentiation using a variety of well-known techniques. For example, the presence or absence of cell surface markers (e.g., Table 1) can be assayed by flow cytometry techniques, antibody binding techniques, chromatography, membrane filters, and the like. Rolink et al. (1994) *Int Immunology* 6:1257-1264); Jankowski et al. (2001) *Hum Gene Therapy* 12:619-628; U.S. Pat. No. 6,268,119.

An additional assay for cell state is modulation of gene expression. Assays for gene modulation (e.g., transcriptional activation and/or repression, reporter gene activity, measurement of protein levels) are well-known to those of skill in the art and are described, for example, in co-owned WO 00/41566.

Polynucleotide and Polypeptide Delivery

Accordingly, in one embodiment, one or more ZFPs are expressed in a cell in order to dedifferentiate the cell (e.g., a somatic cell which is to be used as a donor of a enucleated, inactivated or purified nucleus for transplantation into an egg), direct a cell to particular phenotype and/or maintain and propagate a cell in the desired state of differentiation. The compositions described herein, comprising one or more specifically targeted ZFPs, can be provided to the target cell in vitro or in vivo. In addition, the compositions can be provided as polypeptides, polynucleotides or combinations thereof.

A. Delivery of Polynucleotides

In certain embodiments, the compositions are provided as one or more polynucleotides. Further, as noted above, the ZFPs may be designed as fusions with one or more regulatory domains and, in certain embodiments, the fusion molecule is encoded by a nucleic acid. In both fusion and non-fusion cases, the nucleic acid can be cloned into intermediate vectors for transformation into prokaryotic or eukaryotic cells for replication and/or expression. Intermediate vectors for storage or manipulation of the nucleic acid or production of protein can be prokaryotic vectors, (e.g., plasmids), shuttle vectors, insect vectors, or viral vectors for example. A ZFP-encoding nucleic acid can also cloned into an expression vector, for administration to a bacterial cell, fungal cell, protozoal cell, plant cell, or animal cell, preferably a mammalian cell, more preferably a human cell.

To obtain expression of a cloned nucleic acid, it is typically subcloned into an expression vector that contains a promoter to direct transcription. Suitable bacterial and eukaryotic promoters are well known in the art and described, e.g., in Sambrook et al., supra; Ausubel et al., supra; and Kriegler, *Gene Transfer and Expression: A Laboratory Manual* (1990). Bacterial expression systems are available in, e.g., *E. coli, Bacillus* sp., and *Salmonella*. Palva et al. (1983) *Gene* 22:229-235. Kits for such expression systems are commercially available. Eukaryotic expression systems for mammalian cells, yeast, and insect cells are well known in the art and are also commercially available, for example, from Invitrogen, Carlsbad, Calif. and Clontech, Palo Alto, Calif.

The promoter used to direct expression of the nucleic acid of choice depends on the particular application. For example, a strong constitutive promoter is typically used for expression and purification. In contrast, when a dedifferentiation protein is to be used in vivo, either a constitutive or an inducible promoter is used, depending on the particular use of the protein. In addition, a weak promoter can be used, such as HSV TK or a promoter having similar activity. The promoter typically can also include elements that are responsive to transactivation, e.g., hypoxia response elements, Gal4 response elements, lac repressor response element, and small molecule control systems such as tet-regulated systems and the RU-486 system. See, e.g., Gossen et al. (1992) *Proc. Natl. Acad. Sci USA* 89:5547-5551; Oligino et al. (1998) *Gene Ther.* 5:491-496; Wang et al. (1997) *Gene Ther.* 4:432-441; Neering et al. (1996) *Blood* 88:1147-1155; and Rendahl et al. (1998) *Nat. Biotechnol.* 16:757-761.

In addition to a promoter, an expression vector typically contains a transcription unit or expression cassette that contains additional elements required for the expression of the nucleic acid in host cells, either prokaryotic or eukaryotic. A typical expression cassette thus contains a promoter operably linked, e.g., to the nucleic acid sequence, and signals required, e.g., for efficient polyadenylation of the transcript, transcriptional termination, ribosome binding, and/or translation termination. Additional elements of the cassette may include, e.g., enhancers, and heterologous spliced intronic signals.

The particular expression vector used to transport the genetic information into the cell is selected with regard to the intended use of the resulting dedifferentiation polypeptide, e.g., expression in plants, animals, bacteria, fungi, protozoa etc. Standard bacterial expression vectors include plasmids such as pBR322, pBR322-based plasmids, pSKF, pET23D, and commercially available fusion expression systems such as GST and LacZ. Epitope tags can also be added to recombinant proteins to provide convenient methods of isolation, for monitoring expression, and for monitoring cellular and subcellular localization, e.g., c-myc or FLAG.

Expression vectors containing regulatory elements from eukaryotic viruses are often used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the SV40 early promoter, SV40 late promoter, metallothionein promoter, murine mammary tumor virus promoter, Rous sarcoma virus promoter, polyhedrin promoter, or other promoters shown effective for expression in eukaryotic cells.

Some expression systems have markers for selection of stably transfected cell lines such as thymidine kinase, hygromycin B phosphotransferase, and dihydrofolate reductase. High-yield expression systems are also suitable, such as baculovirus vectors in insect cells, with a dedifferentiation nucleic acid sequence under the transcriptional control of the polyhedrin promoter or any other strong baculovirus promoter.

Elements that are typically included in expression vectors also include a replicon that functions in *E. coli* (or in the prokaryotic host, if other than *E. coli*), a selective marker, e.g., a gene encoding antibiotic resistance, to permit selection of bacteria that harbor recombinant plasmids, and unique restriction sites in nonessential regions of the vector to allow insertion of recombinant sequences.

Standard transfection methods can be used to produce bacterial, mammalian, yeast, insect, or other cell lines that express large quantities of dedifferentiation proteins, which can be purified, if desired, using standard techniques. See, e.g., Colley et al. (1989) *J. Biol. Chem.* 264:17619-17622; and *Guide to Protein Purification, in Methods in Enzymology*, vol. 182 (Deutscher, ed.) 1990. Transformation of eukaryotic and prokaryotic cells are performed according to standard techniques. See, e.g., Morrison (1977) *J. Bacteriol.* 132:349-351; Clark-Curtiss et al. (1983) in *Methods in Enzymology* 101:347-362 (Wu et al., eds).

Any procedure for introducing foreign nucleotide sequences into host cells can be used. These include, but are not limited to, the use of calcium phosphate transfection, DEAE-dextran-mediated transfection, polybrene, protoplast fusion, electroporation, lipid-mediated delivery (e.g., liposomes), microinjection, particle bombardment, introduction of naked DNA, plasmid vectors, viral vectors (both episomal and integrative) and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing the protein of choice.

Conventional viral and non-viral based gene transfer methods can be used to introduce nucleic acids into mammalian cells or target tissues. Such methods can be used to administer nucleic acids encoding reprogramming polypeptides to cells in vitro. Preferably, nucleic acids are administered for in vivo or ex vivo gene therapy uses. Non-viral vector delivery systems include DNA plasmids, naked nucleic acid, and nucleic acid complexed with a delivery vehicle such as a liposome. Viral vector delivery systems include DNA and RNA viruses, which have either episomal or integrated genomes after delivery to the cell. For reviews of gene therapy procedures, see, for example, Anderson (1992) *Science* 256:808-813; Nabel et al. (1993) *Trends Biotechnol.* 11:211-217; Mitani et al. (1993) *Trends Biotechnol.* 11:162-166; Dillon (1993) *Trends Biotechnol.* 11:167-175; Miller (1992) *Nature* 357:455-460; Van Brunt (1988) *Biotechnology* 6(10):1149-1154; Vigne (1995) *Restorative Neurology and Neuroscience* 8:35-36; Kremer et al. (1995) *British Medical Bulletin* 51(1):31-44; Haddada et al., in *Current Topics in Microbiology and Immunology*, Doerfler and Böhm (eds), 1995; and Yu et al. (1994) *Gene Therapy* 1:13-26.

Methods of non-viral delivery of nucleic acids include lipofection, microinjection, ballistics, virosomes, liposomes, immunoliposomes, polycation or lipid:nucleic acid conjugates, naked DNA, artificial virions, and agent-enhanced uptake of DNA. Lipofection is described in, e.g., U.S. Pat. Nos. 5,049,386; 4,946,787; and 4,897,355 and lipofection reagents are sold commercially (e.g., Transfectam™ and Lipofectin™). Cationic and neutral lipids that are suitable for efficient receptor-recognition lipofection of polynucleotides include those of Feigner, WO 91/17424 and WO 91/16024. Nucleic acid can be delivered to cells (ex vivo administration) or to target tissues (in vivo administration).

The preparation of lipid:nucleic acid complexes, including targeted liposomes such as immunolipid complexes, is well known to those of skill in the art. See, e.g., Crystal (1995) *Science* 270:404-410; Blaese et al. (1995) *Cancer Gene Ther.* 2:291-297; Behr et al. (1994) *Bioconjugate Chem.* 5:382-389; Remy et al. (1994) *Bioconjugate Chem.* 5:647-654; Gao et al. (1995) *Gene Therapy* 2:710-722; Ahmad et al. (1992) *Cancer Res.* 52:4817-4820; and U.S. Pat. Nos. 4,186,183; 4,217,344; 4,235,871; 4,261,975; 4,485,054; 4,501,728; 4,774,085; 4,837,028 and 4,946,787.

The use of RNA or DNA virus-based systems for the delivery of nucleic acids take advantage of highly evolved processes for targeting a virus to specific cells in the body and trafficking the viral payload to the nucleus. Viral vectors can be administered directly to patients (in vivo) or they can be used to treat cells in vitro, wherein the modified cells are administered to patients (ex vivo). Conventional viral based systems for the delivery of ZFPs include retroviral, lentiviral, poxviral, adenoviral, adeno-associated viral, vesicular stomatitis viral and herpesviral vectors. Integration in the host genome is possible with certain viral vectors, including the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, allowing alteration and/or expansion of the potential target cell population. Lentiviral vectors are retroviral vector that are able to transduce or infect non-dividing cells and typically produce high viral titers. Selection of a retroviral gene transfer system would therefore depend on the target tissue. Retroviral vectors have a packaging capacity of up to 6-10 kb of foreign sequence and are comprised of cis-acting long terminal repeats (LTRs). The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), simian immunodeficiency virus (SIV), human immunodeficiency virus (HIV), and combinations thereof. Buchscher et al.

(1992) *J. Virol.* 66:2731-2739; Johann et al. (1992) *J. Virol.* 66:1635-1640; Sommerfelt et al. (1990) *Virol.* 176:58-59; Wilson et al. (1989) *J. Virol.* 63:2374-2378; Miller et al. (1991) *J. Virol.* 65:2220-2224; and PCT/US94/05700).

Adeno-associated virus (AAV) vectors are also used to transduce cells with target nucleic acids, e.g., in the in vitro production of nucleic acids and peptides, and for in vivo and ex vivo gene therapy procedures. See, e.g., West et al. (1987) *Virology* 160:38-47; U.S. Pat. No. 4,797,368; WO 93/24641; Kotin (1994) *Hum. Gene Ther.* 5:793-801; and Muzyczka (1994) *J. Clin. Invest.* 94:1351. Construction of recombinant AAV vectors are described in a number of publications, including U.S. Pat. No. 5,173,414; Tratschin et al. (1985) *Mol. Cell. Biol.* 5:3251-3260; Tratschin, et al. (1984) *Mol. Cell. Biol.* 4:2072-2081; Hermonat et al. (1984) *Proc. Natl. Acad. Sci. USA* 81:6466-6470; and Samulski et al. (1989) *J. Virol.* 63:3822-3828.

Recombinant adeno-associated virus vectors based on the defective and nonpathogenic parvovirus adeno-associated virus type 2 (AAV-2) are a promising gene delivery system. Exemplary AAV vectors are derived from a plasmid containing the AAV 145 bp inverted terminal repeats flanking a transgene expression cassette. Efficient gene transfer and stable transgene delivery due to integration into the genomes of the transduced cell are key features for this vector system. Wagner et al. (1998) *Lancet* 351⊕(9117):1702-3; and Kearns et al. (1996) *Gene Ther.* 9:748-55.

pLASN and MFG-S are examples are retroviral vectors that have been used in clinical trials. Dunbar et al. (1995) *Blood* 85:3048-305; Kohn et al. (1995) *Nature Med.* 1:1017-102; Malech et al. (1997) *Proc. Natl. Acad. Sci. USA* 94:12133-12138. PA317/pLASN was the first therapeutic vector used in a gene therapy trial. (Blaese et al. (1995) *Science* 270:475-480. Transduction efficiencies of 50% or greater have been observed for MFG-S packaged vectors. Ellem et al. (1997) *Immunol Immunother.* 44(1):10-20; Dranoff et al. (1997) *Hum. Gene Ther.* 1:111-2.

In applications for which transient expression is preferred, adenoviral-based systems are useful. Adenoviral based vectors are capable of very high transduction efficiency in many cell types and are capable of infecting, and hence delivering nucleic acid to, both dividing and non-dividing cells. With such vectors, high titers and levels of expression have been obtained. Adenovirus vectors can be produced in large quantities in a relatively simple system.

Replication-deficient recombinant adenoviral (Ad) can be produced at high titer and they readily infect a number of different cell types. Most adenovirus vectors are engineered such that a transgene replaces the Ad E1a, E1b, and/or E3 genes; the replication defector vector is propagated in human 293 cells that supply the required E1 functions in trans. Ad vectors can transduce multiple types of tissues in vivo, including non-dividing, differentiated cells such as those found in the liver, kidney and muscle. Conventional Ad vectors have a large carrying capacity for inserted DNA. An example of the use of an Ad vector in a clinical trial involved polynucleotide therapy for antitumor immunization with intramuscular injection. Sterman et al. (1998) *Hum. Gene Ther.* 7:1083-1089. Additional examples of the use of adenovirus vectors for gene transfer in clinical trials include Rosenecker et al. (1996) *Infection* 24:5-10; Sterman et al., supra; Welsh et al. (1995) *Hum. Gene Ther.* 2:205-218; Alvarez et al. (1997) *Hum. Gene Ther.* 5:597-613; and Topf et al. (1998) *Gene Ther.* 5:507-513.

Packaging cells are used to form virus particles that are capable of infecting a host cell. Such cells include 293 cells, which package adenovirus, and Ψ2 cells or PA317 cells, which package retroviruses. Viral vectors used in gene therapy are usually generated by a producer cell line that packages a nucleic acid vector into a viral particle. The vectors typically contain the minimal viral sequences required for packaging and subsequent integration into a host, other viral sequences being replaced by an expression cassette for the protein to be expressed. Missing viral functions are supplied in trans, if necessary, by the packaging cell line. For example, AAV vectors used in gene therapy typically only possess ITR sequences from the AAV genome, which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment, which preferentially inactivates adenoviruses.

In many gene therapy applications, it is desirable that the gene therapy vector be delivered with a high degree of specificity to a particular tissue type. A viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al. (1995) *Proc. Natl. Acad. Sci. USA* 92:9747-9751 reported that Moloney murine leukemia virus can be modified to express human heregulin fused to gp70, and the recombinant virus infects certain human breast cancer cells expressing human epidermal growth factor receptor. This principle can be extended to other pairs of virus expressing a ligand fusion protein and target cell expressing a receptor. For example, filamentous phage can be engineered to display antibody fragments (e.g., $F_{ab}$ or $F_v$) having specific binding affinity for virtually any chosen cellular receptor. Although the above description applies primarily to viral vectors, the same principles can be applied to non-viral vectors. Such vectors can be engineered to contain specific uptake sequences thought to favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described infra. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Ex vivo cell transfection for diagnostics, research, or for gene therapy (e.g., via re-infusion of the transfected cells into the host organism) is well known to those of skill in the art. In a preferred embodiment, cells are isolated from the subject organism, transfected with a nucleic acid (gene or cDNA), and re-infused back into the subject organism (e.g., patient). Various cell types suitable for ex vivo transfection are well known to those of skill in the art. See, e.g., Freshney et al., *Culture of Animal Cells, A Manual of Basic Technique*, 3rd ed., 1994, and references cited therein, for a discussion of isolation and culture of cells from patients.

In one embodiment, hematopoietic stem cells are used in ex vivo procedures for cell transfection and gene therapy.

The advantage to using stem cells is that they can be differentiated into other cell types in vitro, or can be introduced into a mammal (such as the donor of the cells) where they will engraft in the bone marrow. Methods for differentiating CD34+ stem cells in vitro into clinically important immune cell types using cytokines such a GM-CSF, IFN-γ and TNF-α are known. Inaba et al. (1992) *J. Exp. Med.* 176:1693-1702.

Stem cells are isolated for transduction and differentiation using known methods. For example, stem cells are isolated from bone marrow cells by panning the bone marrow cells with antibodies which bind unwanted cells, such as CD4+ and CD8+ (T cells), CD45+ (panB cells), GR-1 (granulocytes), and lad (differentiated antigen presenting cells). See Inaba et al., supra.

Vectors (e.g., retroviruses, adenoviruses, liposomes, etc.) containing therapeutic nucleic acids can be also administered directly to the organism for transduction of cells in vivo. Alternatively, naked DNA can be administered. Administration is by any of the routes normally used for introducing a molecule into ultimate contact with blood or tissue cells. Suitable methods of administering such nucleic acids are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions, as described below. See, e.g., *Remington's Pharmaceutical Sciences,* 17th ed., 1989.

B. Delivery of Polypeptides

In other embodiments, for example in certain in vitro situations, the target cells are cultured in a medium containing one or more targeted ZFPs.

An important factor in the administration of polypeptide compounds is ensuring that the polypeptide has the ability to traverse the plasma membrane of a cell, or the membrane of an intra-cellular compartment such as the nucleus. Cellular membranes are composed of lipid-protein bilayers that are freely permeable to small, nonionic lipophilic compounds and are inherently impermeable to polar compounds, macromolecules, and therapeutic or diagnostic agents. However, proteins, lipids and other compounds, which have the ability to translocate polypeptides across a cell membrane, have been described.

For example, "membrane translocation polypeptides" have amphiphilic or hydrophobic amino acid subsequences that have the ability to act as membrane-translocating carriers. In one embodiment, homeodomain proteins have the ability to translocate across cell membranes. The shortest internalizable peptide of a homeodomain protein, Antennapedia, was found to be the third helix of the protein, from amino acid position 43 to 58. Prochiantz (1996) *Curr. Opin. Neurobiol.* 6:629-634. Another subsequence, the h (hydrophobic) domain of signal peptides, was found to have similar cell membrane translocation characteristics. Lin et al. (1995) *J. Biol. Chem.* 270:14255-14258.

Examples of peptide sequences which can facilitate protein uptake into cells include, but are not limited to: an 11 amino acid peptide of the tat protein of HIV; a 20 residue peptide sequence which corresponds to amino acids 84-103 of the p16 protein (see Fahraeus et al. (1996) *Curr. Biol.* 6:84); the third helix of the 60-amino acid long homeodomain of Antennapedia (Derossi et al. (1994) *J. Biol. Chem.* 269:10444); the h region of a signal peptide, such as the Kaposi fibroblast growth factor (K-FGF) h region (Lin et al., supra); and the VP22 translocation domain from HSV (Elliot et al. (1997) *Cell* 88:223-233). Other suitable chemical moieties that provide enhanced cellular uptake can also be linked, either covalently or non-covalently, to the ZFP or ZFP-containing fusion molecules.

Toxin molecules also have the ability to transport polypeptides across cell membranes. Often, such molecules (called "binary toxins") are composed of at least two parts: a translocation or binding domain and a separate toxin domain Typically, the translocation domain, which can optionally be a polypeptide, binds to a cellular receptor, facilitating transport of the toxin into the cell. Several bacterial toxins, including *Clostridium perfringens* iota toxin, diphtheria toxin (DT), *Pseudomonas* exotoxin A (PE), pertussis toxin (PT), *Bacillus anthracis* toxin, and pertussis adenylate cyclase (CYA), have been used to deliver peptides to the cell cytosol as internal or amino-terminal fusions. Arora et al. (1993) *J. Biol. Chem.* 268:3334-3341; Perelle et al. (1993) *Infect. Immun.* 61:5147-5156; Stenmark et al. (1991) *J. Cell Biol.* 113:1025-1032; Donnelly et al. (1993) *Proc. Natl. Acad. Sci. USA* 90:3530-3534; Carbonetti et al. (1995) *Abstr. Annu. Meet. Am. Soc. Microbiol.* 95:295; Sebo et al. (1995) *Infect. Immun.* 63:3851-3857; Klimpel et al. (1992) *Proc. Natl. Acad. Sci. USA.* 89:10277-10281; and Novak et al. (1992) *J. Biol. Chem.* 267:17186-17193.

Such subsequences can be used to translocate polypeptides, including the polypeptides as disclosed herein, across a cell membrane. This is accomplished, for example, by derivatizing the fusion polypeptide with one of these translocation sequences, or by forming an additional fusion of the translocation sequence with the fusion polypeptide. Optionally, a linker can be used to link the fusion polypeptide and the translocation sequence. Any suitable linker can be used, e.g., a peptide linker.

A suitable polypeptide can also be introduced into an animal cell, preferably a mammalian cell, via liposomes and liposome derivatives such as immunoliposomes. The term "liposome" refers to vesicles comprised of one or more concentrically ordered lipid bilayers, which encapsulate an aqueous phase. The aqueous phase typically contains the compound to be delivered to the cell.

The liposome fuses with the plasma membrane, thereby releasing the compound into the cytosol. Alternatively, the liposome is phagocytosed or taken up by the cell in a transport vesicle. Once in the endosome or phagosome, the liposome is either degraded or it fuses with the membrane of the transport vesicle and releases its contents.

In current methods of drug delivery via liposomes, the liposome ultimately becomes permeable and releases the encapsulated compound at the target tissue or cell. For systemic or tissue specific delivery, this can be accomplished, for example, in a passive manner wherein the liposome bilayer is degraded over time through the action of various agents in the body. Alternatively, active drug release involves using an agent to induce a permeability change in the liposome vesicle. Liposome membranes can be constructed so that they become destabilized when the environment becomes acidic near the liposome membrane. See, e.g., *Proc. Natl. Acad. Sci. USA* 84:7851 (1987); *Biochemistry* 28:908 (1989). When liposomes are endocytosed by a target cell, for example, they become destabilized and release their contents. This destabilization is termed fusogenesis. Dioleoylphosphatidylethanolamine (DOPE) is the basis of many "fusogenic" systems.

For use with the methods and compositions disclosed herein, liposomes typically comprise a fusion polypeptide as disclosed herein, a lipid component, e.g., a neutral and/or cationic lipid, and optionally include a receptor-recognition molecule such as an antibody that binds to a predetermined cell surface receptor or ligand (e.g., an antigen). A variety of methods are available for preparing liposomes as described in, e.g.; U.S. Pat. Nos. 4,186,183; 4,217,344; 4,235,871; 4,261,975; 4,485,054; 4,501,728; 4,774,085; 4,837,028; 4,235,871; 4,261,975; 4,485,054; 4,501,728; 4,774,085; 4,837,028; 4,946,787; PCT Publication No. WO 91/17424; Szoka et al. (1980) *Ann. Rev. Biophys. Bioeng.* 9:467; Deamer et al. (1976) *Biochim. Biophys. Acta* 443:629-634; Fraley, et al. (1979) *Proc. Natl. Acad. Sci. USA* 76:3348-3352; Hope et al. (1985) *Biochim. Biophys. Acta* 812:55-65; Mayer et al. (1986) *Biochim. Biophys. Acta* 858:161-168; Williams et al. (1988) *Proc. Natl. Acad. Sci. USA* 85:242-246; *Liposomes*, Ostro (ed.), 1983, Chapter 1); Hope et al. (1986) *Chem. Phys. Lip.* 40:89; Gregoriadis, *Liposome Technology* (1984) and Lasic, *Liposomes: from Physics to Applications* (1993). Suitable methods include, for example, sonication, extrusion, high pressure/homogenization, microfluidization, detergent dialysis, calcium-induced fusion of small liposome vesicles and ether-fusion methods, all of which are well known in the art.

In certain embodiments, it may be desirable to target a liposome using targeting moieties that are specific to a particular cell type, tissue, and the like. Targeting of liposomes using a variety of targeting moieties (e.g., ligands, receptors, and monoclonal antibodies) has been previously described. See, e.g., U.S. Pat. Nos. 4,957,773 and 4,603,044.

Examples of targeting moieties include monoclonal antibodies specific to antigens associated with neoplasms, such as prostate cancer specific antigen and MAGE. Tumors can also be diagnosed by detecting gene products resulting from the activation or over-expression of oncogenes, such as ras or c-erbB2. In addition, many tumors express antigens normally expressed by fetal tissue, such as the alphafetoprotein (AFP) and carcinoembryonic antigen (CEA). Sites of viral infection can be diagnosed using various viral antigens such as hepatitis B core and surface antigens (HBVc, HBVs) hepatitis C antigens, Epstein-Barr virus antigens, human immunodeficiency type-1 virus (HIV-1) and papilloma virus antigens. Inflammation can be detected using molecules specifically recognized by surface molecules which are expressed at sites of inflammation such as integrins (e.g., VCAM-1), selectin receptors (e.g., ELAM-1) and the like.

Standard methods for coupling targeting agents to liposomes are used. These methods generally involve the incorporation into liposomes of lipid components, e.g., phosphatidylethanolamine, which can be activated for attachment of targeting agents, or incorporation of derivatized lipophilic compounds, such as lipid derivatized bleomycin. Antibody targeted liposomes can be constructed using, for instance, liposomes which incorporate protein A. See Renneisen et al. (1990) *J. Biol. Chem.* 265:16337-16342 and Leonetti et al. (1990) *Proc. Natl. Acad. Sci. USA* 87:2448-2451.

Pharmaceutical Compositions and Administration

ZFPs as disclosed herein, and expression vectors encoding these polypeptides, can be used in conjunction with various methods to facilitate treatment of various disease states, congenital conditions or degenerative illnesses. In such applications, targeted ZFP polypeptides or polynucleotides encoding these ZFPs can be administered directly to a patient, e.g., to facilitate the modulation of gene expression involved in differentiation and replacement of specific stem cell types, for example, in cancer, ischemia, diabetic retinopathy, macular degeneration, rheumatoid arthritis, psoriasis, HIV infection, sickle cell anemia, Alzheimer's disease, muscular dystrophy, neurodegenerative diseases, vascular disease, cystic fibrosis, stroke, and the like.

Administration of therapeutically effective amounts of one or more ZFPs or a nucleic acid encoding such ZFPs is by any of the routes normally used for introducing polypeptides or nucleic acids into ultimate contact with the tissue to be treated. The polypeptides or nucleic acids are administered in any suitable manner, preferably with pharmaceutically acceptable carriers. Suitable methods of administering such modulators are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there are a wide variety of suitable formulations of pharmaceutical compositions. See, e.g., *Remington's Pharmaceutical Sciences*, 17$^{th}$ ed. 1985.

ZFPs polypeptides or nucleic acids, alone or in combination with other suitable components, can be made into aerosol formulations (e.g., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intravenous, intramuscular, intradermal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Compositions can be administered, for example, by intravenous infusion, orally, topically, intraperitoneally, intravesically or intrathecally. The formulations of compounds can be presented in unit-dose or multi-dose sealed containers, such as ampoules and vials. Injection solutions and suspensions can be prepared from sterile powders, granules, and tablets of the kind known to those of skill in the art.

Applications

The compositions and methods disclosed herein can be used to facilitate a number of processes involved in development and dedifferentiation. These processes include, but are not limited to, dedifferentiation or differentiation of a target cell, cloning, creation of cell lineages, immortalization of cells, replication, recombination, repair and/or integration. Accordingly, the methods and compositions disclosed herein can be used to affect any of these processes, as well as any other developmental process which can be influenced by modulation of gene expression, including epigenetic modulation.

In one embodiment, the compositions and methods disclosed herein are used to provide transplant tissue or cells that are not subject to immune rejection by the recipient. See, e.g., See, e.g., Coffman et al. *J Immunol* 151, 425-35. (1993); Markmann et al. *Transplantation* 54, 1085-9. (1992); Koller et al. *Science* 248, 1227-30. (1990); Gurdon et al. *Nature* 402(6763):743-6 (1999). Obtaining or generating a dedifferentiated stem cell and directing differentiation into a particular cell type using one or more ZFPs can lead to production of tissue suitable for transplant into the individual in need thereof. In certain embodiments, the stem cell is obtained from the transplant recipient, and, accordingly, it will not stimulate an immune response, as would tissue from an unrelated donor. Such transplants can constitute solid organ transplants (e.g., heart, liver, kidney) or cell transplants for the treatment of various malignancies such as, for example, leukemias and lymphomas. The stem cells can be differentiated using ZFPs in vitro or, alternatively, in vivo. Such transplants can also be used in the treatment of, for example, neurological disorders, diabetes and the like.

site of the mouse OCT 4 gene, was designed using methods for the design and synthesis of zinc finger proteins able to bind to preselected sites disclosed in co-owned U.S. Pat. No. 6,453,242; WO 00/41566 and PCT/US01/43568. The target sequence and the amino acid sequences of the recognition regions of the zinc fingers of this protein is given in Table 3.

TABLE 3

Designed zinc finger protein binding domains

| ZFP# | target binding site | F1 sequence* | F2 sequence* | F3 sequence* |
|---|---|---|---|---|
| 1547 | OCT4 GAGGTKGGG (SEQ ID NO: 1) | RSDHLAR (SEQ ID NO: 2) | TSGSLTR (SEQ ID NO: 3) | RSDNLAR (SEQ ID NO: 4) |

*The amino acid sequences shown are those of amino acids −1 through +6 (with respect to the start of the alpha-helical portion of the zinc finger) and are given in the one-letter code

EXAMPLES

The following examples are presented as illustrative of, but not limiting, the claimed subject matter.

Example 1

OCT4 Function in Stem Cells

The OCT 4 transcription factor (also known as OCT3/4) is expressed in germ cells and in totipotent embryonic stem cells (ES cells). It is involved in the regulation of a number of genes, either directly or indirectly. Expression of OCT4, together with expression of the Stat3 gene product, is correlated with maintenance of totipotency and self-renewal (e.g., proliferation) of stem cells. During embryonic development, down-regulation of OCT4 expression results in differentiation.

Recent studies in which its expression was modulated in ES cells have shown that levels of OCT4 expression ranging between 50 and 150% of normal levels are sufficient for self-renewal of the stem cell population and maintenance of totipotency. Lower levels of OCT4 expression (50% or less of normal) result in differentiation into trophectoderm, while OCT4 levels above 150% of normal result in differentiation into endoderm and mesoderm. See, Niwa et al. (2000) *Nature Genetics* 24:372-376.

Changes in levels of OCT4 expression are correlated with changes in expression of a number of other genes, indicating that expression of these genes is likely to be regulated, either directly or indirectly, by OCT4. In particular, increase in OCT4 expression, from an integrated cDNA, in ES cells resulted in an increase in expression of the Otx1 gene. Decreased levels of OCT4 resulted in repression of Otx1 and activation of Hand1, a transcription factor involved in trophoblast differentiation. Niwa et al. (2000) *Nature Genetics* 24:372-376.

Example 2

Design of ZFPs that Bind the OCT4 Gene

A ZFP binding domain, targeted to a sequence approximately 130 nucleotides upstream of the transcriptional start Constructs were generated in which sequences encoding the ZFP binding domains shown in Table 3 were fused either to sequences encoding a VP16 transcriptional activation domain (construct named v-1547) or to sequences encoding a KOX-1 repression domain (construct named x-1547), using methods disclosed in co-owned U.S. Pat. No. 6,453, 242 and co-owned WO 00/41566. These constructs were separately transfected into mouse ES cells, and their effects on expression of the OCT 4 gene were determined.

Example 3

Regulation of the OCT4 Gene in Mouse Embryonic Stem Cells Using Engineered Zinc Finger Proteins Mouse embryonic stem cell line ES-D3 was obtained from the American Type Culture Collection (ATCC, Manassas, Va.). Cells were propagated on gelatin coated dishes at 37° C. in Knockout D-MEM medium (Gibco-BRL) supplemented with 10% FBS, 2 mM L-glutamine and 10 ng/ml murine leukemia inhibitory factor (LIF).

For transfection, cells were plated in 12-well plates at a density of $2 \times 10^5$ cells per well one day before transfection. For each well 1.7 µg DNA (v-1547 or x-1547 or GFP, a negative control) was diluted in 180 µl serum-free OPTI-MEM I medium, mixed with LipofectAMINE 2000 (4 µl diluted in 180 µl OPTI-MEM I), and incubated for 20 minutes at room temperature. Cells were rinsed with serum-free medium, and the transfection mixture was introduced into the well. After 4-5 h, the transfection mixture was replaced with regular growth medium.

At 48 h after transfection, total cellular RNA was isolated using the "High Pure RNA Isolation Kit" (Roche Diagnostics Corporation, Indianapolis, Ind.) and was analyzed for OCT4 mRNA levels by real-time PCR (TaqMan®, Roche), using an ABI PRISM 7700 Sequence Detector (Applied Biosystems, Foster City, Calif.). Glyceraldehyde-3-phosphate dehydrogenase (GAPDH) mRNA levels were also measured and used as a normalization standard. Primers and probes used for mRNA analysis are given in Table 4.

TABLE 4

Probe and primer sequences for RNA analysis

| Gene | Oligonucleotide | SEQUENCE | SEQ ID NO |
|---|---|---|---|
| OCT4 | Forward primer | CTCACCCTGGGCGTTCTCT | 5 |
| | Reverse primer | AGGCCTCGAAGCGACAGA | 6 |
| | Probe | TGGAAAGGTGTTCAGCCAGACCACC | 7 |
| OTX1 | Forward primer | ATCAACCTGCCAGAGTCCAGAGT | 8 |
| | Reverse primer | CCGGGTTTTCGTTCCATTC | 9 |
| | Probe | AGTGCCGCCAGCAGCAGCAGA | 10 |
| Hand1 | Forward primer | GCCAAGGATGCACAAGCA | 11 |
| | Reverse primer | GGGCTGCTGAGGCAACTC | 12 |
| | Probe | CTTTTCCGCTTGCTTTCGCGACC | 13 |
| HOXB4 | Forward primer | GGAACAGCGAGCACCGAA | 14 |
| | Reverse primer | CCTTTCTATAAATAAGGCTTCCCTACC | 15 |
| | Probe | CCCCGGGCTTGAGCCCAGAA | 16 |
| GAPDH | Forward primer | CCCATGTTTGTGATGGGTGTG | 17 |
| | Reverse primer | TGGCATGGACTGTGGTCATGA | 18 |
| | Probe | ATCCTGCACCACCAACTGCTTAGC | 19 |

Figure 2:
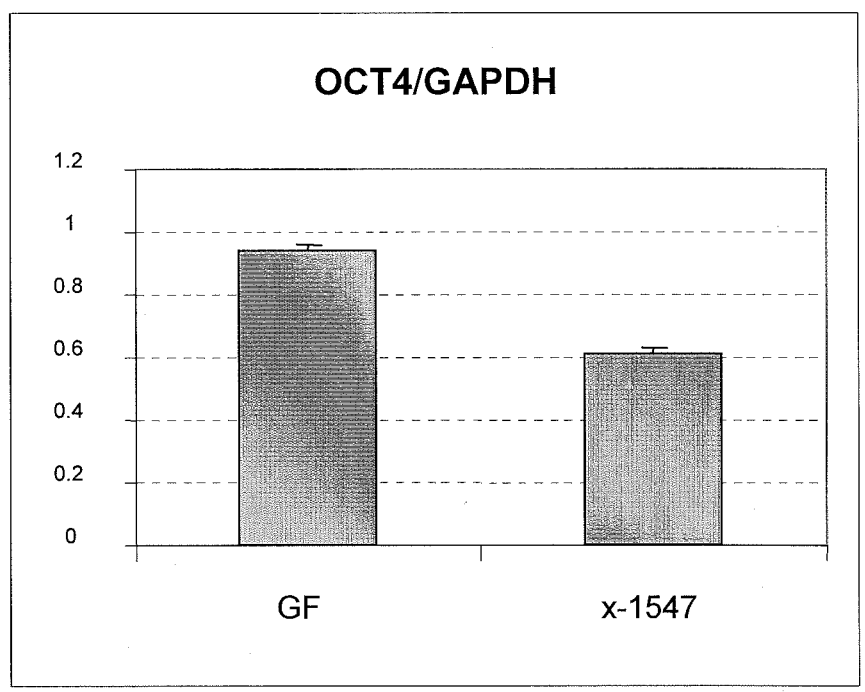
FIG. 2 shows levels of OCT4 mRNA in cells transfected with a vector encoding a fusion between an OCT4-targetd ZFP and the KOX-1 transcriptional repression domain (x-1547), compared to cells transfected with a vector encoding green fluorescent protein (GFP).

Results are shown in FIGS. 1 and 2. Introduction of the v-1547 construct, encoding a fusion between a ZFP targeted to OCT4 and the VP16 activation domain, resulted in an approximately two-fold increase in OCT4 mRNA levels, compared to cells transfected with a GFP-encoding vector (FIG. 1). Introduction of the x-1547 construct, encoding a fusion between an OCT4-targeted ZFP and the KOX-1 repression domain, resulted in a decrease in OCT4 mRNA levels, compared to cells transfected with a GFP-encoding vector (FIG. 2). These results demonstrate that it is possible to use engineered zinc finger proteins to regulate a key developmental control gene in stem cells.

Example 4

Effect of ZFP-Mediated Regulation of the OCT4 Gene on Expression of Downstream Genes As stated previously (see Example 1), upregulation of OCT4 in stem cells has been shown to result in upregulation of the Otx1 gene; while downregulation of OCT4 results in repression of Otx1 and activation of Hand1 expression. To determine whether ZFP-mediated regulation of OCT4 has the same effect on downstream genes, RNA from cells that had been transfected with v-1547 or with x-1547 (e.g., the same RNA samples that were analyzed in Example 3) was assayed for Otx1 and Hand1 mRNA levels, normalized to GAPDH mRNA.

Figure 3:
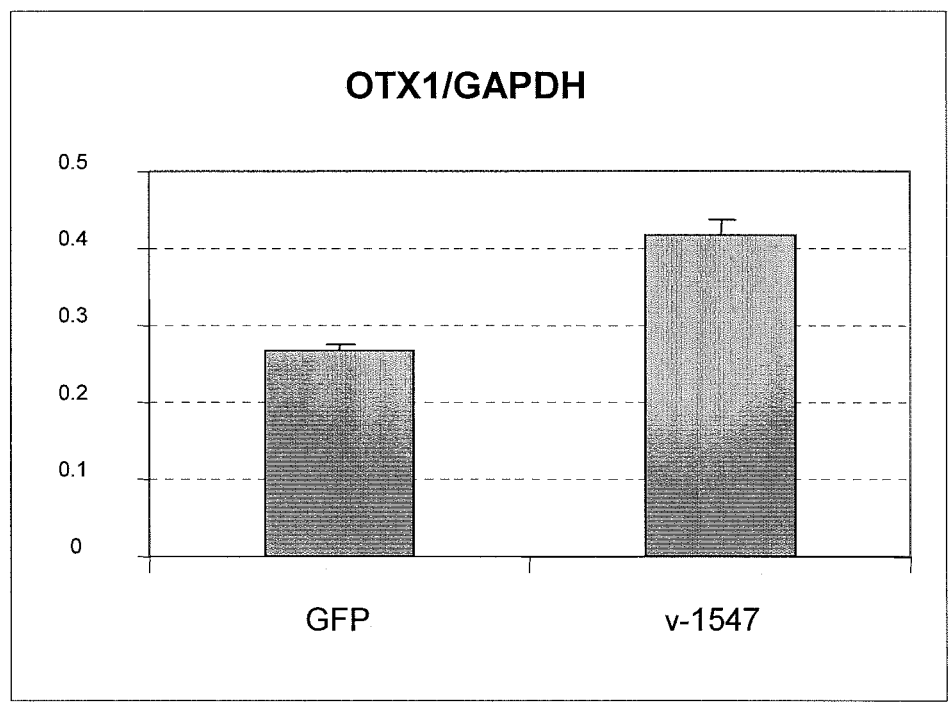
FIG. 3 shows levels of Otx1 mRNA in cells transfected with a vector encoding a fusion between an OCT4-targetd ZFP and the VP16 transcriptional activation domain (v-1547), compared to cells transfected with a vector encoding green fluorescent protein (GFP).
Figure 4:
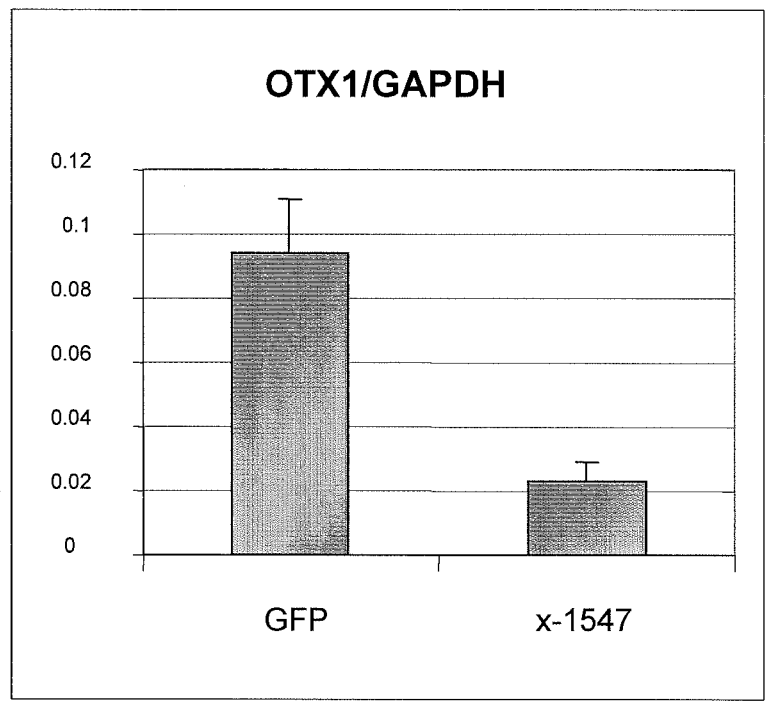
FIG. 4 shows levels of Otx1 mRNA in cells transfected with a vector encoding a fusion between an OCT4-targetd ZFP and the KOX-1 transcriptional repression domain (x-1547), compared to cells transfected with a vector encoding green fluorescent protein (GFP).
Figure 5:
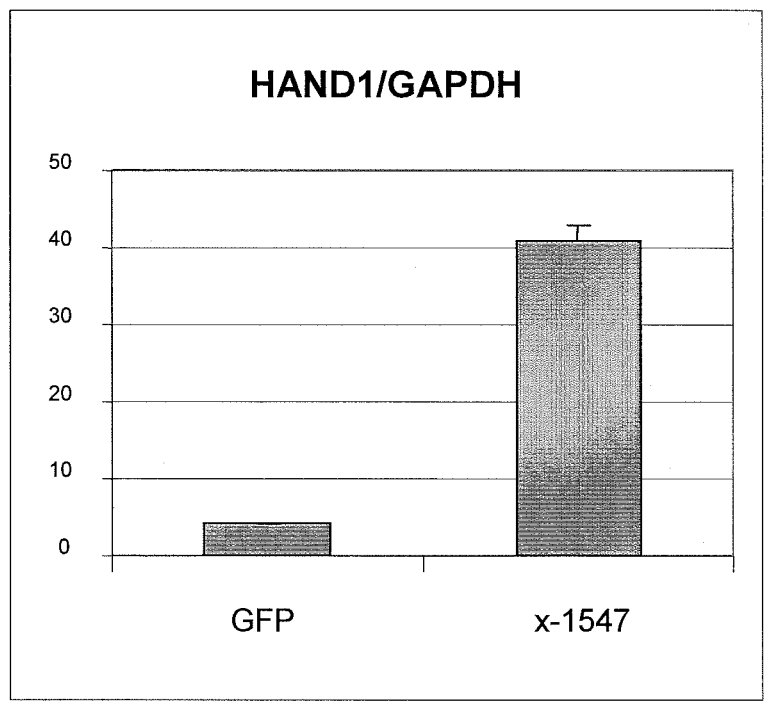
FIG. 5 shows levels of Hand1 mRNA in cells transfected with a vector encoding a fusion between an OCT4-targetd ZFP and the KOX-1 transcriptional repression domain (x-1547), compared to cells transfected with a vector encoding green fluorescent protein (GFP).

The results are shown in FIGS. 3, 4 and 5. FIG. 3 shows that, in cells in which OCT4 mRNA levels had been increased by the v-1547 ZFP, Otx1 mRNA levels were also increased, as previously observed. FIGS. 4 and 5 show analysis of RNA from cells in which OCT4 expression was downregulated by the x-1547 ZFP. FIG. 4 shows that Otx1 mRNA levels were also downregulated, and FIG. 5 shows that Hand1 mRNA levels increased following repression of OCT4 expression. Thus, these results demonstrate that modulation of OCT4 expression in stem cells with an engineered ZFP results in the expected co-regulation of downstream genes.

Example 5

Design of ZFPs that Bind the HOXB4 Gene

The HOXB4 gene is a homeobox transcription factor primarily expressed in the most primitive subpopulations of hematopoietic cells, and has been shown to be important for their proliferation. See, e.g., Helgason et al. (1996) *Blood* 87:2740-2749; Antonchuk et al. (2002) *Cell* 109:39-45.

A ZFP binding domain, targeted to four sites within the first exon of the HOXB4 gene, was designed using methods for the design and synthesis of zinc finger proteins able to bind to preselected sites disclosed in co-owned U.S. Pat. No. 6,453,242; WO 00/41566 and PCT/US01/43568. The target site and the amino acid sequences of the recognition regions of the zinc fingers of this protein are given in Table 5.

TABLE 5

Designed zinc finger protein binding domains

| ZFP# | binding target site | F1 sequence* | F2 sequence* | F3 sequence* |
|---|---|---|---|---|
| 1135 | HOXB4 | GYGGYGGGGRSDHLAR (SEQ ID NO: 20) | RSDELQR (SEQ ID NO: 21) | RSDELQR (SEQ ID NO: 22) | RSDERKR (SEQ ID NO: 23) |

*The amino acid sequences shown are those of amino acids -1 through +6 (with respect to the start of the alpha-helical portion of the zinc finger) and are given in the one-letter code Sequences encoding the ZFP binding domains shown in Table 5 were used to generate constructs which encode the ZFP fused to a VP16 transcriptional activation domain (v-1135) or a p65 transcriptional activation domain (s-1135), using methods disclosed in co-owned U.S. Pat. No. 6,453, 242 and co-owned WO 00/41566. These constructs were separately transfected into mouse ES cells, and their effects on expression of the HOXB4 gene were determined.

Example 6

Regulation of the HOXB4 Gene in Mouse Embryonic Stem Cells Using an Engineered Zinc Finger Protein Mouse embryonic stem cells were obtained, propagated and transfected as described in Example 3. Cells were transfected with v-1135 (Example 5), s-1135 (Example 5), or a green-fluorescent protein-encoding vector (GFP).

At 48 h after transfection, total cellular RNA was isolated and analyzed for HOXB4 mRNA as described in Example 3. Primers and probes used for mRNA analysis are given in Table 4.

Figure 6:
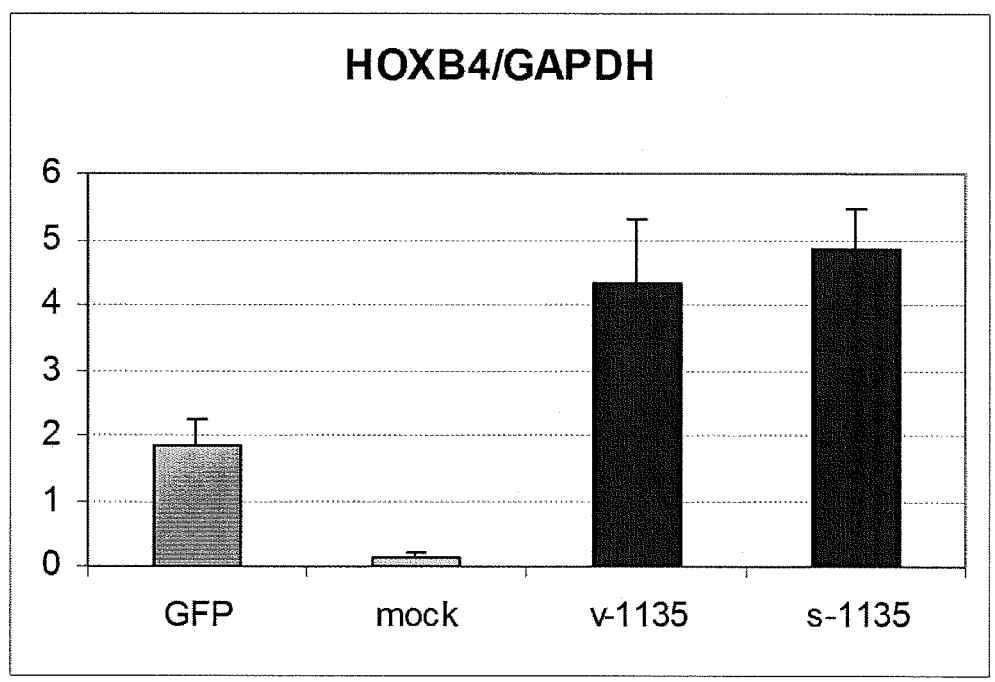
FIG. 6 shows levels of HOXB4 mRNA in cells transfected with vectors encoding fusions comprising either a HOXB4-targetd ZFP and the VP16 transcriptional activation domain (v-1135) or a HOXB4-targetd ZFP and the p65 transcriptional activation domain (s-1135), compared to cells transfected with a vector encoding green fluorescent protein (GFP). HOXB4 levels in mock-transfected cells are also shown.

The results, shown in FIG. 6, indicate that HOXB4 mRNA levels are increased 2- to 2.5-fold in cells transfected with vectors encoding a HOXB4-targeted ZFP fused to either of the two transcriptional activation domains. This provides further evidence that key developmental control gene can be regulated by engineered ZFPs in stem cells.

Example 7

Proliferation and Expansion of Hematopoietic Cells

Hematopoietic stem cells are obtained using, for example, the methods described in U.S. Pat. No. 5,681,559. Stem cells are cultured in media. ZFP proteins are engineered to target growth factors or other genes involved in self-renewal. The ZFPs are administered to cultured stem cells either as proteins or nucleotides encoding same.

To expand B-lymphocyte stem cells, ZFPs that repress expression of E2A, EBF and Pax-5 are administered. Similarly to expand hematopoietic lineages other than B-lymphocytes, ZFPs that repress genes encoding SCL/Tal-1, AML-1 and/or c-Myb are administered to the cell. T-cell progenitor populations are expanded by administering ZFPs that repress expression of TCF-1.

Example 8

Use of ZFPs to Differentiate Stem Cells

A. Pancreatic Stem Cell to Liver Cells

Pancreatic stem cells are obtained and cultured as described in Example 7 or using methods described in the art. ZFPs that modulate expression of albumin, b-integrin and other molecules are introduced into the cultured stem cells. Additionally, ZFPs used to maintain the stem cell phenotype in culture are eliminated. The pancreatic stem cells are induced to a differentiated hepatocyte phenotype characterized by functional albumin.

B. Neural Stem Cells into Hematopoietic Cells

Neural stem cells are obtained and cultured as described in Example 7 or by methods known in the art. ZFPs that modulate (e.g., activate) expression of SCL/Tal-1 and/or TCF/liver inhibitory factor (lif) are administered to the cells, either as proteins or polynucleotides encoding these ZFPs.

The invention claimed is:

1. A method of modulating activating homeobox protein B4 (HOXB4) gene expression in an isolated cell, the method comprising the step of administering one or more polynucleotides encoding one or more fusion proteins to the isolated cell, each fusion protein comprising a transcriptional activation domain and a zinc finger DNA-binding domain comprising 3 zinc finger domains comprising recognition helix region sequences as set forth in SEQ ID NO:21, 22 and 23 and further wherein the zinc finger DNA-binding domain binds to a target site in a HOXB4 gene.

2. The method of claim 1, wherein the target site comprises the sequence shown in SEQ ID NO:20.

3. The method of claim 1, wherein the isolated cell is a stem cell.

* * * * *

```
SEQUENCE LISTING

<160> NUMBER OF SEQ ID NOS: 33

<210> SEQ ID NO 1
<211> LENGTH: 9
<212> TYPE: DNA
<213> ORGANISM: Artificial
<220> FEATURE:
<223> OTHER INFORMATION: ZFP 1547 - OCT4 binding site

<400> SEQUENCE: 1 gaggtkggg                                                                  9

<210> SEQ ID NO 2
<211> LENGTH: 7
<212> TYPE: PRT
<213> ORGANISM: Artificial
<220> FEATURE:
<223> OTHER INFORMATION: ZFP 1547 - OCT4 F1

<400> SEQUENCE: 2

Arg Ser Asp His Leu Ala Arg
1               5

<210> SEQ ID NO 3
<211> LENGTH: 7
<212> TYPE: PRT
<213> ORGANISM: Artificial
<220> FEATURE:
<223> OTHER INFORMATION: ZFP 1547 - OCT4 F2

<400> SEQUENCE: 3

Thr Ser Gly Ser Leu Thr Arg
1               5

<210> SEQ ID NO 4
<211> LENGTH: 7
<212> TYPE: PRT
<213> ORGANISM: Artificial
<220> FEATURE:
<223> OTHER INFORMATION: ZFP 1547 - OCT4 F3

<400> SEQUENCE: 4

Arg Ser Asp Asn Leu Ala Arg
1               5

<210> SEQ ID NO 5
```

```
<210> SEQ ID NO 5
<211> LENGTH: 19
<212> TYPE: DNA
<213> ORGANISM: Artificial
<220> FEATURE:
<223> OTHER INFORMATION: OCT4 forward primer

<400> SEQUENCE: 5
ctcaccctgg gcgttctct                                              19

<210> SEQ ID NO 6
<211> LENGTH: 18
<212> TYPE: DNA
<213> ORGANISM: Artificial
<220> FEATURE:
<223> OTHER INFORMATION: OCT4 reverse primer

<400> SEQUENCE: 6
aggcctcgaa gcgacaga                                               18

<210> SEQ ID NO 7
<211> LENGTH: 25
<212> TYPE: DNA
<213> ORGANISM: Artificial
<220> FEATURE:
<223> OTHER INFORMATION: OCT4 probe

<400> SEQUENCE: 7
tggaaaggtg ttcagccaga ccacc                                       25

<210> SEQ ID NO 8
<211> LENGTH: 23
<212> TYPE: DNA
<213> ORGANISM: Artificial
<220> FEATURE:
<223> OTHER INFORMATION: OTX1 forward primer

<400> SEQUENCE: 8
atcaacctgc cagagtccag agt                                         23

<210> SEQ ID NO 9
<211> LENGTH: 19
<212> TYPE: DNA
<213> ORGANISM: Artificial
<220> FEATURE:
<223> OTHER INFORMATION: OTX1 reverse primer

<400> SEQUENCE: 9
ccgggttttc gttccattc                                              19

<210> SEQ ID NO 10
<211> LENGTH: 21
<212> TYPE: DNA
<213> ORGANISM: Artificial
<220> FEATURE:
<223> OTHER INFORMATION: OTX1 probe

<400> SEQUENCE: 10
agtgccgcca gcagcagcag a                                           21

<210> SEQ ID NO 11
<211> LENGTH: 18
<212> TYPE: DNA
<213> ORGANISM: Artificial
<220> FEATURE:
<223> OTHER INFORMATION: Hand1 Forward primer

<400> SEQUENCE: 11
```
gccaaggatg cacaagca                                                    18

<210> SEQ ID NO 12
<211> LENGTH: 18
<212> TYPE: DNA
<213> ORGANISM: Artificial
<220> FEATURE:
<223> OTHER INFORMATION: Hand1 reverse primer

<400> SEQUENCE: 12
gggctgctga ggcaactc                                                    18

<210> SEQ ID NO 13
<211> LENGTH: 23
<212> TYPE: DNA
<213> ORGANISM: Artificial
<220> FEATURE:
<223> OTHER INFORMATION: Hand1 probe

<400> SEQUENCE: 13
cttttccgct tgctttcgcg acc                                              23

<210> SEQ ID NO 14
<211> LENGTH: 18
<212> TYPE: DNA
<213> ORGANISM: Artificial
<220> FEATURE:
<223> OTHER INFORMATION: HOXB4 forward primer

<400> SEQUENCE: 14
ggaacagcga gcaccgaa                                                    18

<210> SEQ ID NO 15
<211> LENGTH: 27
<212> TYPE: DNA
<213> ORGANISM: Artificial
<220> FEATURE:
<223> OTHER INFORMATION: HOXB4 reverse primer

<400> SEQUENCE: 15
cctttctata aataaggctt ccctacc                                          27

<210> SEQ ID NO 16
<211> LENGTH: 20
<212> TYPE: DNA
<213> ORGANISM: Artificial
<220> FEATURE:
<223> OTHER INFORMATION: HOXB4 probe

<400> SEQUENCE: 16
ccccgggctt gagcccagaa                                                  20

<210> SEQ ID NO 17
<211> LENGTH: 21
<212> TYPE: DNA
<213> ORGANISM: Artificial
<220> FEATURE:
<223> OTHER INFORMATION: GAPDH forward primer

<400> SEQUENCE: 17
cccatgtttg tgatgggtgt g                                                21

<210> SEQ ID NO 18
<211> LENGTH: 21
<212> TYPE: DNA

```
<213> ORGANISM: Artificial
<220> FEATURE:
<223> OTHER INFORMATION: GAPDH reverse primer

<400> SEQUENCE: 18
tggcatggac tgtggtcatg a                                              21

<210> SEQ ID NO 19
<211> LENGTH: 24
<212> TYPE: DNA
<213> ORGANISM: Artificial
<220> FEATURE:
<223> OTHER INFORMATION: GAPDH probe

<400> SEQUENCE: 19
atcctgcacc accaactgct tagc                                           24

<210> SEQ ID NO 20
<211> LENGTH: 10
<212> TYPE: DNA
<213> ORGANISM: Artificial
<220> FEATURE:
<223> OTHER INFORMATION: ZFP 1135 - HOXB4 binding site

<400> SEQUENCE: 20 gyggygggg                                                            10

<210> SEQ ID NO 21
<211> LENGTH: 7
<212> TYPE: PRT
<213> ORGANISM: Artificial
<220> FEATURE:
<223> OTHER INFORMATION: ZFP 1135 - HOXB4 F1

<400> SEQUENCE: 21

Arg Ser Asp His Leu Ala Arg
1               5

<210> SEQ ID NO 22
<211> LENGTH: 7
<212> TYPE: PRT
<213> ORGANISM: Artificial
<220> FEATURE:
<223> OTHER INFORMATION: ZFP 1135 - HOXB4 F2

<400> SEQUENCE: 22

Arg Ser Asp Glu Leu Gln Arg
1               5

<210> SEQ ID NO 23
<211> LENGTH: 7
<212> TYPE: PRT
<213> ORGANISM: Artificial
<220> FEATURE:
<223> OTHER INFORMATION: ZFP 1135 - HOXB4 F3

<400> SEQUENCE: 23

Arg Ser Asp Glu Arg Lys Arg
1               5

<210> SEQ ID NO 24
<211> LENGTH: 25
<212> TYPE: PRT
<213> ORGANISM: Artificial
<220> FEATURE:
<223> OTHER INFORMATION: C2H2 motif
<220> FEATURE:
```

```
<221> NAME/KEY: MISC_FEATURE
<222> LOCATION: (2)..(5)
<223> OTHER INFORMATION: Xaa = any amino acid
<220> FEATURE:
<221> NAME/KEY: MISC_FEATURE
<222> LOCATION: (4)..(5)
<223> OTHER INFORMATION: Xaa may be present or absent
<220> FEATURE:
<221> NAME/KEY: MISC_FEATURE
<222> LOCATION: (7)..(18)
<223> OTHER INFORMATION: Xaa = any amino acid
<220> FEATURE:
<221> NAME/KEY: MISC_FEATURE
<222> LOCATION: (20)..(24)
<223> OTHER INFORMATION: Xaa = any amino acid
<220> FEATURE:
<221> NAME/KEY: MISC_FEATURE
<222> LOCATION: (23)..(24)
<223> OTHER INFORMATION: Xaa may be present or absent

<400> SEQUENCE: 24

Cys Xaa Xaa Xaa Xaa Cys Xaa Xaa Xaa Xaa Xaa Xaa Xaa Xaa Xaa
 1               5                  10                  15

Xaa Xaa His Xaa Xaa Xaa Xaa Xaa His
            20                  25

<210> SEQ ID NO 25
<211> LENGTH: 5
<212> TYPE: PRT
<213> ORGANISM: Artificial
<220> FEATURE:
<223> OTHER INFORMATION: linker

<400> SEQUENCE: 25

Asp Gly Gly Gly Ser
 1               5

<210> SEQ ID NO 26
<211> LENGTH: 5
<212> TYPE: PRT
<213> ORGANISM: Artificial
<220> FEATURE:
<223> OTHER INFORMATION: linker

<400> SEQUENCE: 26

Thr Gly Glu Lys Pro
 1               5

<210> SEQ ID NO 27
<211> LENGTH: 9
<212> TYPE: PRT
<213> ORGANISM: Artificial
<220> FEATURE:
<223> OTHER INFORMATION: linker

<400> SEQUENCE: 27

Leu Arg Gln Lys Asp Gly Glu Arg Pro
 1               5

<210> SEQ ID NO 28
<211> LENGTH: 4
<212> TYPE: PRT
<213> ORGANISM: Artificial
<220> FEATURE:
<223> OTHER INFORMATION: linker

<400> SEQUENCE: 28

Gly Gly Arg Arg
 1
```

```
<210> SEQ ID NO 29
<211> LENGTH: 4
<212> TYPE: PRT
<213> ORGANISM: Artificial
<220> FEATURE:
<223> OTHER INFORMATION: linker

<400> SEQUENCE: 29

Gly Gly Gly Ser
1

<210> SEQ ID NO 30
<211> LENGTH: 8
<212> TYPE: PRT
<213> ORGANISM: Artificial
<220> FEATURE:
<223> OTHER INFORMATION: linker

<400> SEQUENCE: 30

Gly Gly Arg Arg Gly Gly Gly Ser
1               5

<210> SEQ ID NO 31
<211> LENGTH: 9
<212> TYPE: PRT
<213> ORGANISM: Artificial
<220> FEATURE:
<223> OTHER INFORMATION: linker

<400> SEQUENCE: 31

Leu Arg Gln Arg Asp Gly Glu Arg Pro
1               5

<210> SEQ ID NO 32
<211> LENGTH: 12
<212> TYPE: PRT
<213> ORGANISM: Artificial
<220> FEATURE:
<223> OTHER INFORMATION: linker

<400> SEQUENCE: 32

Leu Arg Gln Lys Asp Gly Gly Ser Glu Arg Pro
1               5                   10

<210> SEQ ID NO 33
<211> LENGTH: 16
<212> TYPE: PRT
<213> ORGANISM: Artificial
<220> FEATURE:
<223> OTHER INFORMATION: linker

<400> SEQUENCE: 33

Leu Arg Gln Lys Asp Gly Gly Ser Gly Gly Gly Ser Glu Arg Pro
1               5                   10                  15
```